US008148335B2

(12) United States Patent
Moe et al.

(10) Patent No.: US 8,148,335 B2
(45) Date of Patent: Apr. 3, 2012

(54) DE-N-ACETYL SIALIC ACID ANTIGENS, ANTIBODIES THERETO, AND METHODS OF USE IN CANCER THERAPY

(75) Inventors: Gregory R. Moe, Alameda, CA (US); Charles Paul Plested, Walnut Creek, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 1249 days.

(21) Appl. No.: 11/645,255

(22) Filed: Dec. 22, 2006

(65) Prior Publication Data

US 2010/0260762 A1    Oct. 14, 2010

Related U.S. Application Data

(63) Continuation-in-part of application No. 11/166,781, filed on Jun. 23, 2005, now Pat. No. 7,595,307.

(60) Provisional application No. 60/753,847, filed on Dec. 23, 2005, provisional application No. 60/582,672, filed on Jun. 23, 2004.

(51) Int. Cl.
*A61K 31/715* (2006.01)
*C07H 5/06* (2006.01)

(52) U.S. Cl. .................. 514/25; 536/17.9; 536/55.1

(58) Field of Classification Search .................. None
See application file for complete search history.

(56) References Cited

U.S. PATENT DOCUMENTS

| | | | |
|---|---|---|---|
| 4,216,208 A | 8/1980 | De Barbieri | |
| 4,314,999 A | 2/1982 | De Barbieri | |
| 4,727,136 A | 2/1988 | Jennings et al. | |
| 4,797,477 A | 1/1989 | Yoshimura et al. | |
| 5,332,756 A | 7/1994 | Mongelli et al. | |
| 5,639,622 A * | 6/1997 | Bosslet et al. | 435/7.23 |
| 5,811,102 A | 9/1998 | Jennings et al. | |
| 5,846,951 A | 12/1998 | Gregoriadis | |
| 5,969,130 A | 10/1999 | Jennings et al. | |
| 6,030,619 A | 2/2000 | Granoff et al. | |
| 6,048,527 A | 4/2000 | Granoff et al. | |
| 6,274,568 B1 | 8/2001 | Schnaar et al. | |
| 6,350,449 B1 | 2/2002 | Jennings et al. | |
| 6,638,513 B2 | 10/2003 | Seid | |
| 7,595,307 B2 | 9/2009 | Moe et al. | |
| 2002/0034518 A1 | 3/2002 | Seid | |
| 2007/0010482 A1 | 1/2007 | Moe et al. | |
| 2009/0010949 A1 * | 1/2009 | Moe et al. | 424/184.1 |

FOREIGN PATENT DOCUMENTS

| | | |
|---|---|---|
| EP | 0504 202 B1 | 3/1995 |
| WO | WO99/10372 | 3/1999 |
| WO | WO 01/09298 | 2/2001 |
| WO | WO 02/09744 | 2/2002 |
| WO | WO 2006/002402 A2 | 1/2006 |
| WO | WO 2009047792 | 4/2009 |

OTHER PUBLICATIONS

Hayrinen et al., "Antibodies to Polysialic Acid and its N-Propyl Derivative: Binding Properties and Interactionwith Human Embryonal Brain Glycopeptides" The Journal of Infectious Diseases (1995) vol. 171 No. 6 pp. 1481-1490.*
The Merck Manual of Diagnosis and Therapy, Seventeenth Edition, published 1999 by Merck Research Laboratories, pp. 986-995.*
Azmi et al. "Variable region sequences and idiotypic expression of a protective human immunoglobulin M antibody to capsular polysaccharides of *Neisseria meningitidis* group B and *Escherichia coli* K1", 1994 Infect Immun 62:1776-1786.
Ashton et al. "Protective efficacy of mouse serum to the N-propionyl derivative of meningococcal group B polysaccharide", 1989 Microb Pathog 6:455-458.
Bruge, et al. "Clinical evaluation of a group B meningococcal N-propionylated polysaccharide conjugate vaccine in adult, male volunteers", Vaccine, 22 (2004) 1087-1096.
Baumann, et al., "Comparison of the conformation of the epitope of $\alpha(2\rightarrow8)$ polysialic acid with its reduced and N-acyl derivatives", Biochemistyr 1993, 32, 4007-4013.
Brisson et al., "Helical eptope of the group B meningococcal $\alpha(2\rightarrow8)$-Linked sialic acid polysaccharide", Biochemistry 1992, 31, 4996-5004.
Coquillat et al., "Activity of cross-reactivity of antibodies induced in mice by immunization with a group B meningococcal conjugate", Infect and Immun, 2001, vol. 69, No. 11, 7130-7139.
Devi et al., "Preclinical evaluation of group B *Neisseria meningitidis* and *Escherichia coli* K92 capsular polysaccharide-protein conjugate vaccines in juvenile rhesus monkeys." 1997, Infect Immun 65:1045-52.
Evans, et al., "Evidence for the extended helical nature of polysaccharide epitopes. The 2.8 Å resolution structure and thermodynamics of ligand binding of an antigen binding fragment specific for $\alpha(2\rightarrow8)$-polysialic acid", Biochemistry, 1995, 34, 6737-6744.
Guo et al., "Protein-polysaccharide conjugation", 2001, Humana Press Inc. p. 49-61.
Fusco et al. "Preclinical evaluation of a novel group B meningococcal conjugate vaccine that elicits bactericidal activity in both mice and nonhuman primates," (1997) J. Infect. Dis. 175:364-72.
Goldschneider et al., "Human Immunity to the Meningococcus. I The Role of Humoral Antibodies", 1969, *J. Exp. Med.* 129:1307-1326.
Granoff et al. "Bactericidal monoclonal antibodies that define unique meningococcal B polysaccharide eptopes that do not cross-react with human polysialic acid", 1998 J Immunol 160:5028-5036.
Kabat, et al. "The epitope associated with the binding of the capsular polysaccharide of the group B meningococcus and of *Escherichia coli* K1 to a human monoclonal macroglobulin IgMNOV", J. Exp. Med. Aug. 1, 1998;168(2):699-711.

(Continued)

*Primary Examiner* — Eric S Olson
(74) *Attorney, Agent, or Firm* — Carol L. Francis; Bozicevic, Field & Francis LLP

(57) ABSTRACT

The present invention generally provides compositions methods and composition relating to the diagnosis and/or treatment of cancers having a cell surface de-N-acetylated sialic acid antigen, e.g., an at least partially de-N-acetylated ganglioside and/or a de-N-acetylated sialic acid-modified cell surface protein.

23 Claims, 35 Drawing Sheets

OTHER PUBLICATIONS

Hong, et al., "Inhibitory effect of K-76 monocarboxylic acid, and anticomplementary agent, on the C3b inactivator system", The J Immunol, 1981, vol. 127, No. 1, pp. 104-108.

Jennings et al., "Determinant specificities of the groups B and C polysaccharides of *Neisseria meningitides*", 1981, supra Jennings 1985 J Immunol 134:2651-57.

Jennings et al. "Induction of meningococcal group B polysaccharide-specific IgG antibodies in mice by using an N-propionylated B polysaccharide-tetanus toxoid conjugate vaccine", 1986, J Immunol 137:1708-1713.

Jennings et al. "N-propionylated group B meningococcal polysaccharide mimics a unique eptode on group B *Neisseria meningitides*", 1987, J Exp Med 165:1207-1211.

Jennings et al. "Unique intermolecular bactericidal epitope involving the homosialopolysaccharide capsule on the cell surface of group B *Neisseria meningitidis* and *Escherichia coli* K1$^1$", 1989 J Immunol 142:3585-3591.

Lifely et al., "Immune responses in mice to different noncovalent complexes of meningococcal B polysaccharide and outer membrane proteins", Infection & Immunity, 1988, vol. 56, No. 12, p. 3221-3227.

Lifely et al., "Sialic acid polysaccharide antigens of *Neisseria meningitidis* and *Escherichia coli*: Esterification between adjacent residues", Carbohydrate Research, 1981, 94, 193-203.

Lifely et al., "Specificity of the immune response to the group B polysaccharide of *Neisseria meningitidis*", Immunology, 1991, 74, 490-496.

Michon, et al., "Conformational differences between linear $\alpha(2\rightarrow 8)$-linked homosialooligosaccharides and the epitope of the group B meaningococcal polysaccharide", Biochemistry, 1987, 26, 8399-8405.

Moreno et al. "Immunity and protection of mice against *Neisseria meningitidis* group B by vaccination, using polysaccharide complexed with outer membrane proteins: a comparison with purified B polysaccharide", Infection & Immunity, 1985, vol. 47, No. 2, 527-533.

Pandey, et al,"Immunoglobulin allotypes and immune response to meningococcal group B polysaccharide", J. Clin. Invest, 1981, vol. 68, 1378-1380.

Pon et al. "N-propionylated group B meningococcal polysaccharide mimics a unique bactericidal capsular epitope in group B *Neisseria meningitidis*", 1997 J Exp Med 185:1929-1938.

R. Roy et al. "Efficient Synthesis of alpha(2-8)-linked N-Acetyl and N-Glycolylneuraminic Acid Disaccharides from Colominic Acid", Glycoconjugate Journal, vol. 7, 1990, pp. 3-12.

Sjoberg, et al. "Expression of De-N-acetyl-gangliosides in human melanoma cells is induced by genistein or nocodazole", The journal of Biological Chemistry, 1995, vol. 270, No. 7, 2921,2930.

Stephens et al. "Insertion of Tn916 in *Neisseria meningitidis* resulting in loss of group B capsular polysaccharide", 1991, Infect Immun 59:4097-4102.

Shin et al. "Monoclonal antibodies specific for *Neisseria meningitidis* group B polysaccharide and their peptide mimotopes", 2001 Infect Immun 69:3335-3342.

Wyle et al., "Immunologic response of man to group B meaningococcal polysaccharide vaccines", 1972,*J. Infect. Dis.* 126: 514-522.

Zollinger, et al., "Complex of meningococcal group B polysaccharide and type 2 outer membrane protein immunogenic in man", 1979, *J. Clin. Invest.* 63: 836-834.

Finne et al. "Occurrence of alpha 2-8 linked polysialosyl units in a neural cell adhesion molecule", 1983, Biochem Biophys Res Commun 112:482.

Frosch et al. "NZB mouse system for production of monoclonal antibodies to weak bacterial antigens: isolation of an IgG antibody to the polysaccharide capsules of *Escherichia coli* K1 and group B meningococci", 1985 Proc Natl Acad Sci U S A 82:1194.

Griffiss, J. M. 1995. Mechanisms of host immunity, p. 35-70. In K. Cartwright (ed.), Meningococcal disease. John Wiley & Sons, Chichester, England.

Granoff et al., "Bactericidal monoclonal antibodies that define unique meningococcal B polysaccharide epitopes that do not cross-react with human polysialic acid", 1998, J. Immunol; 160: 5028-5036.

Hurpin et al. "Bactericidal activity of two $IgG_{2a}$ murine monoclonal antibodies with distinct fine specificities for group B *Neisseria meningitidis capsular polysaccharide*", 1992 Hybridoma 11:677.

Hayrinen et al. "Antibodies to polysialic acid and its N-propyl derivative: binding properties and interaction with human embryonal brain glycopeptides", 1995, J Infect Dis 171:1481.

Jones D. Epidemiology of meningococcal disease in Europe and the USA. In: Cartwright K, ed. Meningococcal disease. New York: John Wiley & Sons, 1995;147-157.

Jennings et al., "Immunochemistry of groups A, B, and C meningococcal polysaccharide-tetanus toxoid conjugates", 1981, J Immunol 127:1011-8.

Mandrell et al. "Measurement of antibodies to meningococcal group B polysaccharide: low avidity binding and equilibrium binding constants", 1982 J Immunol 129:2172-8.

Moreno et al. Immunological properties of monoclonal antibodies specific for meningococcal polysaccharides: the protective capacity of IgM antibodies specific for polysaccharide group B. 1983 J Gen Microbiol 129 (Pt 8):2451-6.

Mandrell et al. "Complement-mediated bactericidal activity of human antibodies to poly alpha $2\rightarrow 48$ N-acetylneuraminic acid, the capsular polysaccharide of *Neisseria meningitidis* serogroup B.", 1995 J Infect Dis 172:1279-89.

Raff et al. "Human monoclonal antibody with protective activity for *Escherichia coli* K1 and *Neisseria meningitidis* group B infections", 1988 J Infect Dis 157:118-26.

Rohr et al. Structure and biosynthesis of surface polymers containing polysialic acid in *Escherichia coli*. 1980 J Biol Chem 255:2332-42.

Chapman et al. Sequential Immunization of Melanoma Patients with GD3 Ganglioside Vaccine and Anti-Idiotypic Monoclonal Antibody that Mimics GD3 Ganglioside. Clinical Cancer Research, 2004, vol. 10, 4717-4723.

Chapman et al. Induction of IgG Antibodies Against $G_{D3}$ Ganglioside in Rabbits by an Anti-idiotypic Monocloncal Antibody. Department of Medicine and the Immunology Program, 1991, 88:186-192.

Granoff et al. Bactericidal Monoclonal Antibodies That Define Unique Meningococcal B Polysaccharide Epitopes That Do Not Cross-React with Human Polysialic Acid1 (1998) J Immunol 160, 5028-36.

Moe et al. Epitopes Recognized by a Nonautoreactive Murine Anti-N-Propionyl Meningococcal Group B Polysaccharide Monoclonal Antibody (2005) Infect Immun 73, 2123-8.

Moe et al. GenBank Accession Nos. DQ113491 submitted Jun. 30, 2005; ROD Mar. 8, 2006.

Moe et al. GenBank Accession Nos. DQ113492 submitted Jun. 30, 2005; ROD Mar. 8, 2006.

Ritter et al. Antibody Response to Immunization with Ganglioside GD3 and GD3 Congeners (Lactones, Amide and Ganliosidol) in Patients with Malignant Melanoma. Int. J. Cancer, (1991)48, 379-385.

Ritter et al. Analysis of the Antibody Response to Immunization with Purified *O-Acetyl* GD3 Gangliosides in Patients with Malignant Melanoma. Int. J. Cancer, (1995) 62, 668-672.

Singh, et al., Advances in vaccine adjuvants., Nature Biotechnology 17, 1075-1081, Nov. 1999.

Sonnenburg, et al., Characterization of the acid stability of glycosidically linked neuraminic acid: use in detecting de-N-acetyl-gangliosides in human melanoma., J Biol Chem. May 17, 2002;277(20):17502-10.

Chammas et al. De-N-acetyl-gangliosides in Humans: Unusual Subcellular Distribution of a Novel Tumor Antigen. Cancer Research. Mar. 15, 1999, vol. 59, pp. 1337.1346, see Table 1, p. 1338, second column, p. 1343, first column, lines 7-8.

Chapman, A. Pegylated antibodies and antibody Fragments for improved therapy: a review. Advanced Drug Delivery Reviews. 2002, vol. 54, pp. 531-545, see abstract.

Gabri et al. Role of cell surface OM3 ganglioside and sialic acid in the antitumor activity of a GM3-based vaccine in the murine B16 melanoma model. Journal of Cancer Research and Clinical Oncology. 2002, vol. 128, pp. 669-677, see p. 670, second column and p. 672, first column.

Granoff et al. Bactericidal Monoclonal Antibodies That Define Unique Meningococcal B Polysaccharide Epitopes That Do Not Cross-React with Human Polysialic Acid. Journal of Immunology. 1998, vol. 160, pp. 5028-5036, Table 1 and p. 5029, second column.

Hellstrom et al. Strong antitumor activites of IgG3 antibodies to a human melanoma associated ganglioside. Proceeding of the National Academy of Sciences. Mar. 1985, vol. 82, pp. 1499-1502, see p. 1500 and p. 1502, first column.

Herlyn, et al. Medline on STN (Columbus, Ohio, U.S.A.), 'Production and characterization of monoclonal antibodies against human malignant melanoma', Cancer investigations, 1983, "01. I, No. 3, pp. 215-224.

Moe et al. Epitopes Recognized by a Nonautoreactive Murine Anti-N-Propionyl Meningococcal Group B Polysaccharide Monoclonal Antibody. Infection and immunity. Apr. 2005, vol. 73, pp. 2123-2128, p. 2126, legend for figure 3, p. 2124, first column, p. 2124, second column, lines 3-4 and p. 2126, second column, lines 30-31.

Sjoberg el al. Expression of De-N-acetyl-gangliosides in Human Melanoma Cells Is Induced by Genistein or Nocodazole. The Journal of Biologilcal Chemistry. Feb. 17, 1995, vol. 270, pp. 2921-2930, see pp. 2927-2930 and p. 2924, second column, first full paragraph.

Fondy, et al. (1981) "Haloacetamido analogs of 2-amino-2-deoxy-D-mannose. Syntheses and effects on tumor-bearing mice" *J. Med. Chem.* 24(7):848-852.

Brown & Gatter (2002) "Ki67 protein: the immaculate deception?" *Histopathology* 40(1):2-11.

Dippold, et al. (1980) "Cell surface antigens of human malignant melanoma: definition of six antigenic systems with mouse monoclonal antibodies" *Proc Natl Acad Sci USA* 77(10): 6114-6118.

GenBank Accession No. DQ113489 "Mus musculus clone SEAM 2 immunoglobulin heavy chain variable region mRNA, partial cds" dated Mar. 8, 2006.

GenBank Accession No. DQ113490 "Mus musculus clone SEAM 2 immunoglobulin light chain variable region mRNA, partial cds" dated Mar. 8, 2006.

GenBank Accession No. DQ113493 "Mus musculus clone SEAM 12 immunoglobulin heavy chain variable region mRNA, partial cds" dated Mar. 8, 2006.

GenBank Accession No. DQ113494 "Mus musculus clone SEAM 12 immunoglobulin light chain variable region mRNA, partial cds" dated Mar. 8, 2006.

GenBank Accession No. DQ113495 "Mus musculus clone SEAM 18 immunoglobulin heavy chain variable region mRNA, partial cds" dated Mar. 8, 2006.

GenBank Accession No. DQ113496 "Mus musculus clone SEAM 18 immunoglobulin light chain variable region mRNA, partial cds" dated Mar. 8, 2006.

GenBank Accession No. DQ113497 "Mus musculus clone SEAM 35 immunoglobulin heavy chain variable region mRNA, partial cds" dated Mar. 8, 2006.

GenBank Accession No. DQ113498 "Mus musculus clone SEAM 35 immunoglobulin light chain variable region mRNA, partial cds" dated Mar. 8, 2006.

Graus, et al. (1984) "Distribution of the ganglioside GD3 in the human nervous system detected by R24 mouse monoclonal antibod" *Brain Res* 324(1):190-4.

Houghton, et al. (1985) "Mouse monoclonal IgG3 antibody detecting GD3 ganglioside: a phase I trial in patients with malignant melanoma" *Proc Natl Acad Sci USA* 82(4):1242-1246.

Livingston, et al. (1988) "Extended polysialic acid chains (n greater than 55) in glycoproteins from human neuroblastoma cells" *J Biol Chem* 263(19):9443-9448.

Panneersel Vam, et al. (1986) "A molecular mechanism of complement resistance of human melanoma cells" *J Immunol* 136(7): 2534-2541.

Real, et al. (1985) "Surface antigens of melanomas and melanocytes defined by mouse monoclonal antibodies: specificity analysis and comparison of antigen expression in cultured cells and tissues" *Cancer Res* 45(9):4401-4411.

Vadhan-Raj, et al. (1988) "Phase I trial of a mouse monoclonal antibody against GD3 ganglioside in patients with melanoma: induction of inflammatory responses at tumor sites" *J Clin Oncol* 6(10): 1636-1648.

Welt, et al. (1987) "Immune and nonimmune effector functions of IgG3 mouse monoclonal antibody R24 detecting the disialoganglioside GD3 on the surface of melanoma cells" *Clin Immunol Immunopathol* 45(2): 214-229.

* cited by examiner

FIGURE 5

SUMMARY OF MS DATA FOR POLYSACCHARIDE SELECTED BY SEAM MABS

| Ion putative structure | Calculated mass (Daltons) | | Selecting "SEAM" monoclonal antibody | | | |
|---|---|---|---|---|---|---|
| | | | 2 | 3 | 12 | 18 |
| | Monoisotopic | Average | Observed mass/charge | | | |
| $[II + Na^+]^-$ | 579.16 | 579.46 | 579.378 | 579.400 | 579.482 | 1.  579.328 |
| $[I]^-$ | 559.20 | 559.50 | 559.290 | 559.390 | 559.314 | 559.525 |
| $[II]^-$ | 557.18 | 557.48 | 557.289 | 557.392 | 557.403 | 557.305 |
| $[III\ or\ IV]^-$ | 541.17 | 541.45 | 541.162 | 541.128 | 541.168 | - |
| $[V]^-$ | 539.17 | 539.46 | 539.169 | 539.249 | 539.157 | - |
| $[VI]^-$ | 523.18 | 523.47 | 522.731 | 522.867 | 522.813 | - |
| $[VII]^-$ | 515.17 | 515.44 | 514.540 | 514.710 | 514.616 | - |
| $[II-CH_2O]^-$ | 527.17 | 527.45 | - | - | 526.975 | 526.991 |
| [Mixture of VII,VIII]$^-$ | 499.18, 497.16 | | 498.219 | 498.289 | 498.273 | - |

The estimate of error for observed masses is ±0.1%.

FIGURE 6
Structure I
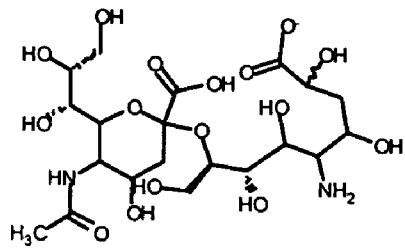
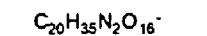
C_{20}H_{35}N_{2}O_{16}^{-}
Exact Mass: 559.20
Mol. Wt.: 559.50
C, 42.93; H, 6.31; N, 5.01; O, 45.75
FIGURE 7
Structure II
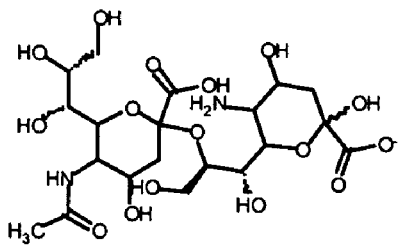
C_{20}H_{33}N_{2}O_{16}^{-}
Exact Mass: 557.18
Mol. Wt.: 557.48
C, 43.09; H, 5.97; N, 5.03; O, 45.92
FIGURE 8
Structure III
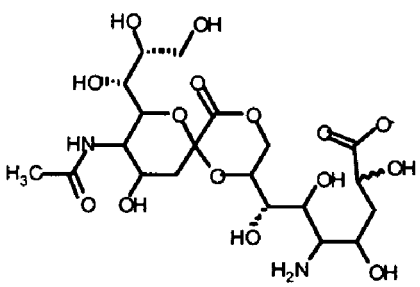
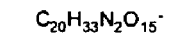
C_{20}H_{33}N_{2}O_{15}^{-}
Exact Mass: 541.19
Mol. Wt.: 541.48
C, 44.36; H, 6.14; N, 5.17; O, 44.32
FIGURE 9
Structure IV
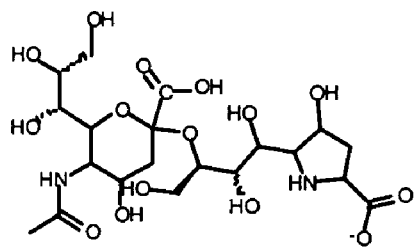
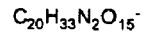
C_{20}H_{33}N_{2}O_{15}^{-}
Exact Mass: 541.19
Mol. Wt.: 541.48
C, 44.36; H, 6.14; N, 5.17; O, 44.32

FIGURE 10
Structure V
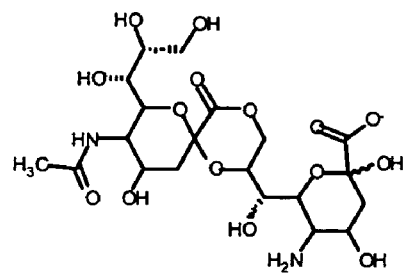
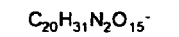
$C_{20}H_{31}N_2O_{15}^-$
Exact Mass: 539.17
Mol. Wt.: 539.46
C, 44.53; H, 5.79; N, 5.19; O, 44.49
FIGURE 11
Structure VI
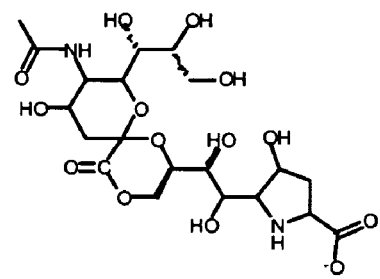
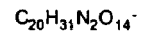
$C_{20}H_{31}N_2O_{14}^-$
Exact Mass: 523.18
Mol. Wt.: 523.47
C, 45.89; H, 5.97; N, 5.35; O, 42.79
FIGURE 12
Structure VII
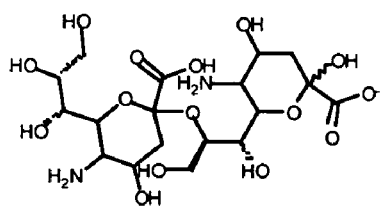
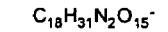
$C_{18}H_{31}N_2O_{15}^-$
Exact Mass: 515.17
Mol. Wt.: 515.44
C, 41.94; H, 6.06; N, 5.43; O, 46.56
FIGURE 13
Structure VI
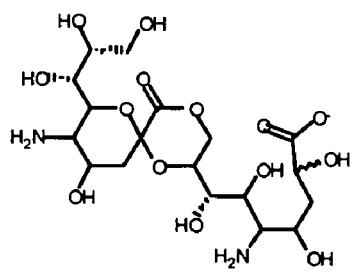
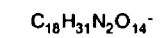
$C_{18}H_{31}N_2O_{14}^-$
Exact Mass: 499.18
Mol. Wt.: 499.44
C, 43.29; H, 6.26; N, 5.61; O, 44.85

Structure VII

$C_{18}H_{31}N_2O_{14}^-$
Exact Mass: 499.18
Mol. Wt.: 499.44
C, 43.29; H, 6.26; N, 5.61; O, 44.85

Structure VIII

$C_{18}H_{29}N_2O_{14}^-$
Exact Mass: 497.16
Mol. Wt.: 497.43
C, 43.46; H, 5.88; N, 5.63; O, 45.03

Exact Mass: 1000.5

Exact Mass: 944.47

Exact Mass: 1014.51

Exact Mass: 1000.5

Exact Mass: 1000.5

Exact Mass: 1000.5

Exact Mass: 1000.5

Exact Mass: 1000.5

Exact Mass: 1000.5

Exact Mass: 1016.53

Exact Mass: 1016.53

Exact Mass: 1016.53

Exact Mass: 944.47

Exact Mass: 944.47

Exact Mass: 944.47

Exact Mass: 958.48

Exact Mass: 958.48

Exact Mass: 958.48

Figure 34

Concentration for mAb binding to dodecylamine PS antigens as determined by direct binding ELISA[a,b]

| SEAM mAb | Non-reducing end NmB PS | | Non-reducing end dodecyl Re-N-Ac MBOS/PS | | | Non-reducing end dodecyl N-Pr MBOS/PS | | |
|---|---|---|---|---|---|---|---|---|
| | Dp>14 | | OS, Dp<7 | PS, Dp>14 | | OS, Dp<7 | PS, Dp>14 | |
| 2 | >10 | | >10 | >10 | | >10 | 0.94 | |
| 3 | >10 | | 0.05 | 0.05 | | 0.03 | 0.03 | |
| 12 | 0.52 | | 0.37 | 0.29 | | 0.11 | 0.01 | |
| 18 | >10 | | >10 | >10 | | 0.87 | 0.05 | |
| 35 | >10 | | >10 | >10 | | 5.73 | 0.5 | |

[a]Concentration of mAb in micrograms/ml required to give an OD$_{405}$ nm equal to 0.5 in 1 hr by ELISA with the non-reducing end dodecylamine NmB PSderivative coated on the plate and the bound mAb detected using goat anti-mouse IgG, M, A alkaline phosphatase conjugate secondary antibody as described in the text.
[b]Preparation and composition of NmB PSderivatives are as described in the text. Colominic acid was used to prepare this derivative. Since the colominic acid is from an E. coli K1 strain that does not O-acetylate the hydoxyl groups on C7 and C9, the polysaccharide is chemically identical to meningococcal group B polysaccharide (NmB PS). N-Pr, N-propionyl; N-Ac, N-acetyl; OS oligosaccharide; P

Figure 35

Concentration for mAb binding to BSA-PS derivative conjugate antigens as determined by direct binding ELISA[a,b]

| SEAM mAb | Non-reducing end NmB PS | Non-reducing end dodecyl Re-N-Ac MBOS/PS | | Non-reducing end dodecyl N-Pr MBOS/PS | |
|---|---|---|---|---|---|
| | Dp>14 | OS, Dp<7 | PS, Dp>14 | OS, Dp<7 | PS, Dp>14 |
| 2 | >10 | >10 | >10 | 4.6 | 3.8 |
| 3 | >10 | 0.012 | 0.014 | 0.018 | 0.016 |
| 12 | 0.52 | 0.18 | 0.14 | 0.01 | 0.02 |
| 18 | >10 | >10 | >10 | 0.07 | 0.007 |
| 35 | >10 | >10 | >10 | 33 | 0.23 |

[a] Concentration of mAb in micrograms/ml required to give an $OD_{405}$ nm equal to 0.5 in 1 hr by ELISA with the non-reducing end BSA NmB PS derivative coated on the plate and the bound mAb detected using goat anti-mouse IgG, M, A alkaline phosphatase conjugate secondary antibody as described in the text.
[b] Preparation and composition of NmB PSderivatives are as described in the text. Colominic acid was used to prepare this derivative. Since the colominic acid is from an *E. coli* K1 strain that does not O-acetylate the hydoxyl groups on C7 and C9, the polysaccharide is chemically identical to meningococcal group B polysaccharide (NmB PS). N-Pr, N-propionyl; N-Ac, N-acetyl; OS oligosaccharide; PS, polysaccharide; Dp, degree of polymerization.

Figure 37
A
B
C
D

Figure 40

| Tissue | Pathological diagnosis | SEAM 3 | IgG2b control |
|---|---|---|---|
| Brain | Glioblastoma | + | - |
| Brain | Atypical meningioma | +++ | - |
| Brain | Malignant ependymoma | ++ | - |
| Brain | Malignantoligodendroglioma | + | - |
| Ovary | Serous papillary adenocarcinoma | ++ | - |
| Ovary | Mucous papillaryadenocarcinoma | + | - |
| Pancreas | Islet cell carcinoma | +++ | - |
| Pancreas | Adenocarcinoma | + | - |
| Testis | embryonia carcinoma | + | - |
| Thyroid | Medullary carcinoma | + | - |
| Thyroid | Papillary carcinoma | ++ | - |
| Breast | Infiltrating ductal carcinoma | +++ | - |
| Spleen | Diffuse type b cell lymphoma | +/- | - |
| Lung | Small cell undifferentiated carcinoma | +/- | - |
| Lung | Squamous cell carcinoma | +++ | - |
| Lung | Adenocarcinoma | + | - |
| Esophagus | Squamous cell carcinoma | ++ | - |
| Esophagus | Adenocarcinoma | ++ | - |
| Stomach | Mucous adenocarcinoma | + | - |
| Intestine | Adenocarcinoma | ++ | - |
| Intestine | Moderate malignant mesenchymoma | +/- | - |
| Colon | Adenocarcinoma | ++ | - |
| Colon | Moderate malignant mesenchymoma | +/- | - |
| Liver | Hepatocellular carcinoma | ++ | - |
| Liver | Hepatoblastoma | + | - |
| Kidney | Clear cell carcinoma | +/- | - |
| Prostate | Adenocarcinoma | +++ | - |
| Prostate | Transitional cell carcinoma | + | - |
| Uterus | Leiomyoma | - | - |
| Uterus | Endometrial adenocarcinoma with squamous metaplasia | + | - |
| Uterine cervix | Adenocarcinoma | +++ | - |
| Striated muscle | Embryonic rhabdomyosarcoma of left leg | - | - |
| Rectum | Malignant melonoma of anus margin | +/- | - |
| Skin | Basal cell carcinoma of head | +++ | - |
| Striated muscle | Squamous cell carcinoma of left chest wall | +++ | - |
| Mediastinum | Neurofibroma | +++ | - |
| Retroperitoneum | Neuroblastoma | ++ | - |
| Abdominal cavity | Epithelial malignant mesotheliima of peritoneum | + | - |
| Lymph node | Diffuse type malignant lymphoma | ++ | - |
| Lymph node | Diffuse type b cell lymphoma | ++ | - |
| Lymph node | Hodgkin's lymphoma | +++ | - |
| Lymph node | Diffuse type non-hodgkin's lymphoma | +/- | - |
| Bladder | Transitional cell carcinoma | + | - |
| Bladder | Leiomyosarcoma | +++ | - |
| Bone | Osteosarcoma of rightt femur inferior extremity | + | - |
| Retroperitoneum | Spindle cell rhabdomyosarcoma of retroperitoneum | + | - |
| Smooth muscle | Leiomyosarcoma of left buttock | + | - |

Figure 51

Comparison of the genetic origin of variable regions of anti-NmB PS and anti-N-Pr NmB PS mAbs[a]

| Clone | Isotype | $V_H$ | $D_H$ | $J_H$ | $V_L$ | $J_K$ |
|---|---|---|---|---|---|---|
| 735 | IgG2a,κ | IGHV653*01 | IGHD-Q52*02 | IGHJ2*01 | IGKV1-110*02 | IGKJ5*01 |
| 2-2-B | IgM,κ | J558.2 | IGHD-SP2.7*01 | IGHJ2*01 | IGKV1-110*01 | IGKJ2*01 |
| SEAM 2 | IgG3,κ | IGHV1S4*01 | ND[b] | IGHJ2*01 | IGKV1-135*01 | IGKJ5*01 |
| SEAM 3 | IgG2b,κ | IGHV7S3*02 | IGHD-SP2.8*01/inv | IGHJ2*01 | IGKV1-135*01 | IGKJ5*01 |
| SEAM 12 | IgG2a,κ | IGHV13S1*01 | IGHD-ST4*01 | IGHJ2*01 | IGKV4-63*01 | IGKJ5*01 |
| SEAM 18[c] | IgG2b,κ | IGHV7S3*02 | IGHD-SP2.8*01/inv | IGHJ2*01 | IGKV4-74*01 | IGKJ2*01 |
| SEAM 35[b] | IgG2a,κ | IGHV7S3*02 | ND[b] | IGHJ4*01 | IGKV6-20*01 | IGKJ2*01 |

[a]Closest matches from either the IGMT or GenBank/EMBL databases. MAb 735 is from a hybridoma produced from a NZB mouse immunized with viable *N. meningitidis* group B strain ATCC 13090 (Frosch et al. (1985) Proc Natl Acad Sci U S A 82, 1194-8). Since only the amino acid sequences were reported (Klebert et al. Biol Chem Hoppe Seyler 374, 993-1000; Vaesen et al. (1991) Biol Chem Hoppe Seyler 372, 451-3), assignment of the germline genes for this mAb was based on the closest match (see Methods section). MAb 2-2-B was produced from a BALB/CJ mouse immunized with *N. meningitidis* group B strain P355. Germline assignments were based on the published DNA sequences (Berry et al. (2005) Mol Immunol 42, 335-44). The SEAM mAbs are from hybridomas prepared from CD1 mice immunized with N-Pr NmB PS tetanus toxoid conjugate (Granoff et al., 1998).
[b]ND, not determined since the segment was too short to enable identification of a specific gene.
[b]This mAb was previously listed as being IgG2b, but has subsequently been confirmed to be IgG2a. The subclasses of all of the other anti-N-Pr NmB PS mAbs used in this study were retested and confirmed as listed here and in (Granoff et al. (1998) J Immunol 160, 5028-36)

```
                                                                L-CDR1                                              L-CDR2
735       DVVMTQTPLSLPVSLGDQASISC RSSQSLVHSNGNTYLY WYLQKPGQSPKPLIY RVSNRFS    61
2-2-B     ELVMTQSPLSLPVSLGDQASISC RSSQSLVHSNGNTYLH WYLQKPGQSPKLLIY KVSNRFS    61
SEAM 2/3  DIVMTQSPLTLSVTIGQPASISC KSSQSLLHSNGKTYLN WLLQRPGQSPKLLIY LVSKLES    61
SEAM 35   DIVMTQSPISMSMSLGERVTLSC KAS-----ENVGTYVS WYQQKPEQSPKLLIS GASNRYT    56
SEAM 12   DIVMTQTTVIMSASPGEKVTMTC SASS---SVT---YMH WYQQKSRTSPKLWIY DTSKLAS    55
SEAM 18   DIVMTQTPTIMSASLGERVTMTC TASS---SVASSGYLH WYQQKPGSSPKLWIY GTSNLAS    58
                                                        L-CDR3
735       GVPDRFSGSGSGTDFTLKISRVEAEDLGVYFC FQGTHVPYT FGGGTRLEIKRA   114
2-2-B     GVPDRFSGSGSGTDFTLKISRVEAEDLGVYFC SQSTHVPYT FGGGTKLEIKRA   114
SEAM 2/3  GVPDRFSGSGSGTDFTLKISRVEAEDLGLYYC LQIIHFP HTFGAGTKLELKRA    114
SEAM 35   GVPDRFTGSGSGATDFTLTISSVQAEDLADYHC GQSYNYP YTFGGGTKLEIKRA   109
SEAM 12   GVPGRFSGSGSGNSYALTISSMEPEDVATYYC FQGSGYP LTFGAGTKLGLKRA    108
SEAM 18   GVPARFSGSGSGTSYSLTLSSVEAEDAATYYC HQYHRSH YTFGGGTKLEIKRA    111
```

V_H

```
                                               H-CDR1                                              H-CDR2
SEAM 3    EVKLQESGGGLVQPGDSLSLSCAAS GFTFTTPYYMG WVRQPPGKALEWLG YIRNKANGYTT    60
SEAM 18   EVQLEESGGGLVQPGDSLSLSCAAS GFTFTTPYYMG WVRQPPGKALEWLG YIRNKANGYTT    60
SEAM 35   EVKLEESGGGLVQPGGSLSLSCAAS GFTFTFTDYYLS WVRQPPGKALEWLG FIRNTANGYTT    60
SEAM 12   QVKLEQSGGGLVRPGNSLKLSCVTS GFTFINYRMH WLRQPPGKRLEWIA VITDNSDNYVV    60
735       QIQLQQSGPELVRPGASVKISCKAS GYTFTTDYIH WVKQRPGEGLEWIG WIYPGSGNTK-    59
2-2-B     EVQLQQSGPELVKPGASVKISCKAS GYSFTGYMH WVKQSHVKSLEWIG RINPYNGATS-    59
SEAM 2    EVQLEESGTELVKPGASVKLSCKAS GYTFTSYWMH WVKQRPGQLEWIG NINPTNGGIH-    59
                                                                 H-CDR3
SEAM 3    EYSASVKGRFTISRDNSQSILYLQMNALRAEDSATYYCAR Y-ARG-TVDS WGQGTTLTVS   118
SEAM 18   EYSASVKGRFTISRDNSQSILYLQMNALRAEDSATYYCAR Y-ARG-TVDS WGQGTTLTVS   118
SEAM 35   EYSASVKGRFTIARDNSQSILTLQMNALRAEDSATYYCAR W-SRR-AMDY WGQGTSVTVS   118
SEAM 12   NYAESVKGRFAISRDDSKSSVYLEMNRLREEDTATYFCSR S-RRS-FFDY WGQGTTLTVS   118
735       -YNEKFKGKATLTVDTSSSTAYMQLSSLTSEDSAVYFCAR --GKFAMDY WGQGTSVTVS   116
2-2-B     -YNQNFKDKASLTVDKSSSTAYMELHSLTSEDSAVYYCAR GDYGNSLFDY WGQGTTLTVS   118
SEAM 2    -FNEKFRTKAALTVDKSSSTAFLHLSSLTSEDSAVYYCAR R------GGY WGHGTTLTVS   112v
```

Figure 53: Nucleic Acid and Amino Acid Sequence of Variable Region of SEAM3 Heavy Chain Polypeptide (Open Reading Frame: nucleotides 1 - 330)

EVKLQESGGGLVQPGDSLSLSCAASGFTFTPYYMGWVRQPPGKALEWLGYIRNKANGYTTEYSASVKGRFTISRDNS
QSILYLQMNALRAEDSATYYCARYARGTVDSWG

```
  1 gaggtgaagc tgcaggagtc tggaggaggc ttggtacagc ctggggattc tctgagtctc
 61 tcctgtgcag cttctggatt caccttcact ccttactaca tgggctgggt ccgccagcct
121 ccagggaagg cacttgagtg gttgggttat attagaaaca aggctaatgg ttacacaaca
181 gagtacagtg catctgtgaa gggtcggttc accatctcca gagataattc ccaaagcatc
241 ctctatcttc aaatgaatgc cctgagagct gaggacagtg ccacttatta ctgtgcaaga
301 tatgcgaggg ggacggttga ctcctggggc
```

Figure 54: Nucleic Acid and Amino Acid Sequence of Variable Region of SEAM3 Light Chain Polypeptide (Open Reading Frame: 1 - 312)

DIVLTQSPLTLSVTIGQPASISCKSSQSLLHSNGKTYLNWLLQRPGQSPKLLIYLVSKLESGVPDRFSGSGSGTDFT
LKISRVEAEDLGLYYCLQIIHFPHTFG

```
  1 gatattgtgc tcacccagtc tccactcact ttgtcggtta ccattggaca accagcctcc
 61 atctcttgca aatcaagtca gagcctctta catagtaatg gaaagacata tttgaattgg
121 ttattacaga ggccaggcca gtctccaaag ctcctaatct atctggtgtc taaactggaa
181 tctggagtcc ctgacaggtt cagtggcagt ggatcaggga cagatttcac actgaaaatc
241 agcagagtgg aggctgagga tttgggactt tattactgct tgcaaataat acattttcct
301 cacacgttcg gt
```

Figure 55

Table: Comparison of assigned germline gene and amino acid sequences to respective expressed sequences for anti-NmB PS and anti-N-Pr NmB PS mAbs.[a]

| mAb | VL | | VH | |
|---|---|---|---|---|
| | Gene | Amino Acid | Gene | Amino Acid |
| 2-2-B[b] | 100 | 100 | 100 | 100 |
| 735[c] | unk[d] | >99 | unk[d] | 94.9 |
| SEAM 2 | 94.7 | 90.5 | 95.4 | 89.4 |
| SEAM 3 | 95.4 | 90.5 | 96.5 | 92.6 |
| SEAM 12 | 97.4 | 94.3 | 96.5 | 91.6 |
| SEAM 18 | 96.7 | 93.3 | 96.5 | 92.6 |
| SEAM 35 | 97.4 | 97.7 | 96.1 | 92.6 |

[a] Percent identity as calculated from pairwise CLUSTALW alignments. The sequence comparison does not include residues determined by the primers used to amplify and clone the gene sequences.
[b] From (Berry et al., 2005).
[c] From (Klebert et al., 1993; Vaesen et al., 1991).
[d] The gene sequences are unknown. The identification of germline sequence is based on comparison of the amino acid sequence with the sequences in the IMGT/V-QUEST database.

Alignment with FR-IMGT and CDR-IMGT delimitations

Figure 58

Alignment for D-GENE
3HCF        CGAGGG

Alignment for J-GENE
3HCF                    CGAGGGGGACGGTTGACTCCTGGGGCCAAGGCACCACTCTCCTCAGCCAAAACAACA

Translation of the JUNCTION
104                                                118
          C   A   R   Y   A   R   G   T   V   D   S   W   G   Q   G
3HCF    TGT GCA AGA TAT GCG AGG GGG ACG GTT GAC TCC TGG GGC CAA GGC

DE-N-ACETYL SIALIC ACID ANTIGENS, ANTIBODIES THERETO, AND METHODS OF USE IN CANCER THERAPY

CROSS-REFERENCE TO RELATED APPLICATION

This application claims priority benefit of U.S. provisional application Ser. No. 60/753,847, filed Dec. 23, 2005, and is a continuation-in-part of U.S. application Ser. No. 11/166,781, filed Jun. 23, 2005, which application claims priority benefit of U.S. provisional application Ser. No. 60/582,672, filed Jun. 23, 2004, which applications are each incorporated herein by reference in its entirety.

STATEMENT REGARDING FEDERALLY SPONSORED RESEARCH

This invention was made with government support under grants no. AI46464 and AI45642 awarded by the National Institute of Allergy and Infectious Diseases, and the National Institute of Health. The government has certain rights in this invention.

BACKGROUND OF THE INVENTION

In general, the goal of anti-cancer immunotherapy has been to identify stable antigens that are highly expressed but not shed or secreted from tumor cells, which antigens can then be used as the basis of immunotherapy, e.g., as the antigen in a cancer vaccine or as a target for antibody-based cancer therapy. Optimally, such tumor antigens would also be ones that elicit an immune response that is acceptably specific for the cancerous target cells, so as to reduce deleterious side effects that can result from cross-reactivity with non-cancerous cells of the subject being treated. Where cross-reactivity affects cells that can be repopulated, it may be acceptable to relax this requirement for the specificity of immunotherapy.

For example, although other antibodies are available for use in treating leukemias/lymphomas, the current standard for monoclonal antibody (mAb) therapy of non-Hodgkins lymphoma is RITUXIMAB™, a chimeric murine/human mAb that recognizes CD20 antigen. CD20 is highly expressed in most mature B cells and B-cell lymphomas, exhibits relatively slow modulation of expression or antigenic determinants, and is not shed or secreted. Although this antibody also binds CD20 on non-cancerous B cells, this cell population can be restored, e.g., through supportive treatment with immune enhancing therapeutics such as granulocyte-macrophage colony-stimulating factor (GM-CSF), erythropoietin (EPO), etc.

Fc regions of antibodies binding to cell surface antigens can mediate complement deposition and cell lysis (complement dependent cytotoxicity or CDC) or antibody-dependent cellular cytotoxicty (ADCC) by activating natural killer (NK) cells. Although not as common, antibodies can also be cytotoxic by binding to cell surface antigens that affect a signaling pathway leading to apoptosis. For example, although the mechanism of action of RITUXIMAB™ is not completely understood, it appears to exert its cytotoxic effects on CD20-positive tumor cells by a combination of antibody-dependent CDC, ADCC, and by activating cellular signaling pathways that lead to apoptosis. With the success of Rituximab, several other cellular antigens have been targeted with mAbs including CD22, CD30, and CD80.

In addition to passive immunotherapy through antibody administration, several active immunization strategies have also been explored. Exemplary cancer vaccines involve administration of a tumor antigen so as to elicit humoral antibody and/or cellular immune responses that are able to activate complement, and opsonophagocytotic killing of tumor cells. Exemplary vaccine compositions include those based on tumor cell lysates, and tumor-specific antigens (e.g., proteins, gangliosides (Tai, T., et al. Int J Cancer, 1985. 35:607-12), anti-idiotype immunoglobulin (Ig), etc. (Foon et a 1. J Clin Oncol, 2000. 18: 376-84) or peptide fragments of tumor-specific or overexpressed proteins that are derived from non-autologous and autologous cancers of the same type (Morioka et al. J Immunol, 1994. 153: 5650-8; Morioka, N., et al., Mol Immunol, 1995. 32: p. 573-81).

One limitation of these approaches has been that, although the target antigens are typically more highly expressed in tumor cells, they are nonetheless autoantigens and, thus, poorly immunogenic. Thus, cancer vaccines often employ various strategies for enhancing immunogenicity of the cancer antigen, e.g., combination with adjuvants, administration with a cytokine(s), linkage to to carrier proteins, and use in pulse-activation of mature dendritic cells in vitro. A more recent trend has been to develop more elaborate vaccination strategies that are tailored to the patient in which autologous dendritic cells are isolated, stimulated with tumor lysates or peptides and reinjected either alone or in combination with potent immunostimulatory cytokines (e.g., GM-CSF, interleukins IL-2 and IL-12, interferon gamma).

SUMMARY OF THE INVENTION

The present invention generally provides compositions methods and composition relating to the diagnosis and/or treatment of cancers having a cell surface de-N-acetylated sialic acid antigen, e.g., an at least partially de-N-acetylated ganglioside and/or a de-N-acetylated sialic acid-modified cell surface protein.

The disclosure provides various aspects of the invention. These include the following exemplary embodiments.

In one embodiment, methods of inhibiting growth of a cancerous cell are provided, which methods comprise administering to a subject a pharmaceutically acceptable formulation comprising an antibody that specifically binds a de-N-acetylated sialic acid (deNAc SA) epitope on an extracellularly accessible surface of a cancerous cell present in the subject, wherein administering facilitates reduction in viability of cancerous cells bound by the antibody. In related embodiments, the deNAc SA epitope is presented on a surface of the cancerous cell during cell division. In further related embodiments, the cancer is a melanoma, a leukemia, or a neuroblastoma. The antibody can be administered by infusion or by local injection, and can be administered prior, at the time of, or after surgical intervention to remove cancerous cells. The antibody can also be administered as part of a combination therapy, in which at least one of a cancer chemotherapy or a radiation therapy is administered to the subject.

In another embodiment, methods of inhibiting growth of a cancerous cell in a subject are provided which methods comprise administering to a subject a pharmaceutically acceptable formulation comprising an antibody that specifically binds a SEAM-3 reactive antigen on an extracellularly accessible surface of a cancerous cell present in the subject, wherein administering facilitates reduction in viability of cancerous cells bound by the antibody. In related embodiments, the SEAM 3 reactive antigen is presented on a surface of the cancerous cell during cell division. In further related embodiments, the cancer is a melanoma, a leukemia, or a neuroblastoma. The antibody can be administered by infusion or by local injection, and can be administered prior, at the time of, or after surgical intervention to remove cancerous cells. The antibody can also be administered as part of a combination therapy, in which at least one of a cancer chemotherapy or a radiation therapy is administered to the subject. In one related embodiment, the antibody is a SEAM 3 monoclonal antibody (ATCC Deposit No. HB-12170). In a further related embodiment, the SEAM 3 monoclonal antibody has been isolated using a high salt concentration step, in which a composition comprising a SEAM 3 monoclonal antibody is incubated in a high salt concentration solution under conditions suitable to facilitate separation of charged molecules from the SEAM 3 mAb in the solution. The SEAM 3 mAb is isolated from this solution, usually by removing precipitates and further isolating the mAb.

In another embodiment, methods of eliciting antibodies to a cancerous cell in a subject are provided, which methods comprise administering to a subject an immunogenic composition comprising a de-N-acetylated sialic acid (deNAc SA) antigen and an adjuvant, wherein the subject has or is suspected of having a cancer characterized by a de-N-acetylated sialic acid (deNAc'SA) antigen, where such administration is effective to elicit production of an antibody that specifically binds a deNAc SA epitope on an extracellularly accessible surface of a cancerous cell. In related embodiments, the cancer is a melanoma, lymphoma, or leukemia, or neuroblastoma. In further related embodiments, the deNAc SA antigen of the immunogenic composition is prepared by exosialidase treatment of deNAc SA antigen. In still further related embodiments, the deNAc SA antigen is a deNAc SA antigen conjugate, which can be, for example, a propionyl-linked or acetyl-linked deNAc SA antigen conjugate.

In another embodiment, methods of detecting a tumor in a subject are provided, which methods comprise contacting a biological sample obtained from a subject suspected of having cancer with an antibody that specifically binds a de-N-acetylated sialic acid (deNAc SA) epitope, where contacting is under conditions suitable for specific binding of the antibody to a deNAc SA epitope in the biological sample, the presence or absence of binding of the antibody is indicative of the presence or absence of cancerous cells having a cell surface deNAc SA epitope in the subject.

In another embodiment, methods of detecting a tumor in a subject are provided, the which methods comprise contacting a biological sample obtained from a subject suspected of having cancer with an antibody that specifically binds a SEAM 3 reactive antigen, said contacting being under conditions suitable for specific binding of the antibody to a SEAM 3 reactive antigen in the biological sample, where the presence or absence of binding of the antibody is indicative of the presence or absence of cancerous cells having a cell surface SEAM 3 reactive antigen in the subject. In related embodiment, the antibody is the SEAM 3 monoclonal antibody (ATCC Deposit No. HB-12170).

In another embodiment, methods of producing a polysaccharide (PS) derivative that is a suitable deNAc SA antigen are provided, which methods comprise culturing an *Escherichia coli* K1 bacterium in a growth medium comprising an N-acyl-mannosamine and an amine-protected mannosamine, wherein the bacterium is deficient in production of capsule polysaccharide in the absence of supplemental mannosamine, where the culturing provides for production of an amine-protected PS derivative having an amine protecting group and an N-acylated group. In related embodiments, method also includes treating the amine-protected PS derivative under conditions to remove the amine protecting group and couple the deprotected residue to a protein carrier to produce a conjugated PS derivative.

In another embodiment, methods of producing a deNAc SA antigen are provided, which methods comprise culturing a mammalian cell in a growth medium comprising an N-acyl-mannosamine and an amine-protected mannosamine, where the culturing provides for production of an amine-protected deNAc SA antigen having an amine protecting group and an N-acylated group on the surface of the mammalian cell. In related embodiments, the method also includes treating the amine protected deNAc SA antigen under conditions to remove the amine protecting group and couple the deprotected residue to a protein carrier to produce a conjugated deNAc SA antigen. Amine-protected deNAc SA antigens produced by this method are also provided, as are mammalian cells having a cell surface deNAc SA antigen produced by this method, and membrane and lipid extracts of such mammalian cells.

In another embodiment, methods of producing an immunogenic compositions are provided, which methods comprise contacting a composition comprising a de-N-acetylated sialic acid (deNAc SA) antigen with an exosialidase, said contacting being under conditions sufficient to provide for degradation of N-acylated sialic acid polymer contaminants in the composition, where the contacting produces a deNAc SA antigen-enriched composition. Compositions comprising deNAc SA antigen prepared by this exosialidase treatment method are also provided.

In another embodiment, methods of isolating an anti-deNAc SA epitope antibody and methods of isolating a SEAM 3 monoclonal antibody are provided, where such methods comprise incubating a composition comprising the antibody in a high salt concentration solution, said incubating being under conditions suitable to facilitate separation of charged molecules from the SEAM 3 mAb in the solution, and isolating the SEAM 3 mAb from the solution. Also provided are compositions comprising an anti-deNAc SA epitope antibody and a pharmaceutically acceptable carrier, where the antibody is isolated by this method. Also provided are compositions comprising a SEAM 3 monoclonal antibody and a pharmaceutically acceptable carrier, where the antibody is isolated by this method.

In another embodiment, isolated polynucleotides are provided, which polynucleotides comprise a nucleotide sequence encoding a light chain polypeptide comprising i) amino acid residues 24 to 39, ii) amino acid residues 55 to 61, and iii) amino acid residues 94 to 100 of a variable region of a SEAM 3 light chain polypeptide. In related embodiments, the encoded light chain polypeptide comprises the amino acid sequence of the variable region of a SEAM 3. light chain polypeptide. In further related embodiments, vectors and recombinant host cells containing such polynucleotides are provided.

In another embodiment, isolated polynucleotides are provided, which polynucleotides comprise a nucleotide sequence encoding a heavy chain polypeptide comprising i) amino acid residues 26 to 35, ii) amino acid residues 50 to 66, and iii) amino acid residues 101 to 108, of a variable region of a SEAM 3 heavy chain polypeptide. In related embodiments, the encoded heavy chain polypeptide comprises the heavy chain polypeptide comprises the amino acid sequence of the variable region of a SEAM 3 heavy chain polypeptide. In further related embodiments, vectors and recombinant host cells containing such polynucleotides are provided.

In another embodiment, antibody conjugates are provided, where the antibody conjugates comprise an antibody comprising antigen-binding portion of a SEAM 3 monoclonal antibody (ATCC Deposit No. HB-12170), and a covalently bound moiety, where the covalently bound moiety is a polyethylene glycol moiety, an anti-cancer drug, or an antigen-binding portion of an antibody. In related embodiments, the antibody of the conjugate is a SEAM 3 monoclonal antibody.

Other features of the invention will be readily apparent to the ordinarily skilled artisan upon reading the disclosure herein.

BRIEF DESCRIPTION OF THE DRAWINGS

FIG. 5 is a table summarizing the observed masses for each sample and theoretical masses of corresponding ions that are consistent with the observed masses.

FIGS. 6-15 provide structures of de-N-acetylated PS derivatives identified in FIG. 5.

FIG. 34 is a table summarizing the results of binding of the SEAM mAbs 2, 3, 12, 18 and 35 to dodecylamine NmB PS derivatives as measured by direct binding ELISA. The mAb SEAM 3 is described in U.S. Pat. No. 6,048,527.

FIG. 35 is a table summarizing the results of binding of the SEAM mAbs 2, 3, 12, 18 and 35 to BSA-NmB PS derivative conjugates as measured by direct binding ELISA. The mAb SEAM 3 is described in U.S. Pat. No. 6,048,527.

FIG. 37 is panel of photographs illustrating binding of SEAM 12 to NmB strain M7 in which the growth media was supplemented with N-acyl mannosamine derivatives as measured by fluorescence microscopy. Left panel: binding of SEAM 12 mAb to M7 supplemented with N-acetyl mannosamine; Left middle panel: binding of SEAM 12 to M7 without N-acyl mannosamine supplement; Right middle panel: binding of SEAM 12 mAb with N-trichloroacetyl mannosamine supplement; Right panel: binding of mAb SEAM 12 to the capsule PS containing N-trifluoroacetyl groups. The mAb SEAM 12 is described in U.S. Pat. No. 6,048,527.

FIG. 40 is a table summarizing the results of immunohistochemical analysis of SEAM 3 binding to a panel of human cancers.

FIG. 51 is a table showing a comparison of the genetic origin of variable regions of anti-MBPS and anti-N-Pr MBPS mAbs.

FIG. 52 is a schematic showing a comparison of $V_L$ and $V_H$ sequences for mAb 735 and SEAM mAbs. Boxed segments correspond to complementarity determining regions (CDR) loops. GenBank accession numbers: SEAM 2 VH, DQ113489 (SEQ ID NO:13); SEAM 2 VL, DQ113490 (SEQ ID NO:3); SEAM 3 VH, DQ113491 (SEQ ID NO:7); SEAM 3 VL, DQ113492 (SEQ ID NO:3); SEAM 12 VH, DQ113493 (SEQ ID NO:10); SEAM 12VL, DQ113494(SEQ ID NO:5); SEAM 18 VH, DQ113495 (SEQ ID NO:8); SEAM 18 VL, DQ113496 (SEQ ID NO:6); SEAM 35 VH, DQ113497 (SEQ ID NO:9); SEAM 35 VL, DQ113498 (SEQ ID NO:4). FIG. 52 also provides amino acid sequences of the mAbs 735 VL (SEQ ID NO:1); 735 VH (SEQ ID NO:11); 2-2-B VL (SEQ ID NO:2); and 2-2-B VH (SEQ ID NO:12).

FIG. 53 is a schematic showing the nucleic acid (SEQ ID NO:15) and amino acid sequences (SEQ ID NO:14) of the heavy chain polypeptide of SEAM3.

FIG. 54 is a schematic showing the nucleic acid (SEQ ID NO:17) and amino acid sequences (SEQ ID NO:16) of the light chain polypeptide of SEAM3.

FIG. 55 is a table showing a comparison of assigned germline gene and amino acid sequences to respective expressed sequences for anti-NmB PS and anti-N-Pr NmB PS mAbs.

FIG. 58 is a schematic showing the relationship of the DNA sequences of the SEAM3 heavy chain to variable region D and J (SEQ ID NO:20) chains as defined by International Immunogenetics Information System (IMGT) definitions (Lefranc et al. IMGT, the international ImMunoGeneTics information system®. Nucl. Acids Res., 2005, 33, D593-D597). The DNA (SEQ ID NO:22) and amino acid (SEQ ID NO:21) sequences of the DJ junction are also provided.

Figure 1:
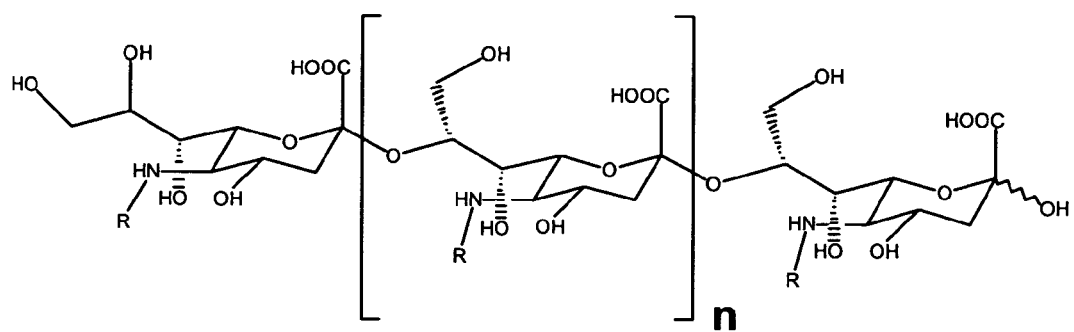
FIG. 1 provides the structure of NmB PS following de-N-acetylation according to the invention. R is H on most residues to provide a free amine (on a deacetylated group). In a small fraction of residues in the de-N-acetylated product, R may be $CH_3C=O$ (an acetyl group). "n" represents a number of sialic acid residues in the polymer, which may have the value of "n" in other formulae described herein.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The de-N-acetyl sialic acid (deNAc SA) antigen compositions disclosed herein are useful in cancer immunotherapy as well as in production of antibodies that can be used in antibody-based cancer chemotherapy. Accordingly, the disclosure provides deNAc SA antigens, as well as methods of their use in eliciting an anti-tumor immune response and/or enhancing an anti-tumor immune response, where the tumor contains cells having cell surface accessible deNAc SA antigen.

In general, deNAc SA antigens contain de-N-acetyl sialic acid residues that, following administration to a subject, can elicit antibodies that specifically bind deNAc SA epitopes on a cancer cell. In some embodiments, the deNAc SA antigen provide for an antibody response that has minimal cross-reactivity with self polysialic acid (PSA) antigens present on human tissues. The minimal deNAc SA epitope is a disaccharide of sialic acid residues in which one or both residues contain de-N-acetyl residues. The minimal deNAc SA epitope can also be described as a disaccharide unit comprising one or more sialic acid residues in which the N-acetyl group on the C-5 amino group has been removed leaving a free amine or, where one of the two residues are de-N-acetylated, the second residue contains an N-acetyl group (but, in some embodiments, not an N-propionyl group). The disaccharide unit defining this minimal epitope may be at the reducing end, the non-reducing end, or within a polymer of sialic acid residues (e.g., within a polysaccharide). De-N-acetylated residues in the context of PSA containing N-acylated residues are immunogenic and elicit antibodies that are reactive with the deNAc SA epitope, but are minimally reactive or not detectably reactive with human PSA antigens.

The de-N-acetylated NmB polysaccharide epitope was identified using a murine anti-N-Pr NmB polysaccharide mAb (monoclonal antibodies), SEAM 3, described in Granoff et al., 1998, J Immunol 160:5028 (anti-N-Pr NmB PS mAbs); U.S. Pat. No. 6,048,527 (anti-NmB antibodies); and U.S. Pat. No. 6,350,449 (anti-NmB antibodies).

The invention features deNAc SA epitopes, and formulations of such adapted for administration to a host to elicit an anti-deNAc SA epitope antibody response. The deNAc SA antigen compositions can be adapted for administration to a subject to elicit an anti-deNAc SA epitope immune response, particularly an anti-deNAc SA epitope antibody response, which immune response is directed against deNAc SA epitopes on a surface of certain cancerous cells, as discussed in detail below. The deNAc SA antigen compositions can also be used to generate antibodies that specifically bind a deNAc SA epitope on a surface of a cancerous cell (e.g., a deNAc ganglioside or deNAc sialic acid-modified surface accessible protein). Such antibodies are useful in antibody-based cancer therapy.

Other features of the invention are described herein, and will also be readily apparent to the ordinarily skilled artisan upon reading the present disclosure.

Definitions

Definitions provided herein shall control relative to those set out in the priority application.

The term "de-N-acetyl sialic acid antigen" (which may also be referred to as "de-N-acetylated sialic acid antigen" or "deNAc SA antigen") refers to a compound having or mimicking a deNAc sialic acid epitope (deNAc SA epitope), which epitope is minimally defined by a dimer of residues of sialic acid or sialic acid derivative, where the dimer contains at least one de-N-acetylated sialic acid residue adjacent an N-acylated (e.g., acetylated or propionylated) sialic acid residue or a sialic acid derivative residue. Examples of de-N-acetyl sialic acid antigens are provided in the present disclosure, and include, without limitation, de-N-acetylated polysaccharide derivatives ("PS derivatives"), de-N-acetylated gangliosides, and de-N-acetylated derivatives of a sialic-acid modified protein, particularly a sialic-acid modified Protein that is accessible at an extracellular surface of a mammalian cell, particularly a human cell, more particularly a cancer cell, particularly a human cancer cell. It should be noted that description of a deNAc SA antigen as a derivative of a starting molecule (e.g., PS derivative or ganglioside derivative) is not meant to be limiting as to the method of production of the de-N-acetyl sialic acid antigen, but rather is meant as a convenient way to describe the structure of the exemplary deNAc SA antigen.

"SEAM 3-reactive antigen" refers to an antigen having an epitope that is specifically bound by the monoclonal antibody (mAb) SEAM 3 (ATCC Deposit No. HB-12170). Exemplary SEAM 3-reactive antigens are provided in the working examples.

"Cell surface antigen" (or "cell surface epitope") refers to an antigen (or epitope) on surface of a cell that is extracellularly accessible at any cell cycle stage of the cell, including antigens that are predominantly or only extracellularlly accessible during cell division. "Extracellularly accessible" in this context refers to an antigen that can be bound by an antibody provided outside the cell without need for permeabilization of the cell membrane.

"PS" as used herein refers to polysaccharide, usually a capsular polysaccharide, particularly a capsular polysaccharide having one or more de-N-acetylated residues, including capsular polysaccharide of *N. meningitidis* or *Escherichia coli*, with *N. meningitidis* Group B and *E. coli* K1 being of particular interest. "NmB PS" as used herein refers to a PS of a Group B *N. meningitidis*. Reference to NmB PS throughout the specification is meant to be exemplary of PS structures amenable for production of compositions and use in methods of the invention.

"PS derivative" as used herein refers to a modified, usually chemically modified, polysaccharide (PS), particularly a PS of *Neisseria meningitidis* Group B (NmB) or *Escherichia coli* K1, with PS derivatives having a free amine (i.e., a primary amine) in lieu of one or more N-acetyl groups being of particular interest. In some embodiments, PS derivatives are NmB. In other other embodiments, the PS derivatives are biosynthetically produced ganglioside derivatives (e.g., produced in a mammalian cell, e.g., a cancerous mammalian cell). "PS derivative" as used herein includes protected PS derivativies, such as those described herein.

"de-N-acetylated PS derivative" as used herein refers to a PS derivative having one or more de-N-acetylated residues, e.g., one or more free amines at the C-5 position of one or more residues of the polysaccharide derivative. The term "de-N-acetylated PS derivative" is not meant to imply that de-N-acetylated PS derivatives are limited to PS derivatives generated by a process involving removing an acetyl group from a PS molecule, but instead, unless specifically indicated otherwise, is meant to encompass de-N-acetylated PS derivatives generated by any suitable method (e.g., by a biosynthetic method in which free amines are generated in a de-N-acetylated PS derivative by removal of a trihaloacyl protecting group incorporated into the PS molecule during PS biosynthesis). Further, "de-N-acetylated residue" is used herein in the context of a PS derivative to refer to a sialic acid residue in the molecule that has, in lieu of a native acetyl group, a primary amine.

"Free amine" and "primary amine" are used interchangeably herein to refer to an NH2 group, as in, for example, $RNH_2$ where "R" is a sialic acid residue of a PS derivative of the invention.

"deNAc SA antigen conjugate" refers to a deNAc SA antigen linked, usually covalently linked, to a carrier molecule (such as a carrier protein). Exemplary de-N-acetyl sialic acid antigen conjugates include a "PS conjugate", which generally refers to a conjugate of a carrier molecular (such as a carrier protein) and a homolinear polymer of alpha(2→8) N-acetyl neuraminic acid or any other polysaccharide containing this monomeric unit, or derivatives thereof, including de-N-acetylated PS derivatives of the invention. Of particular interest is a conjugate of a carrier protein and a derivative of *Neisseria meningitidis* capsular polysaccharide (particularly a Group B capsular polysaccharide), particularly a de-N-acetylated PS derivative of the invention. Also of particular interest is a conjugate of a carrier protein and a derivative of *E. coli* K1 capsular polysaccharide, particularly a de-N-acetylated PS derivative of the invention.

"Carrier" as used in the context of a carrier conjugated to a de-N-acetyl sialic acid antigen generally refers to a substance that, when linked to an antigen, serves as a T-dependent antigen which can activate and recruit T-cells and thereby augment T-cell dependent antibody production. The carrier need not be strongly immunogenic by itself, although strongly immunogenic carriers are within the scope of this invention. Carriers in this context are generally polypeptides, which can be all or a fragment of a protein.

"Conjugated" generally refers to a chemical linkage, either covalent or non-covalent, usually covalent, that proximally associates the de-N-acetylated PS with the carrier so that the carrier-conjugated de-N-acetyl sialic acid antigen has increased immunogenicity relative to unconjugated de-N-acetyl sialic acid antigen.

"Chemotherapy" as used herein refers to use of an agent (e.g., drug, antibody, etc.), particularly an agent(s) that is selectively destructive to a cancerous cell, in treatment of a disease, with treatment of cancer being of particular interest.

"Immunotherapy" refers to treatment of disease (e.g., cancer) by modulating an immune response to a disease antigen. In the context of the present application, immunotherapy refers to providing an anti-cancer immune response in a subject by administration of an antibody (e.g., a monoclonal antibody) and/or by administration of an antigen the elicits an anti-tumor antigen immune response in the subject.

"Treatment" or "treating" as used herein means any therapeutic intervention in a subject, usually a mammalian subject, generally a human subject, including: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells; and/or (iii) relief, that is, causing the regression of clinical symptoms.

The term "protective immunity" means that a vaccine or immunization schedule that is administered to a mammal induces an immune response that prevents, retards the development of, or reduces the severity of a disease (e.g., cancer), or diminishes or altogether eliminates the symptoms of the disease.

By "autoreactive" in the context of antibody binding is meant that the antibody exhibits significant binding to a host antigen (e.g., polysialic acid (PSA) native to a host). Autoreactive antibodies include those that bind to host antigens (e.g., PSA on non-cancerous host cells) as well as to foreign antigens (e.g., to a tumor antigen presented by a cancerous cell, to NmB PS or *E. coli* K1 PS). A "non-autoreactive antibody" is an antibody that does not significantly or detectably bind to a host antigen, with not detectable binding to a native host antigen being of particular interest. Non-autoreactive antibodies of interest are antibodies that specifically bind a de-N-acetyl sialic acid epitope (e.g., a deNAc SA epitope of a de-N-acetylated ganglioside of a cancer cell, a deNAc SA epitope of NmB PS or E. coli K1 PS), which antibodies can facilitate reduction of viability to a cell to which the antibody binds (e.g., are, bactericidal for NmB and/or E. coli K1 and/or facilitate reduction of cell viability of a cancer cell).

The phrase "in a sufficient amount to elicit an immune response" (e.g., to epitopes present in a preparation) means that there is a detectable difference between an immune response indicator measured before and after administration of a particular antigen preparation. Immune response indicators include but are not limited to: antibody titer or specificity, as detected by an assay such as enzyme-linked immunoassay (ELISA), flow cytometry, immunoprecipitation, Ouchter-Lowry immunodiffusion; binding detection assays of, for example, spot, Western blot or antigen arrays; cytotoxicity assays, and the like.

The term "antibody" (also used interchangeably with "immunoglobulin") encompasses polyclonal and monoclonal antibody preparations where the antibody may be of any class of interest (e.g., IgM, IgG, and subclasses thereof), as well as preparations including hybrid antibodies, altered antibodies, $F(ab')_2$ fragments, F(ab) molecules, Fv fragments, single chain fragment variable displayed on phage (scFv), single chain antibodies, single domain antibodies, chimeric antibodies, humanized antibodies, and functional fragments thereof which exhibit immunological binding properties of the parent antibody molecule. In some embodiments, e.g., cancer therapy, antibodies that provide for complement-mediated killing and/or antibody-dependent cellular cytotoxicity (ADCC) are of particular interest. The antibodies described herein may be detectably labeled, e.g., with a radio-isotope, an enzyme which generates a detectable product, a fluorescent protein, and the like. The antibodies may be further conjugated to other moieties, such as a cytotoxic molecule or other molecule (e.g., to provide for delivery of an anti-cancer drug to a cancer cell), members of specific binding pairs, e.g., biotin (member of biotin-avidin specific binding pair), and the like. The antibodies may also be bound to a support (e.g., a solid support), such as a polystyrene plate or bead, test strip, and the like.

Immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (usually of about 25 kDa or about 214 amino acids) comprise a variable region of about 110 amino acids at the $NH_2$-terminus and a kappa or lambda constant region at the COOH-terminus. Full-length immunoglobulin "heavy Chains" (of about 50 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991 and Lefranc et al. IMGT, the international ImMunoGeneTics information system®. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGTScientificChart/Numbering/IM-GTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

"Chimeric antibodies" refers to antibodies having light and/or heavy chain genes that have been constructed, typically by genetic engineering, from antibody variable and constant region genes belonging to different antibodies, e.g., of a different species. For example, the variable segments of the genes from a non-human (e.g., mouse) monoclonal antibody may be joined to human constant segments, such as gamma 1 and gamma 3. An example of a therapeutic chimeric antibody is a hybrid protein composed of the variable or antigen-binding domain from a non-human (e.g., mouse) antibody and the constant or effector domain from a human antibody, although other mammalian species may be used.

As used herein, the term "humanized antibody" or "humanized immunoglobulin" refers to an non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr.

A "variant" of a polypeptide, such as a variant antibody, is defined as a polypeptide that is altered by one or more amino acid residues relative to a reference sequence, e.g., a parent polypeptide, which may be a naturally occurring polypeptide. Such alterations include amino acid substitutions, deletions or insertions, or a combination thereof Variants of an antibody heavy chain or light chain polypeptide of interest are those retain their basic structural features and biological activity in binding to an antigen of interest and, in some embodiments, biological activity in effecting reduction of viability of a cancer cell.

Guidance in determining which and how many amino acid residues may be substituted, inserted or deleted may be found by comparing the sequence of a polypeptide to the sequence of a polypeptide with a related structure and function e.g., sequences from other sources (e.g., comparison between sequences from mammalian sources, e.g., human, rat, mouse, and the like).

The term "specific binding of an antibody" or "antigen-specific antibody" in the context of a characteristics of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody-antigen complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

The phrase "specifically binds to an antibody" or "specifically immunoreactive with" is also used when referring to an antigen such as a polysaccharide, phospholipid, protein or peptide, especially in the context of a binding reaction which is based on and/or is probative of the presence of the antigen under conditions which may also include a heterogeneous population of other molecules (e.g., as in a sample or in vivo). Thus, under the relevant conditions (e.g., designated immunoassay conditions), the specified antibody or antibodies bind(s) to a particular antigen or antigens and does not bind in a significant amount to other molecules present in the sample, particularly when compared to binding to an epitope of a target antigen against which the antibody was raised.

A "substitution" results from the replacement of one or more amino acids or nucleotides by different amino acids or nucleotides, respectively as compared to an amino acid sequence or polypeptide or nucleic acid. In the context of polypeptides, if a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: gly, ala; val, ile, leu; asp, glu; asn, gln; ser, thr; lys, arg; and phe, tyr.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide and polypeptide element amino acid or polynucleotide sequence, a deletion can involve deletion of about 2, about 5, about 10, up to about 20, up to about 30 or up to about 50 or more amino acids. A polypeptide according to the invention may contain more than one deletion.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition to one or more residues within a sequence of a polypeptide or nucleic acid, while "addition" can be an insertion or refer to amino acid residues added at the N- or C-termini of a polypeptide or to nucleotides added to the 5' or 3' ends of a nucleic acid. An insertion or addition may be of up to about 10, up to about 20, up to about 30 or up to about 50 or more amino acids.

"Corresponding amino acids", as will be exemplified below, are amino acid residues that are at an identical position (i.e., they lie across from each other) when two or more amino acid sequences are aligned. Methods for aligning and numbering antibody sequences are set forth in great detail in Chothia, supra, Kabat supra, and others. As is known in the art (see, e.g. Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected by the immune system of a multi-cellular organism, as opposed to unnaturally paired antibodies made by e.g. phage display, or humanized antibodies. As such, the subject parental antibodies do not usually contain any viral (e.g., bacteriophage M13)-derived sequences. Spleen, lymph nodes and bone marrow are examples of tissues that produce natural antibodies.

A "substitutable position", as in the context of variants of a given antibody heavy chain or light chain polypeptide, is a particular position of a polypeptide amino acid sequence that may be substituted by different amino acids, preferably without significantly decreasing the binding activity of the antibody. Methods for identifying substitutable positions, and how they may be substituted, are described in much greater detail below. A substitutable positions may also be referred to as "variation tolerant position".

A "parent" antibody, as will be described in greater detail below, is an antibody that is the template or target for amino acid modifications. In certain embodiments, amino acids may be "donated" by a "donor" antibody to the parent antibody to produce an altered antibody.

"Related antibodies", as will be described in greater detail below, are antibodies that have a similar sequence and produced by cells that have a common B cell ancestor. Such a B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies bind to the same epitope of an antigen and are typically very similar in sequence, particularly in their L3 and H3 CDRs. Both the H3 and L3 CDRs of related antibodies have an identical length and a near identical sequence (i.e., differ by 0, 1 or 2 residues). Related antibodies are related via a common antibody ancestor, the antibody produced in the naïve B cell ancestor. The term "related antibodies" is not intended to describe a group of antibodies that do not have a common antibody ancestor produced by a B-cell.

A "variable region" of a heavy or light antibody chain is an N-terminal mature domain of the chains. $V_H$ is the variable domain of an antibody heavy chain. $V_L$ is the variable domain of an antibody light chain, which could be of the kappa (K) or of the lambda isotype. K-1 antibodies have the kappa-1 isotype whereas K-2 antibodies have the kappa-2 isotype and $V_L$ is the variable lambda light chain.

As used herein, the term "monoclonal antibody" refers to an antibody composition having a homogeneous antibody population. The term is not limited by the manner in which it is made. The term encompasses whole immunoglobulin molecules, as well as Fab molecules, F(ab')$_2$ fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art and described more fully below.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

"Heterologous" as used in the context of a nucleic acid or polypeptide generally means that the nucleic acid or polypeptide is from a different origin (e.g., molecule of different sequence, different species origin, and the like) than that with which the nucleic acid or polypeptide is associated or joined, such that the nucleic acid or polypeptide is one that is not found in nature. For example, in a fusion protein, a light chain polypeptide and a reporter polypeptide (e.g., GFP) are said to be "heterologous" to one another. Similarly, a CDR from a mouse antibody and a constant region from a human antibody are said to be "heterologous" to one another.

By "isolated" is meant that a compound is separated from all or some of the components that accompany it in nature. "Isolated" also refers to the state of a compound separated from all or some of the components that accompany it during manufacture (e.g., chemical synthesis, recombinant expression, culture medium, and the like).

By "purified" is meant a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

"Enriched" means that a substance (e.g., antibody or antigen) in a composition is manipulated by an experimentalist or a clinician so that it is present in at least a two-fold greater concentration by weight, usually at least three-fold greater concentration by total weight, usually at least 10-fold greater concentration, more usually at least 100-fold greater concentration, and still more usually at least 1,000-fold greater concentration than the concentration of that antigen in the strain from which the antigen composition was obtained. Thus, for example, if the concentration of a particular antigen is 1 microgram per gram of total preparation (or of total protein), an enriched preparation would contain at least 3 micrograms per gram of total preparation (or of total protein).

"Inactivation" of a cell is used herein to indicate that the cell has been rendered incapable of cell division to form progeny. The cell may nonetheless be capable of response to stimulus and/or biosynthesis for a period of time, e.g., to provide for production of a cell surface molecule (e.g., cell surface protein or polysaccharide).

The term "immunologically naïve with respect to a deNAc SA antigen" denotes an individual (e.g., a mammal such as a human patient) that has not been exposed to de-N-acetyl sialic acid antigen described herein (e.g., a PS derivative), either alone or in the context of a larger molecule, in sufficient amounts to cause an immune response (e.g., to prime). If the individual has been exposed to a de-N-acetyl sialic acid antigen conjugate vaccine (in one or more doses), the individual has a propensity for production of antibodies.

A "primed" subject refers to a subject that has been exposed (e.g., by administration) to an antigen (e.g., a de-N-acetylated SA antigen) in a sufficient amount to elicit an immune response that, upon subsequent exposure to the same or second antigen (e.g., a de-N-acetyl sialic acid antigen conjugate), provides for a protective immune response.

By "no clinically relevant autoantibody response" is meant that production of autoantibodies is reduced by at least 25%, at least 40%, at least 50%, at least 60%, at least 75%, at least 80% or more using the immunization methods disclosed herein compared to autoantibody production following immunization of naïve subject with a conventional NmB polysaccharide vaccine (e.g., a PS conjugate vaccine as described in U.S. Pat. No. 4,727,136 (N-Pr-NmB conjugate vaccine)).

"Pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

"In combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same of different routes, and in the same or different dosage form type.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies. and diagnostics described herein, "subject" or "patient" is used interchangeably herein to refer to a subject having, suspected of having, or at risk of developing a tumor, where the cancer is one associated with cancerous cells having a de-N-acetyl sialic acid antigen at a cell surface (e.g., an at least partially de-N-acetylated ganglioside, de-N-acetylated sialic acid-modified protein). Samples obtained from such subject are likewise suitable for use in the methods of the invention.

As used herein; the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

DeNAc SA Antigens and Conjugates

De-N-acetyl sialic acid (deNAc SA) antigens of the present disclosure contain at least a minimal epitope of a dimer of residues of sialic acid or sialic acid derivative, where the dimer contains at least one de-N-acetyl sialic acid residue adjacent an N-acylated (e.g., acetylated or propionylated) sialic acid residue or a sialic acid derivative residue. This dimeric epitope, referred to herein as a deNAc SA epitope, can be positioned within any solvent accessible region of a de-N-acetyl sialic acid antigen. For example, where the deNAc SA antigen is positioned within a polymer (e.g., a polysaccharide), e.g., as in a de-N-acetylated PS derivative, the deNAc SA epitope can be positioned at the reducing end, the non-reducing end, or within the interior of the compound (e.g., 1, 2, 3, 4, 5, 10 or more residues from the reducing end or non-reducing end of the compound). The dimeric epitope can be present as one or more dimeric units within a deNAc SA antigen (e.g., as consecutive or nonconsecutive dimeric repeating units), or can be present within other units, present in the deNAc SA, e.g., within a trimeric unit, which may be present as consecutive or nonconsecutive repeating units). Exemplary molecules within the scope of the invention are set out in FIGS. 6-33.

It should be noted that all deNAc SA compounds described herein, including those having a bacterial PS or a ganglioside as a starting material or backbone, can be used in any of the immunization, therapeutic, and diagnostic methods described herein. Thus, for example, a deNAc SA antigen (e.g., generated using a NmB PS) can be used in the context of a cancer vaccine and used to raise antibodies that can be used in treatment or cancer. Likewise, a de-N-acetyl sialic acid antigen (e.g., such as one generated using a mammalian cell ganglioside) can be used in the context of a NmB vaccine and to detect NmB in a diagnostic.

deNAc SA antigens described herein, and useful in the methods of the invention, generally comprise at least one dimeric epitope, which can be present in a completely de-N-acetylated polysaccharide or an at least partially de-N-acetylated polysaccharide, and can be present in a homopolymeric or heteropolymeric molecule. For example, a deNAc SA antigen can comprise one or more structures as set out below (see, e.g., Formulae I-VIII below). deNAc SA antigens can comprise 2, 3, 4, 5, 6, 7, 8, 9,10, 11, 12, 13, 14, 15, 16, 17, 18, 19, 20, 25, 30, 35, 40, 45; 50, 55, 60 or more sialic acid residues or derivatives thereof, and may have a degree of polymerization (Dp) of about 2 to about 60, about 10 to about 50, about 30 to about 50, about 10 to 20, or about 12 to about 18, with a Dp, of about 2 to about 10 being of particular interest. deNAc SA antigens that are smaller in size can comprise further modifications (e.g., be conjugated to a carrier, lipidated, and the like) to provide molecules of suitable size and/or immunogenicity. DeNAc SA antigens can additionally comprise 3, 4, 5, 6, 7, 8, 9 or 10 or more adjacent de-N-acetylated residues, wherein in some embodiments, particularly where the deNAc SA antigen is composed of only N-acetylated and de-N-acetylated residues and is not further modified (e.g., by conjugation to a carrier or by modification of a sialic acid residue at the reducing end to contain a secondary alkyl amine), the de-N-acetylated residues of a deNAc SA antigen may be 30% or less of the total sialic acid residues of the molecule, and N-acetylated residues may be about 70% or more of the total sialic acid residues of the molecule. It should be noted that "de-N-acetylated" refers to any number of de-N-acetyl sialic acid residues in a polymer of sialic acid residues, provided the minimal deNAc SA epitope is present, and thus "de-N-acetylated" encompasses the term "at least partially de-N-acetylated".

DeNAc SA antigens of particular interest are those that, when administered to a subject elicit production of antibodies that bind a cancer cell that exhibits a deNAc SA epitope, are not significantly or detectably cross-reactive with PSA of the subject (e.g., human PSA found on non-cancerous cells). Anti-deNAc SA antigen antibodies are those that facilitate reduction of viability of a deNAc SA epitope-presenting cancer cell.

In general, deNAc SA antigens of interest are at least partially de-N-acylated, so that the deNAc SA antigens are zwitterionic compounds composed of, for example, polysaccharide residues or derivatives thereof, and comprise one or more dimers, and/or one or more trimers, which comprise an epitope as described above. The deNAc SA antigens, such as de-N-acetyl PS derivatives in general comprise at least one dimeric epitope, where the dimeric epitope is characterized by having (1) first and second de-N-acetylated residues; (2) a first N-acylated residue and a second adjacent de-N-acylated residue (i.e., a residue having a free amine group), where the N-acylated residue is not an N-propionyl (N-Pr) group; or (3) a first de-N-acylated residue (i.e., a residue having a free amine group) and a second adjacent N-acylated residue. In certain embodiments, the N-acylated residue comprises an unsaturated acyl group; in further embodiments, the N-acylated residue does not comprise an N-propionyl (N-Pr) group (i.e., the sialic acid residue in the dimer is not N-propionylated).

As used herein an "acyl group" includes a saturated or unsaturated acyl group, usually a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, or a saturated $C_{2-4}$ acyl group. A saturated acyl group as used herein is intended to refer to a carbonyl joined to a saturated alkyl group; an unsaturated acyl group as used herein is intended to refer to a carbonyl joined to an unsaturated alkyl group. In some embodiments, unsaturated acyl groups are of particular interest. The residues of the dimer can be a sialic acid or sialic acid derivative, such as a lactone or cyclic sialic acid.

Accordingly, the deNAc SA antigens comprise one or more de-N-acetylated residues of a sialic acid moiety or derivative thereof (e.g., a lactone, cyclic sialic acid, and the like), which de-N-acetylated residues can be positioned within the deNAc SA antigen at the reducing end, the non-reducing end, or within the interior of a polymer of sialic acid residues (i.e, between the reducing and non-reducing ends), with deNAc SA antigens having de-N-acetylated residues at the reducing end of the polysaccharide polymer being of particular interest.

The deNAc SA antigens may be provided as a structure comprising a single dimeric epitope, or a polymeric unit comprising two or more dimeric epitopes. DeNAc SA antigens may be homopolymeric or heteropolymeric structures, which can be composed of one or more of the structures below as well as, in some embodiments, additional de-N-acetylated or N-acetylated sialic acid residues. Where a formula is provided below with reference to "n" units (e.g., units of a dimeric or trimeric structure), the deNAc SA antigen can comprise multiple of such "n" units. For example, a deNAc SA antigen can comprise 2, 3, 4, 5, 6, 7, 8, 9 10 or more consecutive or non-consecutive units of a given dimeric or trimeric structure, where "n" refers to the number of consecutive dimeric or trimeric structures within each unit. Such dimeric and trimeric units can be separated by sialic residues.

The deNAc SA antigens can further comprise additional moieties attached to a sialic acid residue or derivative thereof at the non reducing terminus, reducing-terminus or both the non-reducing- and reducing-termini of the polysaccharide polymer.

In one embodiment, deNAc SA antigens include those comprising a structure represented by the formula:

FORMULA I 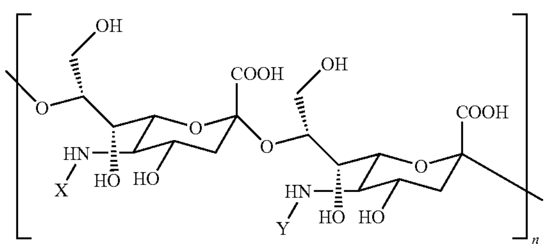 wherein

X and Y are independently H, an amine protecting group (e.g., a trihaloacyl group), or a saturated or unsaturated acyl group (usually a saturated acyl group), where in some embodiments, X and Y are independently 1) H or an amine protecting group; or 2) a saturated or unsaturated acyl group, and n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually 5 or greater, more usually about 10 or greater, and may have a degree of polymerization (Dp) of about 2 to about 60, about 10 to about 50, about 30 to about 50, about 10 to 20, or about 12 to about 18, with a Dp of about 2 to about 10 being of particular interest, and further wherein when X is a saturated or unsaturated acyl group (in some embodiments, other than a propionyl group and, in further embodiments, other than an unsaturated acyl group), Y is H or an amine protecting group; and when Y is a saturated or unsaturated acyl group (in some embodiments, other than a propionyl group and, in further embodiments, other than an unsaturated acyl group); X is H an amine protecting group. In another embodiment of particular interest, X and Y are independently H or a saturated or unsaturated acyl group, usually an unsaturated acyl group. In further embodiments, X and y are independently an amine protecting group (e.g., a trihaloacyl group) or a saturated or unsaturated acyl group, usually a saturated acyl group. In some embodiments, particularly where X or Y is H or an unsaturated acyl group, the PS derivative is less than 90%, usually less than 85%, or less than 80% N-acylated, particularly where the PS derivative comprises at least 10 or 20 residues.

In an embodiment of interest, X in Formula I is a saturated acyl group and Y is H or an amine protecting group. In an embodiment of particular interest, X in Formula I is an acetyl group and Y is H or an amine protecting group (e.g., a trihaloacyl group (e.g., a trihaloacetyl group)). In another embodiment of interest, X in Formula I is a saturated acyl group and Y is H; or X is an acetyl group and Y is H.

Where either X or Y are an amine protecting group (e.g., a trihaloacyl group), such deNAc SA antigens are referred to herein as "protected deNAc SA antigens" (e.g, "protected PS derivatives"), where the amine protecting group acts to prevent the amine group from undergoing a reaction during further modification of the protected deNAc SA antigen, e.g., conjugation of the molecule to a carrier (e.g., a carrier protein), addition of a lipid moiety (e.g., addition of an acyl amine at a non-reducing end of a protected PS derivative), and the like. The amine protecting group can subsequently be modified to provide a free amine at the residue. Protected deNAc SA antigens in general are exemplified by the structures described herein, where an amine protecting group is present at a variable position in lieu of a hydrogen. That is, where a hydrogen might be desired in a deNAc SA antigen to provide a free amine, protected DeNAc SA antigens contain an amine protecting group at that residue in lieu of the hydrogen of the free amine.

As used herein "amine protecting group" refers to a radical or group of atoms that is bound to an amine nitrogen atom of a molecule to prevent that nitrogen atom from participating in reactions occurring on other portions of the molecule. The term "amine-protected" denotes the structural characteristic of a molecule containing an amine nitrogen atom by which that nitrogen atom is prevented from participating in reactions occurring on other portions of the molecule.

Exemplary amine protecting groups for use in the invention include, but are not necessarily limited to, carbamates, amides, N-alkyl and N-aryl amines, imine derivatives, enamine derivatives, N-sulfonyls, and the like. Further exemplary amine protecting groups include, but are not necessarily limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

Further exemplary amine protecting groups of particular interest include trihaloacyl groups, such as trihaloacetyl and trihalopropionyl groups (e.g., trichloroacetyl, trifluoroacetyl, trichloropriopionyl, trifluoropriopionyl), and the like, with trihaloacetyl groups being of interest.

In one embodiment, the deNAc SA antigen comprising a structure of Formula I is conjugated to a carrier, e.g., by covalent attachment through a C2 ketone, a C6 aldehyde, C7 aldehyde, or C8 aldehyde as described below (e.g., C2-NH-carrier protein or C6-NH-carrier protein), where the carrier may be present at either the reducing or non-reducing end or both (e.g., through linkage to a residue at the reducing end of the derivative, to a residue at the non-reducing end of the derivative, or both). In another embodiment of particular interest, the deNAc SA antigen comprises at least one dimer of Formula I and comprises at the non-reducing end an N-acylated or de-N-acylated sialic acid residue substituted with an acyl amine (e.g., a saturated or unsaturated acyl amine, usually a saturated or unsaturated fatty acyl amine, usually a saturated acyl amine (e.g., $NHC_{2-18}$, $NHC_{2-12}$, $NHC_{2-10}$, $NHC_{2-8}$, $NHC_{4-12}$, and the like) (see, e.g., the moiety at the non-reducing end of Formulae IVa and IVb). These latter embodiments comprising a carrier and/or an acyl amine are of particular interest where the deNAc SA antigen comprises a structure of Formula I, wherein X is H and Y is an acetyl group, or where X is an acetyl group and Y is H. In another specific embodiment, where the deNAc SA antigen comprises a structure of Formula I, wherein X is H and Y is an acetyl group, or where X is an acetyl group and Y is H, the PS derivative is provided in combination with an adjuvant, as described below, where the PS derivative and adjuvant are usually provided in a pharmaceutically acceptable carrier (dry or aqueous diluent).

In one embodiment, the dimer is a disaccharide, where the disaccharide comprises one or more residues in which the N-acetyl group on the C-5 amino group has been removed or, where one of the two residues are de-N-acetylated, the second residue contains an N-acetyl group (but in some embodiments not an N-propionyl group). The disaccharide unit defining this minimal epitope may be at the reducing end, the non-reducing end, or within the polysaccharide. Where the deNAc SA antigen is provided as a disaccharide, the composition can have the structure:

FORMULA II

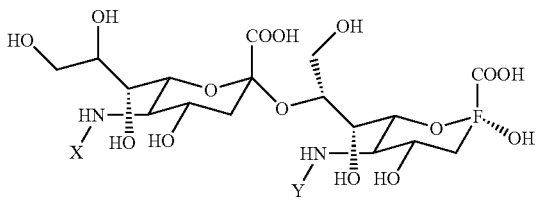

wherein X and Y are independently H, an amine protecting group (e.g., a trihaloacyl group), or a saturated or unsaturated acyl group; preferably further wherein when X is a acyl group (preferably other than a propionyl group), Y is H or an amine protecting group, and when Y is acyl group (preferably other than a propionyl group) X is H or an amine protecting group. In an embodiment of particular interest, X is an acetyl group and Y is H. Where X and/or Y are an amine protecting group, the compound is referred to herein as a protected deNAc SA antigen, where the protecting groups can be exploited as described above. Exemplary amine protecting groups are those described above. A deNAc SA antigen of Formula II can be further modified to include a carrier and/or an acyl amine, as described above for deNAc SA antigens of Formula I, particularly where X is H and Y is an acetyl group; or where X is an acetyl group and Y is H.

DeNAc SA antigens also include those comprising a structure represented by the formula:

FORMULA III

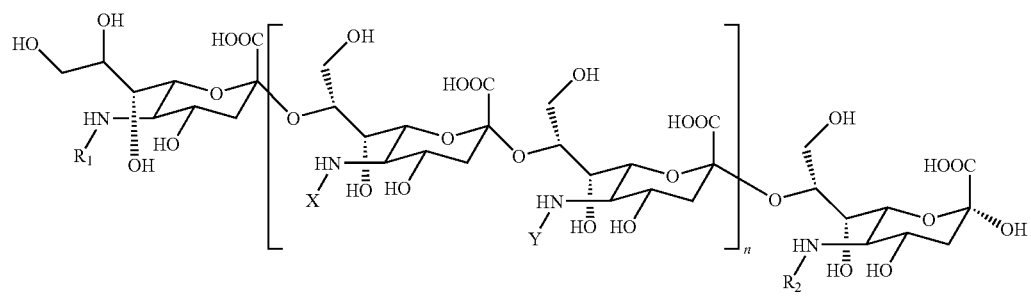

where X, Y, and n are as defined above, and $R_1$ and $R_2$ are independently H or an amine protecting group (e.g., a trihaloacyl group); or an acyl group (e.g., acetyl group) as described above. A deNAc SA antigen of Formula III can be further modified to include a carrier and/or an acyl amine, with modification of protected deNAc SA antigens being of interest, as described above for deNAc SA antigens of Formulae I and II, particularly where X is H and Y is an acetyl group and where X is an acetyl group and Y is H.

In another embodiment, the deNAc SA antigen comprises a structure represented by the formulae:

FORMULA IVa

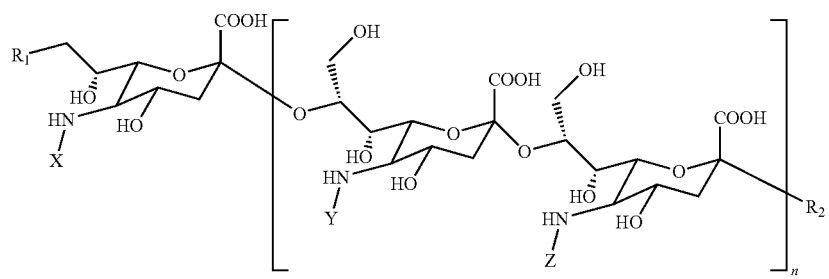

FORMULA IVb

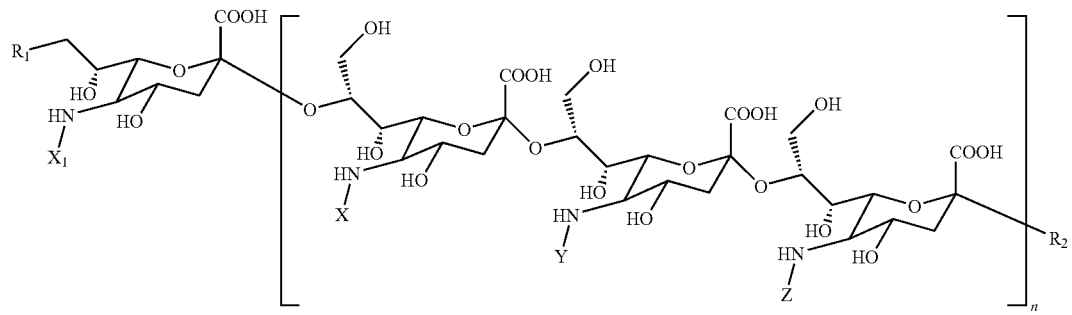

wherein $X_1$, X, Y and Z are H, an amine protecting group (e.g., a trihaloacyl group), or a saturated or unsaturated acyl group, usually an unsaturated acyl group, usually wherein $X_1$, X, Y, and Z are 1) H or an amine protecting group, or 2) a saturated or unsaturated acyl group (usually a saturated acyl group); with the proviso that at least one of X, Y, and Z is H or an amine protecting group; and at least one of X, Y, and Z is a saturated or unsaturated (usually saturated) acyl group; with embodiments of particular interest being those in which at least one of X, Y, and Z is H or a an amine protecting group; at least one of X, Y, and Z is an acetyl group, and at least, one of X, Y and Z is a propionyl group;

an amine protecting group), an acetyl group, and a propionyl group. In this embodiment, the PS derivative can have the structure of Formula V, wherein when X is H, Y and Z are different acyl groups and are either an acetyl group or a propionyl group; when X is an acetyl group, Y and Z are different moieties and are either H (or an amine protecting group) or a propionyl group; and when X is a propionyl group, Y and Z are different moieties and are either H (or an amine protecting group) or an acetyl group. Exemplary embodiments are set out in FIGS. 23-37.

In another embodiment, the deNAc SA antigens can be described as comprising at least one trimer having a structure represented by the formula:

FORMULA V

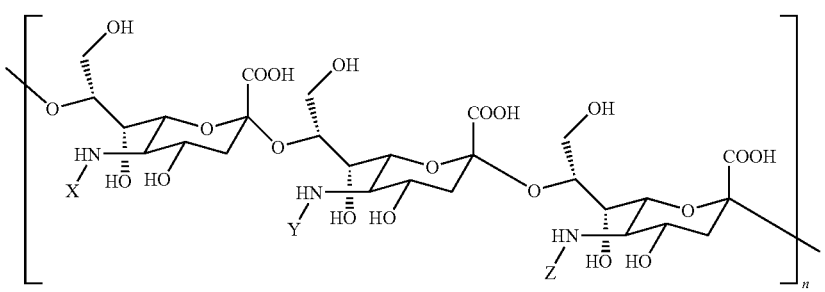

n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually 5 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest);

$R_1$ is a saturated or unsaturated acyl amine, usually a saturated or unsaturated fatty acyl amine, usually a saturated acyl amine (e.g., $NHC_{2-18}$, $NHC_{2-12}$, $NHC_{2-10}$, $NHC_{2-8}$, $NHC_{4-12}$, and the like); and $R_2$ is a hydroxyl or one or more acylated, amine protected (i.e., having an amine protecting group, e.g., trihaloacylated), or de-N-acetylated sialic acid residues as described herein. In one embodiment, $R_2$ is a polymer of de-N-acetylated sialic acid residues and acylated sialic acid residues (usually a sialic acid residue having a saturated N-acyl group, e.g, acetylated sialic acid residues, propionylated sialic acid residues, and the like).

In one embodiment, the deNAc SA antigens of Formula IVa and IVb comprises at least one of each of a free amine (or wherein X, Y and Z are independently H, an amine protecting group (e.g., a trihaloacyl group), or a saturated or unsaturated acyl group (usually a saturated acyl group); usually where X, Y and Z are independently 1) H or an amine protecting group, or 2) a saturated or unsaturated acyl group, usually a saturated acyl group; with the proviso that at least one of X, Y, and Z is H or an amine protecting group; and at least one of X, Y, and Z is a saturated or unsaturated acyl group, usually a saturated acyl group; with embodiments of particular interest being those in which at least one of X, Y, and Z is H or an amine protecting group; at least one of X, Y, and Z is an acetyl group; and at least one of X, Y and Z is a propionyl group;

n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually about 4 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest).

In one embodiment, the deNAc SA antigen has a mixed acyl structure wherein each trimer comprises at least one of each of a free amine, an acetyl group, and a propionyl group. In this embodiment, the deNAc SA antigen has the structure of Formula V, wherein when X is H, Y and Z are different acyl groups and are either an acetyl group or a propionyl group; when X is an acetyl group, Y and Z are different moieties and are either H or a propionyl group; and when X is a propionyl group, Y and Z are different moieties and are either H or an acetyl group.

DeNAc SA antigens include acyl derivatives having saturated or unsaturated, usually saturated, alkyl groups of $C_1$-$C_4$, usually $C_1$-$C_3$, including, for example acetyl, propionyl, isopropyl, butionyl, and the like. DeNAc SA antigens further include mixed acyl derivatives containing one or more de-N-acylated sites, where the deNAc SA antigens include different saturated or unsaturated, usually saturated, acyl groups.

DeNAc SA antigens further include those containing, a lactone moiety, a cyclic sialic acid moiety, or other sialic acid derivative in addition to or in lieu of one or more sialic acid moieties of a deNAc SA antigen described herein. For example, deNAc SA antigens having a lactone moiety can comprise the structure:

FORMULA VI

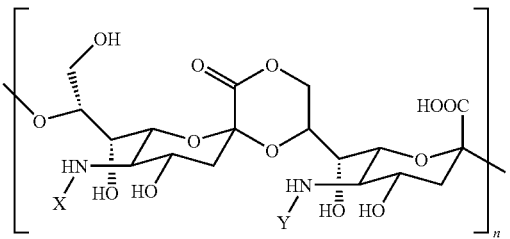

where X, Y and n are defined as above. DeNAc SA antigens having a lactone moiety can be present in a heteropolymer comprising one or more polymers (e.g, dimers, trimers) having a structure as described herein.

In another example, the deNAc SA antigen comprises a cyclic imine and/or reduced to a cyclic secondary amine moiety (e.g., 1-(4-Hydroxy-5-hydroxymethyl-pyrrolidin-2-yl)-ethanone) in lieu of a sialic acid moiety can comprise the structure:

FORMULA VII

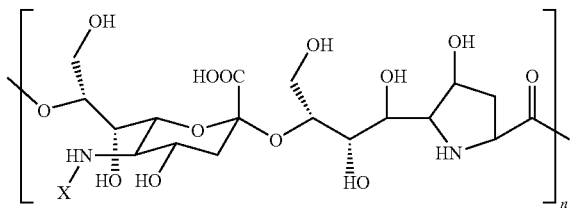

where X and n are defined as above. DeNAc SA antigens having a cycling imine or cyclic secondary amine moiety can be present in a heteropolymer comprising one or more polymers. (e.g, dimers, trimers) having a structure as described herein.

Where the deNAc SA antigen is provided as a single unit of the epitope (i.e., two residues as set out above, or three residues as described below), the deNAc SA antigen is normally covalently attached to a carrier (e.g:, a protein carrier). In general, and particularly where the deNAc SA antigen is a disaccharide (e.g., as shown in FIG. 11), trisaccharide, or other molecule of 3 or fewer residues, the deNAc SA antigen can be coupled through the C2 ketone or, after periodate treatment, the C6 aldehyde by reductive amination to a carrier protein (e.g., C2-NH-carrier protein or C6-NH-carrier protein). In other embodiments, the amine is coupled to aldehydes at C7, C6, and/or C8 (see, e.g., FIGS. 20-22), which likely is a result of incomplete oxidation. Coupling to C7 is most common, with coupling to C6 and C8 being less common.

DeNAc SA antigens further include those having one or more residues having attached lipid moieties (such as in described in U.S. Pat. No. 6,638,513). DeNAc SA antigens also include those having one or more residues having attached N-fatty acyl groups (e.g. N-lauroyl, N-oleoyl, and the like). Of particular interest are deNAc SA antigens in which N-fatty acyl-containing residues constitute, for example, 50% of sialic residues of a deNAc SA antigen sialic acid polymer or less such that the resulting deNAc SA antigens are still soluble in water. DeNAc SA antigens also include those having one or more amidated sialic acid residues, which residues have an alkyl secondary amine, usually at a non-reducing end of a polymer of a deNAc SA antigen. DeNAc SA antigens having one or more amidated sialic acid residues can be prepared by, for example, coupling fatty amines (e.g. dodecyl amine, oleoyl amine, and the like) to a C1 carboxyl group by nucleophilic substitution. Of particular interest are deNAc SA antigens in which such C1 amide derivatives constitute, for example, about 50% of residues or less of the deNAc SA antigen. DeNAc SA antigens further include those conjugated to a carrier at either the reducing or non-reducing end or both (e.g., through linkage to a residue at the reducing end of the derivative, to a residue at the non-reducing end of the derivative, or both).

The deNAc SA antigens can be homopolymers or heteropolymers of 2, 3, 4, 5, 6, 7, 8, 9, 10, 11, 12, 13, 14, 15, 16, 17, 18, 19, 20, 25, 30, 35, 40, 45, 50, 55, 60 or more dimeric epitope units (defining the minimal epitope) as described above, which dimeric units can be adjacent or separated by monomers or polymers of sialic acid residues or derivatives thereof. In some embodiments, the N-acylated residues of the deNAc SA antigen comprises represents less than 90%, less than 85%, less than 84%, less than 80%, less than 75%, less than 70%, less than 60%, or less than 55% of the total residues of the compound.

In other embodiments the ratio of de-N-acetylated residues to N-acylated residues is 1:1, 2:1, 3:1, 4:1, or 5:1 or more. In specific embodiments, the ratio of de-N-acetylated residues to N-acetylated residues is 1:1, 2:1, 3:1, 4:1, or 5:1 or more. In further specific embodiments, the ratio of de-N-acetylated residues to N-propionylated residues is 1:1, 2:1; 3:1, 4:1, or 5:1 or more. In other specific embodiments, the ratio of de-N-acetylated residues to. N-alkylated residues is 1:1, 2:1, 3:1, 4:1, or 5:1 or more. In another specific embodiment, the ratio of de-N-acetylated residues to N-acetylated residues is 1:1, 2:1, 3:1, 4:1, or 5:1 or more.

DeNAc SA antigens can be provided as a composition that is homogenous or heterogenous with respect to the deNAc SA antigen contained therein. For example, the invention contemplates compositions comprising deNAc SA antigens that are homogenous or heterogenous with respect to one or more of dimeric epitope structure, position of the dimeric epitope within the deNAc SA antigen, presence or absence of a conjugated carrier protein, Dp, molecular weight, ratio of de-N-acylated to N-acylated residues, degree of N-acylation (e.g., degree of N-acetylation or N-propionylation), and the like.

It will be understood that the deNAc SA antigens may be modified to provide a variety of desired attributes, e.g. improved pharmacological characteristics, while increasing or at least retaining substantially all of the antigenicity or immunogenicity of the unmodified deNAc SA antigen. For instance, a PS can be modified by extending, decreasing the number of residues in the polymer (e.g., so as to provide for differing degrees of polymerization (Dp)). By "Dp" is meant the number of residues of a polymer.

Substitutions with different residues, either naturally-occurring or non-naturally occurring, can also be made, e.g., as a result of chemical modification during de-N-acetylation, N-acylation, and the like. For example, the deNAc SA antigens described herein can be modified by a lipid moiety (as described in, for example, Examples 1 and 5 below, and in U.S. Pat. No. 6,638,513 (Seid)), conjugated to a carrier (e.g., at either the reducing or non-reducing end), and may comprise lactone, cyclic sialic acid, imine and reduced imine structures. In another example, the deNAc SA antigens can be modified by attachment of an N-fatty acyl groups (e.g. N-lauroyl, N-oleoyl, and the like). In further example, the deNAc SA antigens can include one or more sialic acid residue having an alkyl secondary amine (e.g., C1 amide derivatives), which can be prepared by, for example, coupling fatty amines (e.g. dodecyl amine, oleoyl amine, and the like) to a C1 keto group by nucleophilic substitution.

The deNAc SA antigen (e.g., de-N-acetylated PS) employed in the subject invention need not be identical to those disclosed in the Examples section below, so long as the subject de-N-acetylated PS are able to induce an immune response in a host that provides for production of antibodies that selectively bind N. meningitidis capsular polysaccharide, with little or no significant binding to host antigens (e.g., to host polysialic acid (PSA)). Thus, one of skill will recognize that a number of derivatives (described in more detail below), can be made without substantially affecting the activity of the de-N-acetylated PS.

Methods of Making De-N-Acetylated SA Antigens

As described below in more detail, the present disclosure provides methods for producing deNAc SA antigens. In one embodiment deNAc SA antigens are produced by chemical modification of a bacterial polysaccharide. In another embodiment, deNAc SA antigens are produced using a biosynthetic method involving culturing bacteria (*Neisseria meningitidis* group B or *Esherichia coli* K1) or a mammalian cell in the presence of a trihaloacetyl compound, followed by chemical modification of a PS derivative intermediate compound expressed on the cell surface. Each of these are described in more detail below.

Production of De-N-Acetylated SA Antigens Using Bacterial PS

In one embodiment, deNAc SA antigens can be produced by de-N-acetylation of a PS of *N. meningitidis* or *E. coli* K1, or other suitable source of bacterial PS, followed by partial re-N-acylation. Partial re-N-acylation provides for production of a de-N-acetylated PS derivative having fewer than 90%, fewer than 85%, fewer than 84%, fewer than 80%, fewer than 75%, fewer than 70%, fewer than 60%, or fewer than 55%, usually about 10%, about 15%, about 16%, about 20%, about 25%, about 30%, about 40%, or about 45% N-acylated residues relative to the total residues of the compound. In this regard, the invention provides for control of the level of acylation of the final product, so as to provide a de-N-acetylated PS having a desired level of acylation. In general, reacylation is controlled or prevented by limiting the amount of acylating reagent.

The deNAc SA antigens can also be produced also by de-N-acetylation of a PS of *N. meningitidis* or *E. coli* K1, or other suitable source of bacterial PS, followed by re-N-acylation with a mixture of amine protected group and acyl groups (e.g., trihaloacetyl and acetyl groups) in a desired ratio such that the PS derivative contains fewer than 90%, fewer than 85%, fewer than 84%, fewer than 80%, fewer than 75%, fewer than 70%, fewer than 60%, fewer than 55% amine protected residues, usually about 10%, about 15%, about 16%, about 20%, about 25%, about 30%, about 40%, or about 45% amine protected residues (e.g., N-trihaloacylated residues) relative to the total residues of the compound (where the compound generally contains at least 10 or at least 20 residues). The level of acylation of the final product after removal of the amine protecting group can be controlled to reduce undesirable side reactions with free amino groups, so as to provide a deNAc SA antigen having a desired level of acylation. Removal of the amine protecting groups for a free amine at the deprotected residue. In general, the proportion of de-N-acetyl residues is controlled by limiting the amount of amine protecting reagent (e.g, the amount of a trihaloacylting reagent).

DeNAc SA antigens can also be produced by biosynthesis of a PS of *N. meningitidis* or *E. coli* K1, or other suitable source of bacterial PS, in which the bacterial growth media is supplemented with a mixture of an amine-protected mannosamine (e.g., N-trihaloacyl mannosamine) and acyl mannosamine (e.g., N-trihaloacetyl and N-acetyl mannosame) in a desired ratio such that the deNAc SA antigen expressed by the bacteria contains fewer than 90%, fewer than 85%, fewer than 84%, fewer than 80%, fewer than 75%, fewer than 70%, fewer than 60%, or fewer than 55% amine-protected (e.g., N-trihalo acylated) residues relative to the total residues of the PS produced. The level of acylation of the final product after removal of the amine protecting group is controlled to reduce undesirable side reactions with free amino groups, so as to provide a deNAc SA antigen having a desired level of acylation. In general, the proportion of de-N-acetyl residues is controlled by limiting the amount of amine-protected mannosamine reagent (e.g., N-trihalo acetyl mannosamine).

PS, including NmB PS and *E. coli* K1, are exemplary molecules suitable for use in the PS derivatives and conjugates and other molecules in the invention, and such starting materials are known in the art, as are methods for their isolation and conjugation to a carrier.

DeNAc SA antigens can be generated through any conventional means suitable. For example, in one embodiment, deNAc SA antigens can be produced by de-N-acetylation of a PS, which can be accomplished by contacting a native PS with a basic aqueous medium at elevated temperatures; for example about 90° C. to about 110° C., and at a pH of about 13 to about 14 (e.g., in sodium hydroxide about 2M concentration). Alternatively, hydrazine in aqueous solution may be used. The degree of N-deacetylation at this stage may vary, with at least about 85%, about 90%, about 95%, or about 99% up to about 100% de-N-acetylation being of interest. The de-N-acetylated product can be recovered by, for example, cooling, neutralizing, purification if desired, and lyophilization.

The non-aqueous and biosynthetic production methods are described in more detail below, as well as in the Examples.

Non-Aqueous Production Methods

In one embodiment, de-N-acetyl sialic acid antigens can be produced through chemical modification of a PS in a polar protic organic solvent containing less than 5% water. Aqueous solution-based methods used to prepare NmB PS derivatives (as in, for example, Example 1) produce relatively small amounts of material that is reactive with protective non-autoreactive mAbs (e.g. SEAM 2,3). Without being held to theory, this low yield results from one or more of the failure to remove all N-acetyl groups as described above, the failure to quantitatively control the amount of re-N-acylation because of poor reactivity of the PS amino groups (intramolecular COO$^-$ and NH$_3^+$ charge pairing), competing hydrolysis of the acylating reagent, and/or oxidation of the amino group by periodate when preparing non-reducing end aldehydes.

Performing acylation of PS in a polar protic organic solvent, and, where desired, in the presence of a small amount of water (e.g., formamide, mixed formamide/2.5% water, and the like), protecting amino groups (e.g., with a trihaloacyl (e.g., trichloroacetyl or trifluoroacetyl)amide) which is later removed to generate predictable fractions of de-N-acetyl residues, and use of a strong base (e.g., sodium hydroxide or methoxide) during the acylation step to ensure amino group reactivity provides for improved yields and better control of the fraction of residues that a de-N-acetylated).

The organic solvent can be any suitable solvent, usually a polar protic or aprotic organic solvent. Exemplary such solvents include formamide, dimethylformamide, mixed formamide/dimethlformamide, and the like or mixtures of organic solvent and a small percent of water (typically at least about 2% or 2.5% water, but usually less than 10%, less than 5%). Water is added as necessary to ensure solubility of the components, particularly of the PS.

The amine groups of the molecule are protected by modifying them with a suitable amine protecting group. Exemplary amine protecting groups are described above, and include, without limitation, a carbamate or amide, including N-alkyl and N-aryl amines, imine derivatives, enamine derivatives, N-sulfonyl, and the like. In one embodiment of particular interest, the amine protecting groups is a trihaloacyl amide, usually trihaloacyl groups of $C_2$-$C_{12}$, more usually $C_2$-$C_{10}$, more usually $C_2$-$C_8$, more usually $C_2$-$C_6$, most usually a trihaloacetyl or trihalopropionyl, protecting group. Such protecting groups can be selected for stability at pH 8 or lower, stability in the presence of periodate, and/or ease of removal as described below. In general, amine protecting group prevents N-oxidation in the presence of periodate. The form of the deNAc SA antigen produced after this protecting step is referred to herein as the "protected deNAc SA antigen", "protected acylated deNAc SA antigen", "protected PS derivative" or "protected acylated PS derivative", wherein the compound comprises one or more amine protecting groups (e.g., trihaloacyl-protected amine groups).

In general, production of a protected deNAc SA antigen is accomplished by contacting an at least partially de-N-acetylated PS molecule with an amine protecting group reagent and an acylating reagent in the presence of an organic solvent as described above. The amine protecting reagent can be, for example, a trihaloacylating reagent, e.g., trihaloaccetic anhydride or alkyl trihaloacetic esters being of particular interest (e.g., trichloroacetic anhydride, trifluoroacetic anhydride, ethyl trifluoroacetyl ester, or ethyl trichloroacetyl ester, and the like). Acylating reagents provide an activated acyl group, wherein the activated acyl group is usually an acetyl group or propionyl group, more usually an acetyl group. In some embodiments, the trihaloacylating reagent and acylating reagents are contacted with the de-N-acetylated PS molecule as a mixture.

The relative amounts of trihaloacylating reagent and acylating reagent in the mixture are provided so that the end product of the protecting step contains the desired ratio of trihaloacylated residues and acylated residues, wherein the trihaloacylated groups will generally be removed to provide a free amine in the final product. For example, where the ratio of free amines to acylated residues in the final deNAc SA antigen product is to be about 1:10, 1:4, or 1:1, the ratio of trihaloacylating reagent to acylating reagent is about is present in the mixture at a ratio of about 1:10, 1:4, or 1:1.

Stated differently, the amount of trihaloacylating reagent in the mixture is roughly equal to the fraction of de-N-acetyl groups desired in the final deNAc SA antigen product after deprotection (e.g., 10%, 25%, 50%, and the like). The acylating reagent can also be provided as a mixture of different activated acyl groups (e.g., acetyl, propionyl) so as to provide for a desired ratio of differently acylated groups in the PS derivative. For example, where the deNAc SA antigen is to have a ratio of acetylated residues to propionylated residues of 2:1 or 1;1, the acylating agents for activated acetyl and propionyl groups is provided in the same or similar ratio in the acylating agent mixture.

After the protecting step, the protected deNAc SA antigen can then be modified as desired, e.g., by conjugation to a desired carrier, e.g, by perioidiation followed by reductive amination. The protecting groups can then be removed (e.g. by hydrolysis or reduction) to leave a free amine, thus providing the final deNAc SA antigen. The amine protecting groups can be removed by either hydrolysis using a strong aqueous base (e.g., pH 9 or greater), by reduction (e.g., with sodium borohydride), or by the amine added during the preparation of conjugates by reductive amination (see, e.g., Example 5). The deNAc SA antigen can then be isolated according to methods well known in the art.

The nonaqueous production methods can be desirable for a number of different reasons. First, performing the acylation reactions in an organic solvent provides greater flexibility in the type of acyl groups that can be used. For example, the use of an organic solvent facilitates use of fatty acyl groups of greater than 4 carbons which can pose challenges with respect to solubility in aqueous systems, as well as highly reactive activated acyl groups (e.g., trifluoroacetyl and trichloroacetyl). The reaction in organic solvent also provides greater control over the degree of acylation, since there is no or minimal competing reaction with water and OH$^-$ to deplete the reagent. As a result, the acylation reactions with the polysaccharide can be designed so that they proceed to completion.

The non-aqueous approach also allows the use of protected amine groups. When left unprotected, the polysaccharide amine groups may participate in other undesired reactions such as oxidation in the presence of periodate and intramolecular reactions with activated carboxyl groups, or with aldehydes introduced at the non-reducing end and the reducing end ketone. Trifluoroacetyl or trichloroacetyl are preferred protecting groups since they are stable at pH less than about 8, stable in the presence of periodate, and can easily be removed in aqueous base or by reduction with sodium borohydride to produce deNAc SA antigen containing de-N-acetyl residues where the percentage of de-N-acetyl residues is controlled by the amount of amine derivatized with protecting groups.

Biosynthetic Methods of deNAc SA Antigen Production Using Bacteria

In another embodiment, deNAc SA antigens are generated by culturing *N. meningitidis* bacteria, particularly Group B bacteria, in the presence of one or more N-acyl mannosamine derivatives and under conditions to promote production of deNAc SA antigen having N-acyl sialic acid residues. This can be accomplished by including n the bacterial culture medium a mannosamine derivative having a desired N-acyl group.

In one embodiment, the N-acyl mannosamine derivative is a mannosamine comprising an amine protecting group (a "protected mannosamine" or "amine protected mannosamine"), exemplified herein by N-trihaloacyl mannosamines, to accomplish "feeding of the mannosamine derivative to the bacteria. Exemplary amine protected mannosamines suitable for use in the invention include any amine protected mannosamine that can incorporated into the bacterium's PS synthetic pathway to provide for production of a protected deNAc SA antigen. Exemplary amine protected mannosamine reagents include N-trihaloacyl mannosamine, e.g., N-trihaloacetyl mannosamine (e.g., N-trichloroacetyl mannosamine, trifluoroacetyl mannosamine), N-formyl mannosamine, and the like). In addition to the amine-protected mannosamine, the culture medium generally also includes an N-acetyl mannosamine, to provide for a deNAc SA antigen having both protected sialic acid residues and N-acetylated sialic acid residues.

Without being held to theory, when cultured in the presence of the amine protected mannosamine, bacterial enzymes involved in capsule biosynthesis incorporate the amine protected mannosamine into sialic acid, which is then incorporated into capsule polysaccharide. Standard fermentation and purification methods can be used to generate a protected deNAc SA antigen containing a desired fraction of monomers having attached protecting groups. The deNAc SA antigen containing these protecting groups can be of the structures described above, for example.

In a related embodiment, where a deNAc SA antigen having mixed N-acyl sialic acid residues is desired, the culture medium includes mixed N-acyl-mannosamine reagents. For example, the N-acyl mannosamine can comprise saturated or unsaturated acyl groups, usually saturated acyl groups, of from $C_1$-$C_5$, more usually $C_2$-$C_5$, more usually $C_2$-$C_4$, more usually $C_2$-$C_3$, with acetyl or propionyl groups being of particular interest. Culturing the bacteria in the presence of such mixed N-acyl mannosamine reagents can provide for production of a deNAc SA antigen having mixed N-acyl sialic acid residues, e.g,. N-acetyl sialic acid, N-propionyl sialic acid, and the like. In one embodiment of particular interest, the bacteria is cultured in the presence of a mixture of a protected mannosamine (e.g., a N-trihaloacyl mannosamine) and N-acyl mannosamines (e.g, a mixture of N-acetyl mannosamine and N-propionyl mannosamine).

In one embodiment, a *N. meningitids* bacteria, preferably a Group B strain, is cultured in the presence of a mixture of an N-acyl mannosamine (e.g., N-acetyl mannosamine) and a N-trihaloacyl mannosamine. In other embodiments, the bacteria is a non-encapulated strain, and can be a strain that is defective in PS capsule synthesis in the absence of supplemental N-acetyl mannosamine in the culture medium (e.g., due to a defect in one or more enzymes such that the bacteria cannot synthesize capsule PS unless the growth media is supplemented with N-acetyl mannosamine). For example, the strain can be defective in an N-acetyl-D-glucosamine-6-phosphate 2 epimerase, such as in the NmB strain M7.

The relative amounts of mannosamine reagents in the culture (e.g., the ratio of N-trihaloacyl mannosamine and N-acetyl mannosamine) are provided so that the biosynthetic end product contains the desired ratio of different sialic acid residues and/or derivatives in the deNAc SA antigen (e.g., trihaloacylated residues and acylated residues on the deNAc SA antigen). In general, the protecting groups (e.g, the trihaloacylated groups) are removed to provide a free amine in the final deNAc SA antigen product. For example, where the ratio of free amines to acylated residues in the final deNAc SA antigen product is to be about 1:10, 1:4, or 1:1, the ratio of N-trihaloacyl mannosamine to mannosamine is about 1:10, 1:4, or 1:1. Stated differently, the amount of N-trihaloacyl mannosamine in the culture is roughly equal to the fraction of de-N-acetyl sialic acid groups desired in the final deNAc SA antigen product after deprotection (e.g., 10%, 25%, 50%, and the like).

Similarly, the relative amounts of "unprotected" N-acyl mannosamines (mannosamines that do not contain an amine protecting group, but which can comprise, for example, an acetyl or proprionyl group as the N-acyl group) in the culture can be provided so as to provide for a desired ratio of differently acylated sialic acid residues in the deNAc SA antigen. For example, where the deNAc SA antigen is to have a ratio of acetylated residues to propionylated residues of 2:1 or 1;1, N-acetyl mannosamine and N-propionyl mannosamine is provided in the same or similar ratio in the culture.

The deNAc SA antigens can then isolated from the bacteria using methods known in the art. Where the deNAc SA antigen contains an amine protecting group, such deNAc SA antigen are especially suitable for generating a deNAc SA antigen having further modification, e.g., a conjugate (e.g,. by periodate oxidation of the non-reducing end) or modifying a sialic acid residue to provide an alkyl secondary amine, particularly a C1 amide, at a non-reducing end of the polymer (polysaccharide). After modification is completed, the trihaloacyl protecting groups can be removed as described above. For example, the protecting groups can be removed by reductive amination (e.g., with sodium cyanoborohydride) or further reduction (e.g., with sodium borohydride or treatment with base at pH 9 or greater) to provide a free amine.

Fragments, Re-Acylation, and Other Modifications

Where the deNAc SA antigen is produced by chemical modification of PS, fragments of PS are usually produced as a result of N-deacetylation, which fragments generally have an average molecular weight ranging from about 3,000 to about 50,000 Daltons. While the invention contemplates deNAc SA antigen that are full-length derivatives of PS as well as fragments, deNAc SA antigens of PS fragments are also contemplated.

Where desired, re-acylation to provide the deNAc SA antigen can be carried out by resuspending de-N-acetylated PS in an aqueous medium of about pH 8 to 9 (e.g., in sodium hydroxide), followed by addition of an appropriate acyl anhydride. In one embodiment, both the polysaccharide and acylating agent (e.g. acetyl anhydride or propionic anhydride) are provided in an organic solvent/water mixture (e.g., 2% (vol./vol.) water in formamide or dimethylformamide). This embodiment in particular provides for more controlled levels of reacylation. The method of the invention involves use of less than 1 molar equivalent, less than 0.75 mole equivalent, less than 0.5 mole equivalent, less than 0.25 mole equivalent, less than 0.1 mole equivalent, less than 0.05 mole equivalent, less than 0.025 mole equivalent, or as little as 0.02 mole equivalent of acid anhydride or acylating agent (e.g. acyl-active ester such as O-acyl hydroxysuccinimide).

O-acyl groups can be removed by increasing the pH to about 12. The pH is then lowered to about 8 (e.g., by addition of hydrochloric acid), and the derivative purified as desired, e.g., by dialysis. The reaction products can be further purified and lyophilized as desired.

The degree of N-acylation of the resulting deNAc SA antigen is generally less than 90%, less than 85%, less than 84%, less than 80%, less than 75%, less than 70%, less than 60%, or less than 55%, usually greater than 10%, 15%, 16%, 25%, 30%, 40%, or 45%. The molecular weight of the polysaccharide of the deNAc SA antigen can vary, with deNAc SA antigens produced from PS generally ranging in molecular weight from about 0.5 kDa (e.g., a disaccharide) to 80 kDa, about 1 kDa to about 70 kDa, about 2 kDa to about,60 kDa, about 3 kDa to about 50 kDa, about 5 kDa to about 25 kDa, about 10 kDa to 80 kDa, about 20 kDa to 60 kDa, about 30 kDa to about 50 kDa, usually about 0.5 kDa to about 10 kDa.

Methods of Making deNAc SA Antigens from Gangliosides

In general, deNAc SA antigens can be produced from gangliosides by biosynthesis of a ganglioside derivative in a mammalian cell (e.g., a cancerous mammalian cell), or other suitable source, by culturing the cell in growth media supplemented with a mixture of an amine-protected mannosamine (e.g., N-trihaloacyl mannosamine) and acyl mannosamine (e.g., N-trihaloacetyl and N-acetyl mannosame). The amine-protected mannosamine and acyl mannosamine can be provided in the culture medium in a desired ratio such that the ganglioside derivative expressed by the cell contains fewer than 90%, fewer than 85%, fewer than 84%, fewer than 80%, fewer than 75%, fewer than 70%, fewer than 60%, or fewer than 55%, usually greater than 10%, 15%, 16%, 25%, 30%, 40%, or 45%. amine-protected (e.g., N-trihalo acylated) residues relative to the total residues of the ganglioside produced.

This method can provide for control of the level of acylation of the final product after removal of the amine protecting group and reducing or avoiding undesirable side reactions with free amino groups, so as to provide a de-N-acetylated ganglioside having a desired level of acylation. In general, the proportion of de-N-acetyl residues is controlled by limiting the amount of amine-protected mannosamine reagent (e.g., N-trihalo acetyl mannosamine). The de-N-acetylated product can be recovered from the cells by any convention method, for example, cooling, neutralizing, purification if desired, and lyophilization.

The biosynthetic production methods are described in more detail below, as well as in the Examples.

Biosynthetic deNAc SA Antigen Production by Production of a Ganglioside Derivative in a Mammalian Cell In one embodiment, deNAc SA antigens are generated by culturing a mammalian cell, (e.g., a cancerous cell of a desired tissue type or cancer type (e.g., a cell of a primary tumor, a metastais of a tumor, or a tumor cell line, e.g., a melanoma cell line (e.g., SK-MEL-28 cell line)), in the presence of one or more N-acyl mannosamine derivatives and under conditions to promote production of ganglioside derivatives having N-acyl sialic acid residues. This can be accomplished by including in the cell culture medium a mannosamine derivative having a desired N-acyl group.

Any suitable mammalian cell which provides for ganglioside production at a desired level can be used in the biosynthetic methods of the invention. Such cells can naturally express gangliosides, or can be engineered to express or overexpress a ganglioside, e.g., GD3 (see, e.g., CHO cells transfected with GD3 synthase (ST8Sia-I), described in Satake et al. J. 2003 Biol. Chem. 278:7942-7948). In some embodiments, the cell used in the biosynthetic methods use cancerous cells that produce GD3 at an elevated level relative to non-cancerous cells (e.g., of the same tissue type or origin). Exemplary cells include, but are not limited to, cells or cell lines of neuroectodermal origin, cancer cells or cell lines (e.g., SK-MEL-28 cells, SK-MEL-37 cells, M21 cells, MELUR cells, and the like), and the like.

In one embodiment, the N-acyl mannosamine derivative is a mannosamine comprising an amine protecting group (a "protected mannosamine" or "amine protected mannosamine"), exemplified herein by N-trihaloacyl mannosamines, to accomplish "feeding" of the mannosamine derivative to the cancerous cell. Exemplary amine protected mannosamines suitable for use in the invention include any amine protected mannosamine that can incorporated into the cells ganglioside synthetic pathway to provide for production of a protected ganglioside derivative. Exemplary amine protected mannosamine reagents include N-trihaloacyl mannosamine, e.g., N-trihaloacetyl mannosamine (e.g., N-trichloroacetyl mannosamine, trifluoroacetyl mannosamine), N-formyl mannosamine, and the like). In addition to the amine-protected mannosamine, the culture medium generally also includes an N-acetyl mannosamine, to provide for a ganglioside derivative having both protected sialic acid residues and N-acetylated sialic acid residues.

In a related embodiment, where a ganglioside derivative having mixed N-acyl sialic acid residues is desired, the culture medium includes mixed N-acyl mannosamine reagents. For example, the N-acyl mannosamine can comprise saturated or unsaturated acyl groups, usually saturated acyl groups, of from $C_1$-$C_5$, more usually $C_2$-$C_5$, more usually $C_2$-$C_4$, more usually $C_2$-$C_3$, with acetyl or propionyl groups being of particular interest. Culturing the cancerous cells in the presence of such mixed N-acyl mannosamine reagents can provide for production of a ganglioside derivative having mixed N-acyl sialic acid residues, e.g,. N-acetyl sialic acid, N-propionyl sialic acid, and the like. In one embodiment of particular interest, the cells are cultured in the presence of a mixture of a protected mannosamine (e.g., a N-trihaloacyl mannosamine) and N-acyl mannosamines (e.g., a mixture of N-acetyl mannosamine and N-propionyl mannosamine).

In another embodiment, a mammalian cell (e.g., a cancer cell) is cultured in the presence of a mixture of an N-acyl mannosamine (e.g., N-acetyl mannosamine) and a N-trihaloacyl mannosamine. The relative amounts of mannosamine reagents in the culture (e.g., the ratio of N-trihaloacyl mannosamine and N-acetyl mannosamine) are provided so that the biosynthetic end product contains the desired ratio of different sialic acid residues and/or derivatives in the ganglioside derivative (e.g., trihaloacylated residues and acylated residues on the ganglioside derivative). In general, the protecting groups (e.g., the trihaloacylated groups) are removed to provide a free amine in the final ganglioside derivative product. For example, where the ratio of free amines to acylated residues in the final de-N-acetylated ganglioside derivative product is to be about 1:10, 1:4, or 1:1, the ratio of N-trihaloacyl mannosamine to mannosamine is about 1:10, 1:4, or 1:1. Stated differently, the amount of N-trihaloacyl mannosamine in the culture is roughly equal to the fraction of de-N-acetyl sialic acid groups desired in the final de-N-acetylated ganglioside derivative product after deprotection (e.g., 10%, 25%, 50%, and the like).

Similarly, the relative amounts of "unprotected" N-acyl mannosamines (mannosamines that do not contain an amine protecting group, but which can comprise, for example, an acetyl or proprionyl group as the N-acyl group) in the culture can be provided so as to provide for a desired ratio of differently acylated sialic acid residues in the ganglioside derivative. For example, where the ganglioside derivative is to have a ratio of acetylated residues to propionylated residues of 2:1 or 1;1, N-acetyl mannosamine and N-propionyl mannosamine is provided in the same or similar ratio in the culture.

The deNAc SA antigens produced from the gangliosides can then be isolated from the cells using methods known in the art. Where the ganglioside derivative contains an amine protecting group, such ganglioside derivatives are especially suitable for generating a ganglioside derivative having further modification, e.g., generating a conjugate (e.g,. by periodate oxidation of the non-reducing end) or modifying a sialic acid residue to provide an alkyl secondary amine, particularly a $C_1$ amide, at a non-reducing end of the ganglioside derivative. After modification is completed, the trihaloacyl protecting groups can be removed as described above. For example, the protecting groups can be removed by reductive amination (e.g., with sodium cyanoborohydride) or further reduction (e.g., with sodium borohydride or treatment with base at pH 9 or greater) to provide a free amine.

In related embodiments, compositions comprising a mammalian cell having a cell surface trihaloacylated ganglioside derivative, including both whole cells and membrane extracts thereof, are contemplated by the invention. The invention also contemplates trihaloacylated ganglioside derivatives isolated from such cells. In addition, the invention contemplates methods of making deNAc SA antigens using such cells. In related embodiments, the invention provides a composition having cells with cell surface de-N-acetylated gangliosides, and/or membranes obtained from such cells, where the cells or membranes are produced using the biosynthetic methods described here. These compositions can be used to elicit antibodies specific for de-N-acetylated gangliosides. Immunization protocols available in the art, as well as those described herein, can be readily adapted to accomplished production of antibodies of a desired specificity.

DeNAc SA Antigen Conjugates

DeNAc SA antigens, a protected amine deNAc SA antigen, can be conjugated to a carrier, so as to provide a deNAc SA antigen -carrier complex. The conjugated antigen-carrier complex can comprise multiple carrier molecules, multiple deNAc SA antigen molecules, or both.

As noted above, the deNAc SA antigen of the conjugate can be provided as a dimer defining a minimal epitope as described above, or as a polymeric unit (e.g., two or more dimeric units defining the epitope described above). Where the deNAc SA antigen is a polymeric structure, the deNAc SA antigen can be homopolymeric or heteropolymeric. The composition can comprise additional residues attached at the non reducing terminus, reducing-terminus or both the non-reducing- and reducing-termini of the polymer or protected amine polymer.

The carrier can be a protein, a peptide, a T cell adjuvant or any other compound capable of enhancing the immune response. The protein may be selected from a group consisting of but not limited to viral, bacterial, parasitic, animal and fungal proteins. In one embodiment, the carrier is albumin. The carrier can be a tetanus toxoid, diphtheria toxoid, meningococcal outer membrane protein complexes (see, e.g., U.S. Pat. No. 4,707,543; U.S. Pat. No. 6,476,201; U.S. Pat. No. 6,558,677), or a bacterial outer protein (such as recombinant N. meningitidis porin B). Such carriers may be obtained from biochemical or pharmaceutical supply companies or prepared by standard methodology (Cruse, J M (ed.) Conjugate Vaccines in Contributions to Microbiology and Immunology vol. 10 (1989)). Synthetic peptides containing T-cell epitopes suitable for use as a carrier may include "universal" T cell epitope (Panina-Bordignon et al 1989 Eur J Immunol 19:2237) or non-natural Pan DR Epitope peptides (PADRE) (del Guercio et al 1997 Vaccine 15:441). Other agents, including other proteins, that can function as carriers would be known to those of ordinary skill in the art of immunology.

Exemplary methods for conjugation of the deNAc SA antigens include, but are not necessarily limited to, conjugation of PS as described in U.S. Pat. Nos. 4,727,136; 5,811,102 (describing a group B meningococcal unsaturated $C_{3-5}$N-acyl derivative polysaccharide conjugate); U.S. Pat. No. 5,969, 130; and U.S. Pat. No. 6,080,589. For example, conjugation can be accomplished by introducing an aldehyde group at the non-reducing end, reducing end, or both of a polysaccharide of a deNAc SA antigen, for use in covalent attachment of one or more carrier proteins. Such can be accomplished through periodiation by contacting the PS or PS derivative with, for example, sodium meta periodate.

Where a deNAc SA antigen comprises an underivatized amino group, certain restrictions may be imposed upon the procedures that can be used to couple the deNAc SA antigen to a carrier, such as a carrier protein. In this embodiment, the carrier is generally modified to contain one or more azide (hydrazide or adipic dihydrazide) groups through the reaction of hydrazide or adipic dihydrazide with the carrier protein activated at carboxyl groups with EDAC (see, e.g., U.S. Pat. No. 6,632,437). Since the pKa of the hydrazide amino group is about 2.5, and since hydrazides are strong nucleophiles, the imine conjugation reaction can be performed at pH of about 5.5-7.5 at which the primary amines on the carrier protein and the polysaccharide are substantially completely protonated and thus less reactive.

DeNAc SA antigen-protein conjugate vaccines can be purified by size exclusion chromatography (ToyoPerl HW-45F). The protein concentration is determined by Lowry protein assay and the amount of conjugated polysaccharide by resorcinol assay (Svennerholm 1957 Biochim biophys Acta 24:604). To ensure that the protein and polysaccharide are covalently linked, the conjugate vaccines are resolved on SDS-PAGE and protein and polysaccharide are detected separately by Western blot using polyclonal anti-carrier protein antisera and anti-PS mAbs to detect the polysaccharide component.

In one example, where the deNAc SA antigen comprises dimeric epitopes, the deNAc SA antigen can be modified to provide for attachment to a carrier and have the following structure:

FORMULA VIII

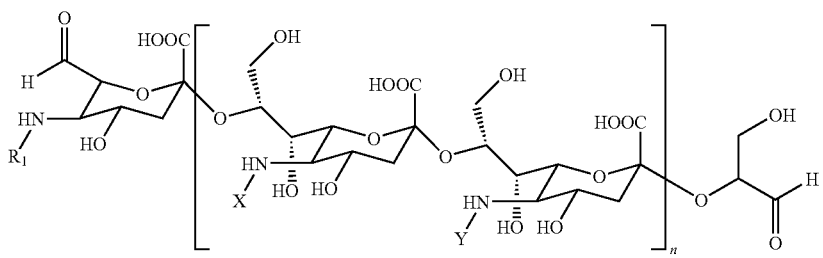

where X, Y, and are as defined above, and $R_1$ is H or an acyl group (e.g., an acetyl group). In other embodiments, R1 is selected independently from H; a saturated or unsaturated acyl group (e.g., a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, a saturated $C_{2-4}$ acyl group); an N-fatty acyl group (e.g. N-lauroyl, N-oleoyl, and the like); or a fatty amine (e.g. dodecyl amine, oleoyl amine, and the like). In one embodiment R1 is a $C_4$ to $C_8$ acyl group, such as n-butanoyl, isbutanoyl, n-pentanoyl, n-hexyanol, n-heptanoyl or n-octanoyl (as described in, for example U.S. Pat. No. 5,576,002), or an unsaturated $C_3$-$C_5$ acyl group, such as those described in U.S. Pat. No. 6,350,449.

In another embodiment where the deNAc SA antigen comprises trimeric repeats, the deNAc SA antigen can be modified to provide for attachment to a carrier and have the following structure:

FORMULA IX

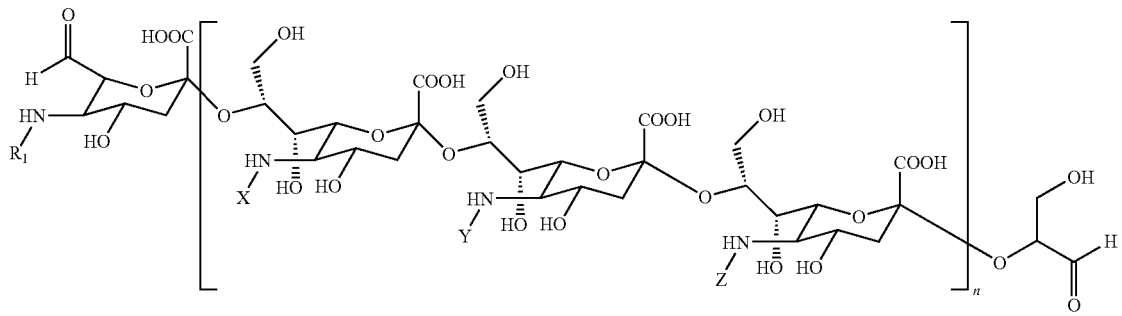

wherein

X, Y and Z are independently H or an amine protecting group; or a saturated or unsaturated acyl group (usually a saturated acyl group), with the proviso that at least one of X, Y, and Z is H or a trihaloacyl group; and at least one of X, Y, and Z is a saturated or unsaturated acyl group, usually a saturated acyl group, with embodiments of particular interest being those in which at least one of X, Y, and Z is H (or an amine protecting group), at least one of X, Y, and Z is an acetyl group, and at least one of X, Y and Z is a propionyl group;

n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually about 4 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest); and $R_1$ is H, an amine protecting group, or an acyl group (e.g., a saturated acyl group, such as an acetyl group). In other embodiments, $R_1$ is selected independently from H; an amine protecting group; a saturated or unsaturated acyl group (e.g., a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, a saturated $C_{2-4}$ acyl group); an N-fatty acyl group (e.g. N-lauroyl, N-oleoyl, and the like); or a fatty amine (e.g. dodecyl amine, oleoyl amine, and the like). In one embodiment R1 is a $C_4$ to $C_8$ acyl group, such as n-butanoyl, isbutanoyl, n-pentanoyl, n-hexyanol, n-heptanoyl or n-octanoyl (as described in, for example U.S. Pat. No. 5,576,002), or an unsaturated $C_3$-$C_5$ acyl group, such as those described in U.S. Pat. No. 6,350,449.

Propionyl-Linked or Acetyl-Linked Conjugates

In another embodiment, the invention features a composition comprising a deNAc SA antigen comprising a structure represented by the formula:

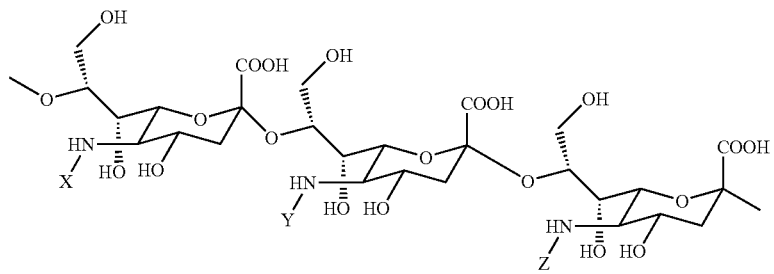

wherein X, Y, and Z are independently an acryl group (e.g., N-acryl, methacryl) or haloacetyl group (e.g., bromoacetyl, chloroacetyl), wherein at least one of X, Y, and Z is H, and at least one of X, Y, and Z is a saturated acyl group. The deNAc SA antigen can be optionally conjugated to a carrier protein or alkyl secondary amine covalently linked by reaction with the acryl or haloacetyl group. DeNAc SA antigens in this embodiment generally have one or more such structures positioned within the polymer. For example, the structure above can represent, for example, from about 10% to 100%, from about 25% to 90%, from about 50% to 75% of the deNAc SA antigen.

Propionyl-linked or acetyl-linked deNAc SA antigen conjugates can be generated by reacting at least partially de-N-acetylated PS (or other sialic acid residue-containing polymer, such as a sialic acid-modified protein or ganglioside) with activated acrylic acid or activated haloacetic acid, where the activated acrylic acid or activated haloacetic acid is generated by reaction with a carboxyl activating agent such as a carbodiimide, e.g., EDC (1-ethyl-3-(3-dimethylaminopropyl)carbodiimide hydrochloride). The amount of activated acrylic acid or activated haloacetic acid can be selected to a desried level of conjugation, e.g., from about 10% to about 100%, about 25% to about 80%, about 50% to 75% of the deNAc SA in the PS.

Exemplary propionyl-linked conjugates comprise a structure represented by the formula:

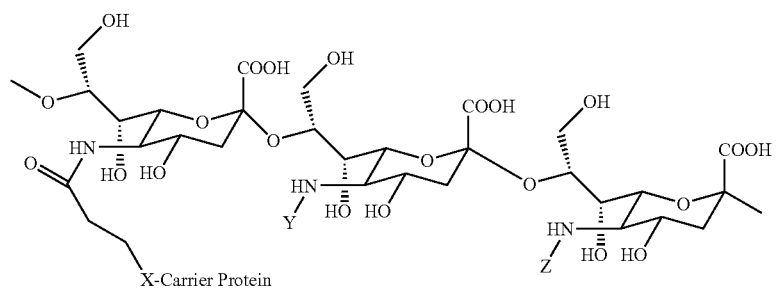

wherein X is a thiol from a reacted cysteine residue, or an amino group of a reacted lysine, histidine or arginine residue of a carrier protein, and Y and Z are independently H or a saturated acyl group, wherein at least one of Y and Z is H and at least one of Y and Z is a saturated acyl group. It will be understood that deNAc SA antigen conjugates contemplated here include those in which the carrier is conjugated through an acryl group positioned at Y (with X and Z being either H or a saturated acyl group) or conjugated through an acryl group positioned at Z (with X and Y being either H or a saturated acyl group).

Exemplary conjugates linked to a carrier through reaction with a haloacetyl group comprise a structure represented by the formula:

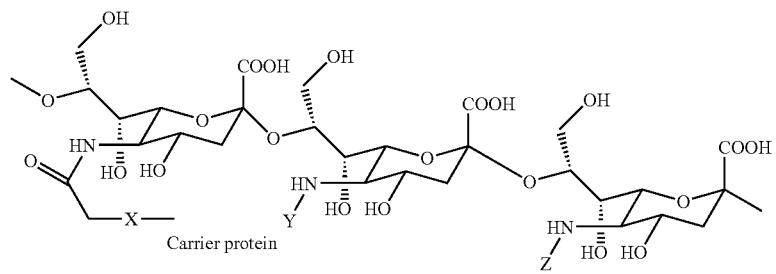

wherein X is a thiol from a reacted cysteine residue of a carrier protein, or an amino group of a reacted lysine, histidine or arginine residue of a carrier protein, and Y and Z are independently H or a saturated acyl group, wherein at least one of Y and Z is H and at least one of Y and Z is a saturated acyl group. It will be understood that deNAc SA antigen conjugates contemplated here include those in which the carrier is conjugated through a haloacetyl group positioned at Y (with X and Z being either H or a saturated acyl group) or conjugated through a haloacetyl group positioned at Z (with X and Y being either H or a saturated acyl group).

Treatment of DeNAc SA Antigen Preparations with Exosialidase

Polysaccharide (PS), oligosaccharide (OS), or other N-acylated sialic acid polymer contaminants that do not contain deNAc SA residues can be decreased, and thus deNAc SA antigen enriched, in compositions containing deNAc SA antigens by treatment with an exosialidase (also referred to as an exoneuraminidase) to promote cleavage of sialic acid residues in contaminating sialic acid polymers (e.g., as in PS and OS) at the α(2→8)-gylocosidic bond. Suitable exosialidases include the exosialidase of *Arthrobacter ureafaciens* (e.g., SIALIDASE A™), *Clostridium perfringens* (e.g, SIALIDASE I™), *Vibrio cholerae* (e.g., SIALIDASE V™), *Salmonella typhimurium* (e.g., SIALIDASE T™), Newcastle disease virus, Hitchner B1 Strain (e.g., SIALIDASE N™), and other exosialidases that can cleave α(2→8)-glycosidic bonds. Exosialidases suitable for use are commercially available.

Treatment with sialidase can be accomplised by for example, incubation of the composition in a buffer (e.g., an alkali acetate buffer, such as a sodium acetate buffer) at a suitable pH, where the pH can be selected so as to avoid degradation of the deNAc SA antigen (e.g., PS derivative) and/or hydrolosis of the deNAc SA antigen (e.g., PS derivative) (e.g., which can result in production of sialic acid derivatives, such as cyclic lactone residues). For example, incubation of the sample at a pH of about 6.5 can provide for exosialidase activity while reducing deNAc SA antigen degradation. Incubation can be for any suitable period, e.g., several hours (e.g., 5, 10, 12 hours or more) to several days (e.g., 1, 2, 3, 4, 5 or more days). Incubation can be performed at any suitable temperature, including room temperature (e.g., about 37° C.). Where low pH results in formation of sialic acid derivatives, the composition can be incubated at an elevated pH (e.g., greater than pH 6.5, usually greater than pH10) for a short period of time (e.g., 30 min to 1 hour) in order to hydrolyze, for example, cyclic lactones.

Treatment with exosialidase depletes non-reactive, fully N-acylated sialic acid polymers (e.g., N-acylated PS) which may be present as a contaminant in deNAc SA antigen preparations, particularly those preparations made using a synthetic method such as those described herein. In this manner, treatment with an exosialidase can provide for enrichment of deNAc SA antigen in a composition. For example, treatment with sialidase can provide for a composition with less than 60%, or less than 40% by weight N-acylated PS.

Exosialidase-treated deNAc SA antigen can be conjugated to a carrier protein using any suitable method. For example, exosialidase-treated deNAc SA antigen can be conjugated by N-acylation (e.g., using acrylic acid or haloacetic acid), followed by conjugation to a protein carrier of interest.

Immunogenicity of DeNAc SA Antigens and DeNAc SA Antigen Conjugates The isolated deNAc SA antigen, with or without further conjugation or in the presence or absence of a presentation structure, may be immunogenic or, alternatively, the immunogenicity may arise from the conjugation. Methods of measuring immunogenicity are well known to those in the art and primarily include measurement of serum antibody including measurement of concentration, avidity, and isotype distribution at various times after injection of the construct. Greater immunogenicity may be reflected by a higher titer and/or increased life span of the antibodies. Immunogenicity may be measured using in vitro bactericidal assays as well as by the ability of sera from immunized animals to confer passive protection to infection or disease in a suitable animal challenge model. Immunogenicity may be measured in the patient population to be treated or in a population that mimics the immune response of the patient population.

One means of determining the immunogenicity of a given substance is to first obtain sera of an animal (e.g., mouse) both before immunization, and then after priming with deNAc SA antigen or conjugate, followed by boosting with additional doses. Following this, the strength of the post-immunization sera binding to a deNAc SA epitope is ascertained using an ELISA, and compared to the corresponding results with control mock-immunized animals.

The deNAc SA antigen can prime for an immune response to a deNAc SA antigen conjugate that both reduces production of or avoids production of auto-antibodies and can provide for enhanced antibody response to deNAc SA antigen conjugate compared to a response of an individual not primed with the de-N-acetylated PS and who has been vaccinated with the same PS conjugate Antigenic Composition Formulations "Antigen composition", "antigenic composition" or "immunogenic composition" is used herein as a matter of convenience to refer generically to compositions comprising a deNAc SA antigen, including deNAc SA antigen conjugates. Antigen compositions can comprise a deNAc SA antigen, conjugate thereof, or both. Compositions useful for eliciting antibodies against NmB, E. coli K1, or cancer cells, particularly cancer cells, are contemplated by the present invention.

The deNAc SA antigens can be provided in such compositions in an isolated form, or in membranes (e.g., in vesicles, e.g., outer membrane vesicle or microvesicles, such as produced from a NmB strain). Where the deNAc SA antigen is generated using the biosynthetic methods involving mammalian cells, the deNAc SA antigen can be provided on the surface of a whole mammalian cell or a membrane or lipid extract of a mammalian cell. Where a whole mammalian cell is used, the mammalian cell will usually be inactivated so as to prevent further proliferation once administered to the subject. Any physical, chemical, or biological means of inactivation may be used, including but not limited to irradiation (e.g., with at least about 5,000 cGy, usually at least about 10,000 cGy, more usually at least about 20,000 cGy); or treatment with mitomycin-C (e.g., usually at least 10 .mu.g/mL; more usually at least about 50 µg/mL).

In one embodiment, especially where the deNAc SA antigen was generated by PS, the deNAc SA antigen composition has been treated with an exosialidase to decrease contaminating PS and OS and enrich for deNAc SA in the composition.

Compositions of the invention (particularly those suitable for use as vaccines) comprise an immunologically effective amount of antigen, as well as any other compatible components, as needed. By "immunologically effective amount" is meant that the administration of that amount to an individual, either in a single dose, as part of a series of the same or different antigenic compositions, is effective to elicit an antibody response effective for treatment or prevention of a symptom of a cancerous cell having a cell surface-accessible deNAc SA epitope (e.g., a ganglioside that is at least partially de-N-acetylated). DeNAc SA antigen compositions can be administered to elicit an anti-SEAM 3 reactive antigen antibody response in a subject.

The amount administered varies depending upon the goal of the administration (e.g., to provide for immunotherapy in a human subject, to provide for antibody production for generating hybridomas (e.g., as in a non-human host)), the health and physical condition of the individual to be treated, age, the taxonomic group of individual to be treated (e.g., human, non-human primate, primate, etc.), the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials. Dosage treatment may be a single dose schedule or a multiple dose schedule (e.g., including booster doses). The vaccine may be administered in conjunction with other immunoregulatory agents.

The compositions of the invention can be provided in a pharmaceutically acceptable excipient, which can be a solution such as an aqueous solution, often a saline solution, or they can be provided in powder form. The compositions of the invention can comprise a deNAc SA antigen and an adjuvant. Examples of known suitable adjuvants that can be used in humans include, but are not necessarily limited to, alum, aluminum phosphate, aluminum hydroxide, MF59 (4.3% w/v squalene, 0.5% w/v Tween 80, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIM, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr opin Mol Ther 2001 3:15-24; Roman et al., Nat. Med, 1997, 3, 849-854; Weiner et al., PNAS USA, 1997, 94, 10833-10837; Davis et al, J. Immunol, 1998, 160, 870-876; Chu et al., J. Exp. Med, 1997, 186, 1623-1631; Lipford et al, Ear. J. Immunol., 1997, 27, 2340-2344; Moldoveami e/ al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157,4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581] i.e. containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+ 3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), and the like. Adjuvants suitable for human use are of particular interest where the subject is a human.

The antigen compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of antigens of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Immunization

The deNAc SA antigen (which may be optionally conjugated) can be used alone or in combination with other vaccines. When used in combination, the various compositions can be provided in the same or different formulations. Where administered in different formulations, the compositions can be administered at the same or different dosage regimen (e.g., by the same or different routes, at the same or different time (e.g., on the same or different days)), and the like). In general, administration of the deNAc SA antigen can be performed serially, at the same time, or as a mixture, as described in more detail below. Preferably, administration is serial, with repeated doses of deNAc SA antigen. Exemplary immunization regimens are described below in more detail.

In general immunization is accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that when administered orally, deNAc SA antigens should be protected from digestion. This is typically accomplished either by complexing the deNAc SA antigen with a composition to render it resistant to acidic and enzymatic hydrolysis or by packaging in an appropriately resistant carrier such as a liposome. Means of protecting a compound of interest from digestion are well known in the art.

In order to enhance serum half-life, the antigenic preparations that are injected may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

Where used as a immunotherapy, the compositions can be administered to subject that is at risk of disease to prevent or at least partially arrest the development of disease and its complications. A subject is "at risk" where, for example, the subject exhibits one or more signs or symptoms of disease, but which are insufficient for certain diagnosis and/or who has been or may be exposed to conditions that increase the probability of disease. For example, the antigen compositions can also be administered to subject that is at risk of a cancer, has a cancer, or is at risk of metastasis of a cancer having a cell surface deNAc SA epitope (e.g., a cell surface ganglioside that is at least partially de-N-acetylated).

An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the antigen compositions may be administered depending on the dosage and frequency required and tolerated by the patient, and route of administration. In general, immunization is provided to as to elicit an immune response in the subject. As discussed herein the deNAc SA antigen compositions can provide the advantage that immunization does not elicit detectable antibodies that significantly cross-react with polysialic acid in the subject, but that specifically bind a deNAc SA epitope (e.g., on a cancerous cell).

Immunization Regimen

DeNAc SA antigens are administered to a host in a manner that provides for production of selective anti-deNAc SA epitope antibodies. DeNAc SA antigen compositions canbe administered serially. First, an immunogenically effective dose of a deNAc SA antigen (which may be conjugated to a carrier, and may be with or without excipients) is administered to a subject. The first dose is generally administered in an amount effective to elicit an immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient, usually about 0.005 mg to about 0.015 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first deNAc SA antigen composition, a therapeutically effective dose of a second antigen composition (e.g. deNAc SA antigen, optionally conjugated and with or without excipients) can be administered to the subject after the subject has been immunologically primed by exposure to the first dose. The booster may be administered days, weeks or months after the initial immunization, depending upon the patient's response and condition.

An immune response to the first antigen composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) and/or demonstrating that the magnitude of the immune response to the second injection is higher than that of control animals immunized for the first time with the composition of matter used for the second injection (e.g. immunological priming). Immunologic priming and/or the existence of an immune response to the first antigen composition may also be assumed by waiting for a period of time after the first immunization that, based on previous experience, is a sufficient time for an immune response and/or priming to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

In certain embodiments, an effective dose of a third deNAc SA antigen composition (e.g. deNAc SA antigen, optionally conjugated and with or without excipients) is administered to the subject after the individual has been primed and/or mounted an immune response to the second antigen composition. The third booster may be administered days, weeks or months after the second immunization, depending upon the subject's response and condition. The existence of priming and/or an immune response to the second antigen composition may be determined by the same methods used to detect an immune response to the second antigen composition. The existence of priming and/or an immune response to the second antigen composition may also be assumed by waiting for a period of time after the second immunization that, based on previous experience, is a sufficient time for an immune response to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

The use of a fourth, fifth, sixth or greater booster immunization, using either a fourth, fifth or sixth antigen composition or more is also contemplated.

In one embodiment, a deNAc SA antigen composition is administered at least once, usually at least twice, and in some embodiments more than twice.

In one embodiment, a deNAc SA antigen composition (e.g., de-N-acetylated PS derivative or de-N-acetylated PS derivative conjugate) is administered as the first antigen composition so as to prime the immune response. Subsequent antigen compositions administered (e.g., the booster doses) can be the same or different deNAc SA antigen composition, or can be an antigenic composition that boosts the primed immune response to the first antigen composition. Without being held to theory, the initial priming dose of a deNAc SA antigen composition directs the host immune response toward production of antibodies that are minimally cross-reactive with host polysialic acid, and thus away from away from production of such autoreactive antibodies. Once the host's immune response is primed in this manner, then exposure to antigens that might otherwise elicit an autoimmune response may result in reduced (including insubstantial or not clinically relevant) production of autoantibodies that cross-react with host polysialic acid.

In one embodiment, the antigen compositions can be administered to a mammalian subject (e.g., human) that is immunologically naïve with respect to a deNAc SA epitope-containing antigen. In other embodiments (which may or may not be related), the subject is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age. Treatment of such younger subjects may be of interest in treatment of certain cancers, such as neuroblastomas.

The deNAc SA antigen composition is to be used as a vaccine, administration can be initiated prior to the first sign of disease symptoms, at the first sign of possible disease, or prior to or after diagnosis of a primary cancer and/or a metastases of a cancer having a cell surface deNAc SA epitope (e.g., a ganglioside that is at least partially de-N-acetylated).

Antibody Production

It will be readily apparent that compositions comprising a deNAc SA antigen can be used to produce anti-deNAc SA antigen antibodies, including monoclonal antibodies (mAbs) that can be suitable for use in antibody-based cancer therapies described herein. Methods for generating mAbs are well known in the art, and readily adapted for use in production of anti-deNAc SA epitope mAbs.

For example, hybridomas for mAb production can be formed by isolating the stimulated immune cells from an animal immunized with a deNAc SA antigen (usually a non-human animal), such as those from the spleen of an immunized animal. These cells are then fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

The immortal fusion partners utilized can be derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256: 495 (the disclosures of which are hereby incorporated by reference).

Large quantities of mAbs having a desired anti-deNAc SA epitope specificity can be obtained by identifying secreting hybridomas producing the desired antibodies, and injecting these hybridoma clones into the peritoneal cavity of mice and harvesting the ascites fluid therefrom. The mice, preferably primed with pristane, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

Anti-deNAc SA epitope antibodies, including antigen binding fragments of anti-deNAc SA epitope antibodies, can be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Once obtained, the antibody can be isolated and, where desired, purified, for use in the assays and therapies disclosed herein. Isolation and purification of antibodies can be accomplished using techniques well known in the art, and can provide for antibody-containing preparations at least 50% to 60%, by weight, free from organic molecules with which the antibody is naturally associated or with which it is associated during manufacture. Antibody preparations include those that contain antibody in an amount of at least 75%, more usually at least 90%, and generally at least 99%, by weight.

In one embodiment, the anti-deNAc SA epitope antibody is isolated away from contaminants, especially cationic contaminants, by contacting an antibody suspension (e.g., in a buffer) under conditions of high salt concentration. Suitable salts include alkali metal salts (e.g., alkali metal sulfates (e.g, sodium sulfate), alkali metal halides (e.g., sodium chloride), alkali metal acetate salts (e.g, sodium acetate), and the like. A "high salt concentration" refers to a salt concentration of at least about 0.5 M or more up to and including 1 M salt. The high salt solution containing the antibody is incubated under conditions suitable to separate contaminants from the antibody and for a time sufficient to provide for disruption of ionic and/or electrostatic bonds that may be present between the antibody and cationic or other charged contaminants. Suitable periods of time include, but are not limited to about 12 hrs, 16 hrs, 18 hrs or more. The solution may be incubated at any suitable temperature, e,.g., 4° C., 37° C., etc. The antibody can then be isolated and/or purified from the solution. For example, the antibody-containing solution can be processed to remove precipitates (e.g., by centrifugation), and subjected subjected to further isolation and/or purification techniques to isolate the antibody from the solution, e.g., by size exclusion chromatography. Antibody-containing fractions can be further purified by dialysis (e.g., against phosphate buffered solution (PBS)) and filtration. This high salt treatment was found to be pariticularly suitable for isolation and/or purification of SEAM 3 mAb, as it resulted in removal of contaminants that affected SEAM 3 mAb activity against cancerous cells presenting cell surface SEAM 3-reactive antigen.

Antibody-Based Diagnostics and Therapeutics

DeNAc SA antigens (including unconjugated and conjugated forms) can be used to generate antibodies, which antibodies can be used as reagents for use in diagnostic assays and in antibody-based therapy. The present disclosure provides comprising antibodies that selectively bind a deNAc SA epitope (e.g., as present on a de-N-acetylated ganglioside; *N. meningitidis* PS, particularly NmB PS; or *E: coli* K1 PS, and the like). Such antibodies can exhibit little or no detectable binding to human polysialic acid (that is, the antibodies are not significantly cross-reactive with PSA on normal (non-cancerous) human tissue). The anti-deNAc SA epitope antibodies can be monoclonal or polyclonal, and can be provided with a suitable excipient. In some embodiments the antibodies can be immobilized on a support, or provided in a container such as a vial, particularly a sterile vial, optionally labeled for use in a diagnostic or therapeutic method as described in more detail below.

Diagnostics

Antibodies reactive with a deNAc SA epitope can be used to detect deNAc SA antigens in a biological sample obtained from a subject having or suspected of having cancerous cells having a cell surface accessible deNAc SA epitope (e.g., a de-N-acetylated cell surface ganglioside) using anti-deNAc SA epitope antibodies in immunodiagnostic techniques. The antigen binding specificity of anti-deNAc SA epitope antibodies can be exploited in this context, to facilitate detection of deNAc SA epitopes on a cancerous cell in a sample with little or no detectable binding to host-derived PSA, thereby reducing the incidence of false positive results. Such detection methods can be used in the context of diagnosis, identification of subject suitable to anti-deNAc SA antigen-based and/or antibody-based therapy where the antibody specifically binds an deNAc SA epitope and/or a SEAM 3-reactive antigen, monitoring of therapy (e.g., to follow response to therapy), and the like.

Suitable immunodiagnostic techniques include, but are not necessarily limited to, both in vitro and in vivo (imaging) methods. Where the methods are in vitro, the biological sample can be any sample in which a deNAc SA antigen may be present, including but not limited to, blood samples (including whole blood, serum, etc.), tissues, whole cells (e.g., intact cells), and tissue or cell extracts. Assays can take a wide variety of forms, such as competition, direct reaction, or sandwich type assays. Exemplary assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include detctable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-deNAc SA epitope antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing deNAc SA epitopes under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with anti-deNAc SA epitope antibody according to the present invention. A biological sample containing or suspected of containing a deNAc SA antigen (e.g., a tumor antigen having a deNAc SA epitope, such as a de-N-acetylated ganglioside), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound deNAc SA antigen from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and deNAc SA antigen form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing deNAc SA antigen to provide for formation of particle-antibody-deNAc SA antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which a deNAc SA antigen may be present, including but not limited to, blood samples (including whole blood, serum, etc.), tissues, whole cells (e.g., intact cells), and tissue or cell extracts.containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments it may be desirable to conduct the assay using a sample from the subject to be diagnosed that contains intact, living cells. DeNAc SA antigen detection can then be assessed on an extracellular surface of the cells, and can further be assessed during cell division.

Diagnostic assays can also be conducted in situ. For example, anti-deNAc SA epitope antibodies can be detectably labeled, administered to a subject suspected of having a cancer characterized by cell surface expression of a deNAc SA epitope, and bound detectably labeled antibody detected using imaging methods available in the art.

The diagnostic assays described herein can be used to determine whether a subject has a cancer that is amenable to therapy using a deNAc SA antigen-based immunotherapy (e.g., deNAc SA antigen vaccine and/or anti-deNAc SA antigen antibody therapy). The diagnostic assays can inform selection of therapy and treatment regimen by a clinician.

In one embodiment, the detection assays involve detection of a SEAM 3-reactive antigen in a sample, where the sample can contain Where the methods are in vitro, the biological sample can be any sample in which a SEAM 3-reactive antigen may be present, including but not limited to, blood samples (including whole blood, serum, etc.), tissues, whole cells (e.g., intact cells, i.e., cells that have not been subjected to permeabilization), or cell lysates (e.g, as obtained from treatment of a tissue sample). For example, the assay can involve detection of a SEAM 3-reactive antigen on cells in a histological tissue sample. For example, the tissue sample may be fixed (e.g., by formalin treatment) and may be provided embedded in a support (e.g., in paraffin) or frozen unfixed tissue.

The SEAM 3-reactive antigen can be detected by detection of specific binding of an antibody, usually a monoclonal antibody (mAb), that has the antigen-binding specificity of SEAM 3. In this embodiment, the SEAM 3-reactive antigen may be present on the cell surface at any stage of the cell cycle, including during cell division. Of note is that in some instances, cancers that present a SEAM 3-reactive antigen during cell division may present a lower or no detectable level of SEAM 3-reactive antigen when the cell is quiescent (i.e., not undergoing cell division). However, as illustrated in the examples below, SEAM 3-reactive antigen can be detected in non-dividing cells by detecting SEAM 3-reactive antigen in a permeabilized test cell. A test cancer cell that exhibits a pattern of staining with a SEAM 3 antibody (or an antibody having the antigen binding specificity of SEAM 3) that is distinct from a pattern of antibody staining in a normal cell is identified as a cancerous cell that exhibits a SEAM 3-reactive antigen. Such cancers are thus amenable to therapy with an antibody that specifically binds the SEAM 3-reactive antigen (e.g., the mAb SEAM 3).

The above-described assay reagents, including the antibodies generated by immunization with the deNAc SA antigen according to the methods described herein, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Antibody-Based Therapies

Antibodies generated using the methods of the invention to treat or prevent cancer associated that presents a deNAc SA epitope in a mammalian subject, particularly in a human. Antibodies generated using a deNAc SA antigen (including conjugates) can be provided in a pharmaceutical composition suitable for administration to a subject, so as to provide for anti-cancer therapy.

More particularly, anti-deNAc SA epitope antibodies generated according to the methods described herein can be administered to a subject (e.g. a human patient) to, for example, facilitate reduction of viability of cancerous cells, e.g., to provide for or enhance a immune response or anti-cancer therapy to reduce tumor size, reduce tumor load, and/or improve the clinical outcome in patients. In particular, antibodies that have the binding specificity of the mAb SEAM 3 (and thus bind the epitope bound by the mAb SEAM3) can be used to disrupt the cell cycle of the cancer cell, and facilitate entry of the cell into apoptosis, e.g., by inducing cancerous cells to enter the pre-$G_o$ cell cycle phase. The antibodies can optionally have attached a an anti-cancer drug for delivery to a site of a cancer cell to further facilitate tumor killing or clearance, e.g., an anti-proliferation moiety (e.g., VEGF antagonist, e.g., an anti-VEGF antibody), a toxin (e.g., an anti-cancer toxin, e.g., ricin, *Pseudomonas* exotoxin A, and the like), radionuclide (e.g. $^{90}$Y, $^{131}$I, $^{177}$L and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

Methods for producing and formulating anti-deNAc SA epitope antibodies suitable for administration to a subject (e.g., a human subject) are well known in the art. For example, antibodies can be provided in a pharmaceutical composition comprising an effective amount of an antibody and a pharmaceutical excipients (e.g., saline). The pharmaceutical composition may optionally include other additives (e.g., buffers, stabilizers, preservatives, and the like). An effective amount of antibody is generally an amount effective to provide for enhancing an anti-cancer immune response in a subject for a desired period. A therapeutic goal (e.g., reduction in tumor load) can be accomplished by single or multiple doses under varying dosing regimen.

Antibodies administered to an organism other than the species in which they are raised are often immunogenic. Thus, for example, murine or porcine antibodies administered to a human often induce an immunologic response against the antibody. The immunogenic properties of the antibody are reduced by altering portions, or all, of the antibody into characteristically human sequences thereby producing chimeric or human antibodies, respectively.

Of particular interest are antibodies that have the antigen binding specificity of the mAb SEAM 3. Examples of such antibodies include those having a light chain polypeptide comprising CDR1, CDR2 and CDR3 of the variable reagion of a SEAM 3 light chain polypeptide (amino acid residues 24 to 39, amino acid residues 55 to 61, and amino acid residues 94 to 100, respectively set forth in FIG. 52) and a heavy chain polypeptide comprising CDR1, CDR2, and CDR3 of the variable region of the SEAM 3 heavy chain polypeptide (amino acid residues amino acid residues 26 to 35, amino acid residues 50 to 66, and amino acid residues 101 to 108, respectively, set forth in FIG. 52). Such antibodies include chimeric antibodies, humanized antibodies, and the like.

Chimeric Antibodies

Chimeric antibodies are immunoglobulin molecules comprising a human and non-human portion. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody can have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989) and WO 90/07861.

Recombinant DNA methods can be used to generate chimeric antibodies in a recombinant expression system. For example, a recombinant DNA vector is used to transfect a cell line that produces an anti-deNAc SA epitope antibody. The recombinant DNA vector can contain a "replacement gene" to replace all or a portion of the gene encoding the immunoglobulin constant region in the cell line (e.g. a replacement gene may encode all or a portion of a constant region of a human immunoglobulin, or a specific immunoglobulin class), and a "target sequence" which allows for targeted homologous recombination with immunoglobulin sequences within the antibody producing cell (e.g., hybridoma).

In another example, a recombinant DNA vector is used to transfect a cell line that produces an antibody having a desired effector function (e.g. a constant region of a human immunoglobulin), in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen-binding and/or have the same effector function yet be altered or improved so that the chimeric antibody may demonstrate a greater antigen specificity, greater affinity binding constant, increased effector function, or increased secretion and production by the transfected antibody producing cell line, etc.

Human Antibodies

In another embodiment, the anit-deNAc SA epitope antibodies are fully human antibodies. Human antibodies are primarily composed of characteristically human polypeptide sequences. The human antibodies of this invention can be produced by a wide variety of methods (see, e.g., Larrick et al., U.S. Pat. No. 5,001,065). Human anti-deNAc SA epitope can be produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. (1983), *Hybridoma* 2: 361-367, Ostberg, U.S. Pat. No. 4,634,664, and Engelman et al., U.S. Pat. No. 4,634,666. Triomas have been found to produce antibody more stably than ordinary hybridomas made from human cells.

Cancer Therapy

Antibodies that specifically bind a deNAc SA epitope can be used in anti-cancer therapy for a mammalian subject, particularly a human, where the cancerous cells present a deNAc SA epitope on an extracellularly accessible cell surface (e.g., a deNAc SA epitope on an at least partially de-N-acetylated ganglioside). Particularly, the antibodies generated using the deNAc SA antigens (including deNAc SA antigen conjugates) can be provided in a pharmaceutical composition suitable for administration to a subject in need of treatment.

Therapeutic administration of the subject antibodies can include administration as a part of a therapeutic regimen that may or may not be in conjunction with additional standard anti-cancer therapeutics, including but not limited to chemotherapeutic agents and surgery (e.g., as those described further below). In addition, therapeutic administration of the subject antibodies can also be post-therapeutic treatment of the subject with an anti-cancer therapy, where the anti-cancer therapy can be, for example, surgery, radiation therapy, administration of chemotherapeutic agents, and the like. Use of monoclonal antibodies, particularly monoclonal antibodies that can provide for complement-mediated killing, and/or antibody-dependent cellular cytotoxicity-mediated killing, of a target cell are of particular interest.

In certain embodiments, the antibody can be provided alone or can be optionally attached to a compound to facilitate delivery of the compound to the cancer cell to facilitae tumor killing or clearance, e.g., a toxin (e.g., ricin, diptheria toxin, *Pseudomonas* exotoxin A or other toxin), a radionuclide or other molecule that is cytotoxic ($^{90}$Y, $^{131}$I, $^{177}$L and the like). The antibody (or, where bound to a compound, the antibody-compound conjugate) can be provided in solution (e.g., diluted in normal saline solution, PBS, or normal saline or PBS in combination with human albumin (5%)). The antibody can be provided at concentration ranging from about 0.1 mg/ml to about 10 mg/ml, including from about 0.5 mg/ml to about 9 mg/ml, about 1 mg/ml to about 8 mg/ml, about 1.5 mg/ml to about 7.5 mg/ml, about 2 mg/ml to about 7 mg/ml, about 2.5 mg/ml to about 6.5 mg/ml; about 3 mg/ml to about 6 mg/ml, about 3.5 mg/ml to about 5.5 mg/ml, about 4 mg/ml to about 5 mg/ml, and the like.

In other embodiments, the antibody can be adminsitered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the anti-deNAc SA epitope antibody is used in connection with surgical intervention, the antibody can be administered prior to, at the time of, or after surgery to remove cancerous cells, and may be administered systemically or locally at the surgical site. The antibody alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.). Antibody administration by can be accomplished by infusion, e.g., by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc.

Antibody-Based Therapy of Metastases

A primary problem with treating cancer is metastases or the propensity for being released from the primary site of the tumor, traveling in the blood stream to distal sites, followed by attachment to tissues at distal sites and secondary tumor formation. The problem is often exacerbated during surgical removal of the primary tumor as the result of mechanical disruption of the mass results in metastasis and adhesion to a secondary location following surgery. Treatment with an anti-deNAc SA epitope antibody (e.g., SEAM 3) after identification of a primary tumor composed of cells expressing a deNAc SA epitope (e.g., a de-N-acetyl ganglioside) and/or after surgical removal of a tumor can prevent adhesion of the any cancer cells following metastasis, and is contemplated by the invention. In addition, anti-deNAc SA epitope antibody (e.g., SEAM 3) binding to cancer cells that express a deNAc SA epitope (e.g., de-N-acetyl ganglioside or sialic acid modified protein) can provide for a cytotoxic effect on cells that is independent of complement (see Examples Section). Therefore, in certain embodiments, an anti-deNAc SA epitope antibody (e.g., SEAM 3) is useful in treating cancer patients who have a complement deficiency, e.g., as a result of a environmental exposure (e.g, a drug therapy), a genetic deficiency, etc. Examples of complement deficiencies include those involving inhibition of C1, C2, C6, C9, and properdin.

Combination Cancer Therapies

Any of a wide variety of cancer therapies can be used in combination with the deNAc SA-based or anti-deNAc SA epitope antibody-based therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283, 253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia;* or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Cancers Amenable to Therapy by deNAc SA Antigen Immunization-Based or Antibody-Based Therapy The deNAc SA antigen find use in a variety of cancer therapies (including cancer prevention (e.g., cancer vaccine) and post-diagnosis cancer therapy) or cancer diagnostics for cancers having a cell surface deNAc SA epitope. Subjects having, suspected of having or at risk of developing a tumor are contemplated for therapy and diagnosis described herein. Samples obtained from such subject are likewise suitable for use in the methods of the invention.

Cancers having a cell surface-accessible deNAc SA epitope include those having an at least partially de-N-acetylated ganglioside and/or a protein having a sialic acid modification that contains a deNAc SA epitope. Cancers having de-N-acetylated gangliosides have been described.

The presence of de-N-acetyl sialic acid residues in normal human tissue appears to be transient and very low abundance, being found only in a few blood vessels, infiltrating mononuclear cells in the skin and colon, and at moderate levels in skin melanocytes. It is prevalent only in abnormal cells, such as melanomas, leukemias and lymphomas. Since expression of high levels of deNAc SA antigens (e.g., de-N-acetyl gangliosides) occurs predominantly in cancer cells, immunization with deNAc SA antigens can be used to elicit antibodies that can affect complement-mediated cytotoxicity and antibody-dependent cellular cytotoxicity, and can block tumor growth. In addition, antibodies that are specific for short de-N-acetyl sialic acid oligomers found in some gangliosides can be used therapeutically to effect complement-mediated cytotoxicity and antibody-dependent cellular cytotoxicity, and can block tumor growth and prevent adhesion and invasion of cancer cells in other tissues.

Exemplary cancers presenting a deNAc SA epitope include cancer cells presenting a de-N-acetyl ganglioside containing a de-N-acetyl sialic acid residue (e.g. GM2alpha, GM1alpha, GD1beta, GM1b, GD1c, GD1alpha, GM3, GM2, GM1, GD13, GT13, GT1halpha, GD3, GD2, GD1b, GT1b, GQ1b, Gomegalhalpha, GT3, GT2, GT1c, GQ1c, and GP1c). Of particular interest are gangliosides that contain two or more sialic acid residues linked by alpha 2-8 glycosidic bonds (e.g., GD1c, GT13, GD3, GD1b, GT1b, GQ1b, Gomegalhalpha, GT3, GT1c, GQ1c, and GP1c) in which at least one residue is de-N-acetylated. In some embodiments, the ganglioside that contains two or more sialic acid residues linked by alpha 2-8 glycosidic bonds is a ganglioside other than GD3 and/or other than GM3. In some embodiments, the target of the cancer is a deNAc SA epitope other than one present on a de-N-acetylated ganglioside (e.g., a de-N-acetylated residue of a sialic acid-modified protein).

In one embodiment antibodies that specifically bind a SEAM 3 reactive antigen are used in treatment oc cancers that present a SEAM 3 reactive antigen on an cell surface, including cancers that exhibit an extracellularlly accessible SEAM 3-reactive antigen during cell division. Cancers that present a SEAM 3-reactive antigen, particularly a cell surface SEAM 3-reactive antigen, are particularly amenable to therapy with an antibody having the antigen binding specifity of the monoclonal antibody SEAM 3, including cancers that exhibit an extracellularlly accessible SEAM 3-reactive antigen during cell division.

It should be noted that deNAc SA epitopes and/or SEAM 3-reactive antigens against which cancer therapy is directed may be expressed at higher levels on a cancer cell compared to a non-cancerous cell so as to mitigate damage to normal cells, this is not a limitation of the therapies disclosed herein. For example, where the cancer involves a cell type that can be replenished (e.g., B cell, T cell, or other cell of hematopoietic origin, as in leukemias and lymphomas), binding of anti-deNAc SA epitope antibodies (e.g., SEAM 3) to normal cells can be acceptable since damage to a subject by depleting such cells can be treated (e.g., with drugs to stimulate repopulation of normal cells, e.g., GM-CSF, EPO, and the like).

The methods relating to cancer contemplated herein include, for example, use of deNAc SA antigens as a anti-cancer vaccine or therapy, as well as use of antibodies generated using deNAc SA antigens in anti-cancer vaccines (e.g., by passive immunization) or therapies. The methods are useful in the context of treating or preventing a wide variety of cancers, including carcinomas, sarcomas, leukemias, and lymphomas.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but art not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium. In some embodiments, the subject methods do not include treatment of melanoma (i.e., the cancer is other than melanoma). In other embodiments, the subject methods do not include treatment of lymphoma (i.e., the cancer is other than lymphoma).

In certain embodiments, the methods of the present invention are used to treat cancer cells known to express de-N-acetyl gangliosides include melanomas and some lymphomas. Cancers that overexpress the precursor gangliosides GM3 and GD3 are likely to also express the greatest amount of de-N-acetyl gangliosides on the cell surface.

In one embodiment, the cancer is one that presents a SEAM 3-reactive antigen. Cancers that present a SEAM 3-reactive antigen can be identified by methods known in the art. Exemplary methods of detection and diagnosis are described below.

Where the anti-cancer therapy comprises administration of an antibody that having the antigen-binding specificity of the monoclonal antibody (mAb) SEAM 3 (discussed below in detail), the anti-cancer therapy can be particularly directed to dividing (replicating, proliferating) cancerous cells. As shown in the Examples below, the epitope specifically bound by SEAM 3 is primarily accessible during cell division. That is, the level of extracellularly accessible antigen bound by SEAM3 is increased during cell division as compared to non-dividing cells, and binding of SEAM3 drives the cell toward anaphase (into pre-$G_0$). Since most cancers are more rapidly dividing that normal cells of the same type, antibodies that bind a SEAM 3-reactive antigen are attractive for antibody-based cancer therapy.

Thus the present disclosure particularly provides anti-cancer therapy directed toward cancerous cells involving administration of an antibody having the antigen binding specificity of the SEAM 3 mAb. Cancers particularly amenable to antibody therapy using an antibody having the antigen binding specificity of SEAM 3 can be identified by examining markers of cellular proliferation (e.g., Ki-67 antigen) and/or by examining the accessibility of the deNAc SA epitope bound by SEAM 3 in dividing cells (e.g., as in an in vitro assay).

Antibodies having Antigen Binding Specificty of SEAM 3 Monoclonal Antibidy

The disclosure provides recombinant monoclonal antibodies (mAbs), and nucleic acid encoding such antibodies, wherein the recombinant mAbs have the antigen specificity of SEAM3, which MAb binds to de-N-acetylated gangliosides on the surface of cancer cells, and facilitates reduction of cell viability of cancer cells. Recombinant antibodies having the antigen binding specificity of SEAM3 include antibodies having at least an antigen binding portion of SEAM3. Such recombinant mAbs can be described as having the following general characteristics:

a) high affinity for a deNAc SA epitope, particularly a deNAc SA epitope on an extracellullary accessible surface of a cancerous cell (e.g., a $K_d$ of about $10^{-6}$, about $10^{-8}$ or less;

b) slow off rate for dissociation with a deNAc SA antigen (e.g., a $K_{off}$ of about $1\times10^{-3}$ $sec^{-1}$ or less);

c) does not significantly bind to polysialic acid that does not contain de-N-acetyl residues;

d) activity in facilitating loss of adherence of cancerous cells having a cell surface deNAc SA epitope (e.g., a de-N-acetylated ganglioside) in vitro; and e) activity in facilitating reduction of viability of a cancerous cell having cell surface deNAc SA epitope or particularly SEAM 3-reactive antigen, which antibody may disrupt the cell cycle and/or be capable of binding complement and/or direct ADCC against the cancer cell to which it is bound.

Antibodies having the antigen binding specificity of SEAM 3 can be produced by immunization-based techniques, and screening for antibodies that competitively bind SEAM 3 reactive antigen. Such antibodies can also be generated by recombinant methods, using the information provided by the amino acid and encoding polynucleotides of the SEAM 3 mAb heavy chain polypeptide and light chain polypeptide disclosed herein. For example, antibodies having the antigen binding specificity of SEAM 3 can be generated by producing a recombinant light chain polypeptide comprising CDR1, CDR2 and CDR3 of the variable reagion of a SEAM 3 light chain polypeptide (contiguous amino acid residues 24 to 39, contiguous amino acid residues 55 to 61, and contiguous amino acid residues 94 to 100, respectively set forth in FIG. 52) and producing a heavy chain polypeptide comprising CDR1, CDR2, and CDR3 of the variable region of the SEAM 3 heavy chain polypeptide (contiguous amino acid residues 26 to 35, contiguous amino acid residues 50 to 66, and contiguous amino acid residues 101 to 108, respectively, set forth in FIG. 52). Theses CDRs can be provided in a light chain polypeptide and heavy chain polypeptide, respectcively, flanked by appropriate framework residues to provide for formation of an antigen binding site having the antigen binding specificity of SEAM 3. Such antibodies can take any of a variety of forms, including F(ab) fragments, single chain antibodies, chimeric antibodies, humanized antibodies, and the like.

Methods for measuring binding affinity, off rate and other antibody binding kinetics are well known in the art, and may be employed to determine whether an antibody has a high affinity and a slow off rate for a deNAc SA antigen. In many methods and as is well known in the art, antibody binding kinetics may be measured by ELISA methods or by measuring surface plasmon resonance using, for example, a BIA-CORE™ biosensor (Pharmacia/Pfizer) or differential scanning calorimetry (Bliznukov et al. 2001 Biochemistry (Mosc) 66:27-33). Methods for measuring binding of antigens to antibodies using surface plasmon resonance are well known in the art (see, e.g., Methods of Dev. Biol. 2003 112:141-51 and J. Mol. Recognit. 1999 12:310-5) and are readily adapted for use herein.

In certain embodiments a recombinant monoclonal antibody having a antigen-binding characteristics of SEAM3 MAb has a heavy chain having an amino acid sequence that is substantially identical (e.g., at least about 70%, at least about 80%, at least about 90%, at least about 95% or at least about 98% identical) to that of a contiguous sequence of the SEAM3 heavy chain variable domain, and a light chain that is substantially identical (e.g., at least about 70%, at least about 80%, at least about 90%, at least about 95% or at least about 98% identical) to a contiguous sequence of the SEAM3 light chain variable domain. In particular embodiments, a recombinant antibody has framework or CDR amino acid sequences that are substantially identical (e.g., at least about 70%, at least about 80%, at least about 90%, at least about 95% or at least about 98% identical) to a contiguous framework sequence or a contiguous CDR sequence of any of the heavy or light chain sequences shown in FIGS. 46 and 47. Such polypeptides are useful in constructing chimeric antibodies having antigen-binding specificity of SEAM 3. Such contiguous sequences can include the CDRs of the light chain polypeptides (L-CDR1, L-CDR2, L- CDR3) and/or heavy chain polypeptides (H-CDR1, H-CDR2, H- CDR3).

In certain embodiments, recombinant monoclonal antibodies contain a heavy or light chain that is encoded by a polynucleotide that hybridizes under high stringency conditions to a SEAM3 heavy or light chain-encoding nucleic acid. High stringency conditions include incubation at 50° C. or higher in 0.1×SSC (15 mM saline/0.15 mM sodium citrate). Such polynucleotides are useful in detection of SEAM 3 antibody production in a cell, as well as in constructing chimeric antibodies having antigen-binding specificity of SEAM 3.

In certain embodiments, recombinant monoclonal antibodies of the invention may contain a heavy or light chain that is encoded by a polynucleotide having a nucleotide sequence that is at least 80% identical to (e.g., at least 85%, at least 90%, at least 95%, at least 98%) to a contiguous sequence of a SEAM3 heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

The recombinant monoclonal antibody may be a full-length antibody or any chimera thereof, for example. Methods for producing chimeric antibodies are known in the art. See e.g., Morrison et al (Science 1985 229:1202); Oi et al (BioTechniques 1986 4:214); Gillies et al. (J. Immunol. Methods 1989 125:191-202) and U.S. Pat. Nos. 5,807,715, 4,816,567 and 4,816397, which are incorporated herein by reference in their entirety.

The amino acid sequences of the CDRs of the heavy and light chains of SEAM3 are provided in FIG. 52 and framework and CDR regions are defined in FIGS. 53 and 54, for SEAM3 light and heavy chains respectively.

The disclosure also provides antibodies that are modified by conjugation to a moiety that can provide for a desired characteristic (e.g., increase in serum half-life, anti-cancer activity, etc.). Such antibody conjugates are exemplified below.

Modified Antibodies Having Antigen Binding Specificity of SEAM3

The above-described recombinant monoclonal antibodies having an antigen binding region of SEAM3 may be modified to provide modified antibodies that bind a deNAc SA epitope, and have a desired activity, e.g., enhanced ability to facilitate reduction of cancer cell viability, enhanced serum half-life, reduced immunogenicity, and the like. The modified antibodies may be made by substituting, adding, or deleting at least one amino acid of an above-described SEAM3 monoclonal antibody. In one embodiment, the SEAM3 antibody is modified to provide a humanized antibody for human therapeutic use, or another type of modified antibody. In general, these modified antibodies have the general antigen-binding characteristics of the SEAM3 antibody, and contain at least the CDRs of a SEAM3 antibody heavy chain polypeptide and a SEAM3 light chain polypeptide.

Guidance for amino acid substitutions that may be made can be found in the accompanying FIGS. 52, 53 and 54 which illustrate the sequences and positions of the CDRs in the heavy and light chain polypeptides and encoding DNA sequences of SEAM3. For example, in some embodiments, variants can be generated by making amino acid changes (e.g,. substitutions, particularly conservative amino acid substitutions) in the areas outside the CDRs so identified. Further guidance for amino acid substitutions can be found by aligning the amino acid sequences of other anti-deNAc SA epitope antibodies with that of SEAM3, and noting regions that are conserved or variable, and making changes in the variable regions that lie outside the CDRs.

In particular embodiments, these methods include making one or more amino acid substitutions (e.g., one, up to two, up to three, up to four or up to five of more, usually up to 10 or more). An amino acid substitution may be at any position, and the amino acid at that position may be substituted by an amino acid of any identity. Preferably, a modified antibody has the same general characteristics of the SEAM3 MAb. In one embodiment, after a substitutable position has been identified by alignment of the sequences provided herein with the sequences of other antibodies, the amino acids at that position may be substituted. In particular embodiments, an amino acid substitution may be a humanizing substitution (i.e., a substitution that make the amino acid sequence more similar to that of a human antibody), a directed substitution (e.g., a substitution that make the amino acid sequence of an antibody more similar to that of a related antibody in the same group), a random substitution (e.g., a substitution with any of the 20 naturally-occurring amino acids) or a conservative substitution (e.g., a substitution with an amino acid having biochemical properties similar to that being substituted).

In certain embodiments, modified antibodies of the invention may contain a heavy or light chain that is encoded by a polynucleotide that hybridizes under high stringency conditions to a SEAM3 heavy or light chain-encoding nucleic acid, particularly to the fragments encoding CDR1, CDR2 and CDR3 of the variable region of a SEAM 3 light chain polypeptide (contiguous amino acid residues 24 to 39, continguous amino acid residues 55 to 61, and contiguous amino acid residues 94 to 100, respectively set forth in FIG. 52) and to fragments encoding CDR1, CDR2, and CDR3 of the variable region of the SEAM 3 heavy chain polypeptide (contiguous amino acid residues 26 to 35, contiguous amino acid residues 50 to 66, and contiguous amino acid residues 101 to 108, respectively, set forth in FIG. 52). High stringency conditions include incubation at 50° C. or higher in 0.1×SSC (15 mM saline/0.15 mM sodium citrate).

In certain embodiments, modified antibodies of the invention may contain a heavy or light chain that is encoded by a polynucleotide that is at least 80% identical to (e.g., at least 85%, at least 90%, at least 95%, at least 98%) the contiguous SEAM3 heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

Humanized Antibodies

In one embodiment, the invention provides humanized versions of the SEAM3 monoclonal antibody. In general, humanized antibodies can be made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539;

5,530,101; and 5,585,089), veneering or resurfacing (EP 592, 106; EP 519,596; Padlan, Molecular Immunology 28(4/5): 489-498 (1991); Studnicka et al., Protein Engineering 7(6): 805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, the SEAM3 antibody may be humanized according to the methods set forth in published U.S. published patent application nos. 20040086979 and 20050033.031. Accordingly, the SEAM3 antibody described above may be humanized using methods that are well known in the art.

A humanized SEAM3 antibody therefore may contain the unaltered CDRs of the SEAM3 antibody, or, in certain embodiments, altered CDRs of the SEAM3 antibody. A humanized antibody containing altered CDRs of the SEAM3 antibody generally contains CDRs having 1, up to 2, up to 3, up to 4, up to 5, up to 6, up to 7 and in certain cases up to about 10 amino acid substitutions, as compared to the CDRs of the SEAM3 antibody. The particular substitutable positions of a CDR, as well as the donor amino acid that can be substituted into those positions, can be determined by alignment of the nucleic acid and/or amino acid sequences of SEAM3 provided herein with that of other antibodies.

Polyethylene Glycol (PEG)-Modified Antibodies

Anti-deNAc SA epitope antibodies contemplated herein include PEGylated anti-deNAc SA epitope antibodies, with PEGylated recombinant anti-deNAc SA epitope antibodies having antigen specificity of SEAM3 being of particular interest. Methods and reagents suitable for PEGylation of an antibody are well known in the art. In general, PEG suitable for conjugation to an antibody is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

In many embodiments, PEG has at least one hydroxyl group, e.g., a terminal hydroxyl group, which hydroxyl group is modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

In other embodiments, PEG is derivatized so that it is reactive with free carboxyl groups in the antibody polypeptide, e.g., the free carboxyl group at the carboxyl terminus of the antibody polypeptide. Suitable derivatives of PEG that are reactive with the free carboxyl group at the carboxyl-terminus of a heavy chain or light chain polypeptide include, but are not limited to PEG-amine, and hydrazine derivatives of PEG (e.g., PEG-NH—NH$_2$).

In other embodiments, PEG is derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the ε-amino groups in lysine residues are protonated and remain non-nucleophilic. On the other hand, reactions under suitable pH conditions may make some of the accessible lysine residues to react with selectivity.

In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-NH$_2$ groups of lysine may also react.

The PEG can be conjugated directly to an amino acid residues of the antibody, or through a linker. In some embodiments, a linker is added to an antibody polypeptide, forming a linker-modified antibody polypeptide. Such linkers provide various functionalities, e.g., reactive groups such sulfhydryl, amino, or carboxyl groups to couple a PEG reagent to the linker-modified antibody polypeptide.

In some embodiments, the PEG conjugated to the antibody polypeptide is linear. In other embodiments, the PEG conjugated to the antibody polypeptide is branched. Branched PEG derivatives such as those described in U.S. Pat. No. 5,643, 575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG having a molecular weight in a range of from about 2 kDa to about 100 kDa, is generally used, where the term "about," in the context of PEG, indicates that in preparations of polyethylene glycol, some molecules will weigh more, some less, than the stated molecular weight. For example, PEG suitable for conjugation to antibody has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

Preparing PEG-Antibody Conjugates

As discussed above, the PEG moiety can be attached, directly or via a linker, to an amino acid residue at or near the N-terminus, internally, or at or near the C-terminus of the antibody polypeptide. Conjugation can be carried out in solution or in the solid phase.

N-Terminal Linkage

Methods for attaching a PEG moiety to an amino acid residue at or near the N-terminus of an antibody polypeptide are known in the art. In some embodiments, known methods for selectively obtaining an N-terminally chemically modified antibody are used. For example, a method of protein modification by reductive alkylation which exploits differential reactivity of different types of primary amino groups (lysine versus the N-terminus) available for derivatization in a particular protein can be used. Under the appropriate reaction conditions, substantially selective derivatization of the protein at the N-terminus with a carbonyl group containing polymer is achieved. The reaction is performed at pH which allows one to take advantage of the $pK_a$ differences between the ε-amino groups of the lysine residues and that of the α-amino group of the N-terminal residue of the protein. By such selective derivatization attachment of a PEG moiety to the antibody is controlled: the conjugation with the polymer takes place predominantly at the N-terminus of the antibody and no significant modification of other reactive groups, such as the lysine side chain amino groups, occurs.

C-Terminal Linkage

MonoPEGylation can be accomplished by using a PEG reagent that is selective for the C-terminus of a polypeptide, which can be prepared with or without spacers. For example, polyethylene glycol modified as methyl ether at one end and having an amino function at the other end may be used as the starting material.

Preparing or obtaining a water-soluble carbodiimide as the condensing agent can be carried out. Coupling antibody with a water-soluble carbodiimide as the condensing reagent is generally carried out in aqueous medium with a suitable buffer system at an optimal pH to effect the amide linkage. A high molecular weight PEG can be added to the protein covalently to increase the molecular weight.

The reagents selected will depend on process optimization studies. A non-limiting example of a suitable reagent is EDC or 1-ethyl-3-(3-dimethylaminopropyl)carbodiimide. The water solubility of EDC allows for direct addition to a reaction without the need for prior organic solvent dissolution.

Even though the use of PEG amine has been mentioned above by name or structure, such derivatives are meant to be exemplary only, and other groups such as hydrazine derivatives as in PEG-NH—$NH_2$ which will also condense with the carboxyl group of the antibody protein, can also be used. In addition to aqueous phase, the reactions can also be conducted on solid phase. Polyethylene glycol can be selected from list of compounds of molecular weight ranging from 300-40000. The choice of the various polyethylene glycols will also be dictated by the coupling efficiency and the biological performance of the purified derivative in vitro and in vivo i.e., circulation times, anti viral activities etc.

Additionally, suitable spacers can be added to the C-terminal end of the antibody heavy chain and/or light chain protein. The spacers may have reactive groups such as SH, $NH_2$ or COOH to couple with appropriate PEG reagent to provide the high molecular weight Antibody derivatives. A combined solid/solution phase methodology can be devised for the preparation of C-terminal pegylated antibody polypeptides.

If desired, PEGylated antibody is separated from unPEGylated antibody using any known method, including, but not limited to, ion exchange chromatography, size exclusion chromatography, and combinations thereof.

Antibody-Fusion Proteins

The invention also contemplates recombinant antibodies having the antigen specificity of a SEAM3 MAb, where the antibody is modified to include a heterologous protein. For example, a SEAM3 heavy chain polypeptide or SEAM3 light chain polypeptide may be joined to a reporter protein or to a protein having a desired anti-cancer effect. For example, SEAM3 may be conjugated to a second antibody (or at least an antigen-binding portion thereof), e.g., an antibody that specifically binds an angiogenic or proliferative factor, such as an antibody that is directed against vascular enthothelial growth factor (VEGF), which is key mediator of angiogenesis, where SEAM3 targets the conjugate to specific cancer cells and the anti-VEGF antibody inactivates VEGF thus inhibiting angiogenesis.

In one embodiment, the invention provides a CDR of a SEAM3 light chain polypeptide or a CDR of a heavy chain SEAM3 polypeptide which is linked to a heterologous polypeptide, i.e., is linked to a polypeptide to which it is not normally associated in the native SEAM3 antibody. Methods for producing a fusion protein of interest when provided a nucleic acid sequence are well known in the art.

Methods for Producing Recombinant Antibodies

In many embodiments, the nucleic acids encoding a SEAM3 monoclonal antibody, or at least a CDR of a SEAM3 heavy chain polypeptide or at least a CDR of a SEAM3 light chain polypeptide, are introduced directly into a host cell, and the cell incubated under conditions sufficient to induce expression of the encoded antibody. Accordingly, the invention also contemplates recombinant host cells containing an exogenous polynucleotide encoding at least a CDR of a SEAM3 heavy chain polypeptide or at least a CDR of a SEAM3 light chain polypeptide.

Any suitable host cell, vector and promoter can be used in connection with the SEAM3-encoding nucleic acids of the invention. Of particular interest are vectors having an insert encoding at least a CDR of a SEAM3 heavy chain polypeptide and/or at least a CDR of a SEAM3 light chain polypeptide. Also of interest are polynucleotides that are composed of a nucleic acid sequence encoding at least a CDR of a SEAM3 heavy chain polypeptide or at least a CDR of a SEAM3 light chain polypeptide, where the SEAM3-encoding sequence is operably linked to a heterologous promoter. Exemplary host cells, vectors, and promoters will now be described in more detail.

Any cell suitable for expression of expression cassettes may be used as a host cell. For example, yeast, insect, plant, etc., cells. In many embodiments, a mammalian host cell line that does not naturally produce antibodies, e.g., mammalian cells that are not hybridoma cells, B cells, or spleen cells. It may also be of interest to use cells that provide for altered glycosylation of the recombinant antibody, or which lack glycosylation. Exemplary cells include, but are not limited to: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see, e.g., Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In embodiments of particular interest, the antibody is typically secreted into the supernatant of the media in which the cell is cultured.

Once a recombinant antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Kits

Also provided by the invention are kits for practicing the methods disclosed herein, as described above. The kits can include one or more of, depending upon the intended use of the kit, the compositions described herein, such as: a deNAc SA antigen, cells suitable for use in the biosynthetic methods of de-N-acetylated PS production (optionally, with the acyl mannosamine and trihaloacyl mannosamine reagents described in the methods above), an anti-deNAc SA epitope antibody, a nucleic acid encoding the same (especially a nucleic acid encoding a CDR of a heavy and/or light chain of SEAM3 MAb), or a recombinant cell containing the same. Other optional components of the kit include: buffers, etc., for administering the anti-deNAc SA epitope antibody or deNAc SA antigen, and/or for performing a diagnostic assay. The recombinant nucleic acids of the kit may also have restrictions sites, multiple cloning sites, primer sites, etc to facilitate their ligation to constant regions of non-SEAM3 encoding nucleic acids. The various components of the kit may be present in separate containers or certain compatible components may be precombined into a single container, as desired.

In addition to above-mentioned components, the subject kits typically further include instructions for using the components of the kit to practice the disclosed methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention are kits including at least a computer readable medium including programming as discussed above and instructions. The instructions may include installation or setup directions. The instructions may include directions for use of the invention with options or combinations of options as described above. In certain embodiments, the instructions include both types of information.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Preparation of N-Acyl NmB PS and Derivatives Having a deNAc SA Epitope

N-acyl *Neisseria meningitidis* Group B (NmB) polysaccharide (PS) (acyl=acetyl [Ac] or propionyl [Pr]) was prepared by the method of Guo and Jennings, with differences as noted below (Guo, Z. and Jennings, H. in 2001. N-Propionylation. In Meningococcal Vaccines: Methods and Protocols. A. J. Pollard, and C. J. M. Maiden, eds. Humana Press Inc., Totowa, N.J., p. 55.) as follows to produce PS derivatives having a deNAc SA epitope. Colominic acid or NmB PS (100 mg; EY Laboratories, Inc., San Mateo, Calif.) and 10 mg of sodium borohydride (Sigma-Aldrich) was dissolved in 10 ml of 2M NaOH and heated to 90° C. in a sealed tube (Pierce Chemical Co., Rockford, Ill.) for 2 h.

The conditions of the de-N-acetylation reaction differ from those described by Guo and Jennings. Instead of producing a completely de-N-acetylated PS derivative as described by Guo and Jennings, the product typically contained 20% N-acetyl residues as determined by resorcinol assay described below. Also, heating the solution to 100° C. and above and hydolysis times longer than 2 h results in degradation of the polysaccharide and production of undefined, undesirable side products. FIG. 1 provides the structure of an exemplary de-N-acetylated PS.

The approach described herein has advantages for preparing PS derivatives containing a mixture of N-acetyl and N-acyl residues (e.g. N-propionyl, N-butanoyl, etc.), as well as for preparing PS derivatives containing a mixture of N-acetylated and de-N-acetylated residues, since it provides that a minimum of about 20% of the residues were de-N-acetylated. Also, the addition of sodium borohydride reduces the ketone at the reducing end of the PS to an alcohol and also, an imine that could be formed between the de-N-acetylated amino group and the C2 ketone of the reducing end residue to a secondary amine. NmB PS derivatives containing residues with N-acetyl groups, de-N-acetyl sites, and a cyclic secondary amine at the reducing end residue were bound by the non-autoreactive, anti-N—Pr NmB PS mAb SEAM 3 (see Example 3, below) and, therefore, are important antigens for eliciting antibodies that are reactive with de-N-acetyl sialic acid antigens (in particular in polymers of alpha (2→8) N-acetyl neruaminic acid) that are expressed in cancer cells.

After cooling the solution to ambient temperature, the solution was adjusted to pH 8.0 with 2 M HCl or glacial acetic acid, dialyzed against water, and lyophilized. was re-acylated as described below without further purification.

Free amino groups were acylated by resuspending the PS (~100 mg) in 3-5 ml of water and adjusting the pH to 8-9 by adding 0.1 M NaOH and adding 0.5 ml of acyl anhydride (e.g., acetic acid anhydride or propionic acid anhydride) in 5 aliquots with stirring over several hours. (Acetic anhydride was not included in the derivatives previously prepared by Guo and Jennings.) Alternatively, the carboxylic acid was activated by combining 0.5 ml of the acid with 1 equivalent of 1-Ethyl-3-[3-dimethylaminopropyl]carbodiimide hydrochloride (EDC, Pierce Chemical Company, Rockford, Ill.). A small amount of water (approximately 1 ml) was added to completely dissolve the EDC. As with the anhydrides, the carbodiimide-activated carboxylic acid was added in 5 equal aliquots over several hours with stirring. In some applications, such as in preparing derivatives for use in conjugating to a carrier protein, for example N-acryl, -methacryl, -bromoacetyl (BrAc)or -chloroacetyl (ClAc), as described below, the amount of carboxylic acid was reduced to a fraction of the amount of fee amine in the polysaccharide (e.g. 10% to 90%) as determined by resorcinol assay (as described below). The advantage of using the EDC-activated acylating reagents is that they do not hydrolyze as rapidly in water as the anhydrides or acyl chlorides and react more selectively with amines. This permits better control over the fraction of amino groups acylated. Since hydrolysis is slower, large fluctuations in pH, which can result in extensive hydrolysis of N-acryl, BrAc, and ClAc groups, are avoided. The pH of the solution was maintained at ~8-9 by adding 2 M NaOH as required. The solution was dialyzed and lyophilized.

Although most of the amino groups were acylated in this procedure (80%-90%), some amino groups were not derivatized and remain free amino groups. PS containing residues with de-N-acetyl sites, including at the non-reducing end of the polymer was bound by SEAM 3 (see Example 3, below) and is, therefore, an important determinant for eliciting protective, non-autoreactive anti-NmB capsular antibodies.

Smaller fragments of the PS (average degree of polymerization [Dp]<20) were produced by hydrolysis in water at acidic pH. A portion of the N-acyl NmB PS (20 mg) was dissolved in 5 ml of 20 mM NaOAc, pH 5.5 and heated to 50° C. in a sealed tube for 1-24 h, typically 5 h, depending on the size of the fragments desired. The solution was dialyzed and lyophilized.

Figure 2:
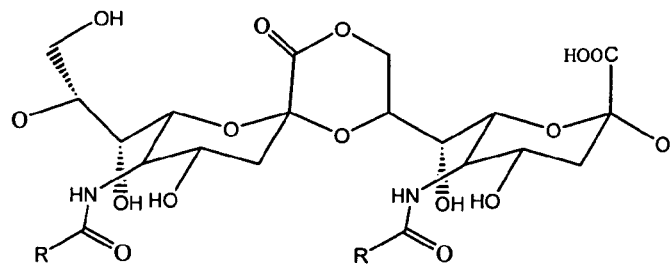
FIG. 2 provides the structure of a lactone moiety formed between the C1 carboxyl group and the C9 hydroxyl group of the preceding residue in NmB PS following acid treatment of NmB PS.

In addition to producing PS having a Dp that is on average smaller than that of the starting PS, acid treatment results in the formation of lactones between the C1 carboxyl group and the C9 OH group of the preceding residue (FIG. 2). PS containing small amounts of lactone may occur in sialic acid antigens expressed in cancer cells. The presence of small amounts of lactone in NmB PS derivative preparations may facilitate eliciting antibodies that are reactive with deNAc SA antigens expressed on the surface of cancer cells.

Figure 3:
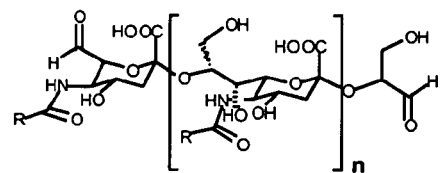
FIG. 3 provides the structure of a PS derivative having an aldehyde group at the non-reducing end terminal residue.

Aldehyde groups were introduced into the non-reducing and reducing ends of the PS for use in covalent attachment to a carrier protein. The. PS (20 mg) was dissolved in 1 ml of 0.1 M NaOAc buffer, pH 6.5. Sodium meta periodate (5 mg, Sigma-Aldrich) was added and the solution kept in the dark for 30 min. The remaining NaIO4 was degraded by adding 0.1 ml of 10% (wt/vol) ethylene glycol in water and left for 30 min. This procedure produces aldehyde groups at C8 and/or C7 of the non-reducing end terminal residue and, for PS that contains a reducing end terminal residue in which the C2 ketone was reduced to an alcohol during de-N-acetylation (see above), an aldehyde group on C7 (FIG. 3).

Some fraction of de-N-acetyl residues were also oxidized to aldehydes using periodate since the C5 amino group is vicinal to the C4 hydroxyl group. To minimize destruction of de-N-acetyl SA residues, which are epitopes recognized by SEAM 3, by periodate, N-Acryl, -BrAc, or -ClAc groups were alternatively introduced into N—Pr and N—Ac NmB PS that contained de-N-acetyl residues as the result of de-N-acetylation and incomplete re-acylation. The carboxylic acid groups were activated with EDC as described above. Only a fraction of the free amines present in the PS were acylated (10%-90%) by limiting the amount of activated carboxylic acid added to the reaction. The acryl, BrAc, and ClAc groups are reactive with thiols and amino groups present in carrier proteins under mild conditions and thus, the PS derivatives can be conjugated to a carrier protein without the oxidative damage caused by treatment of the PS with periodate.

Preparation of Dodecylamine and Protein-PS Derivative Conjugates

Dodecylamine derivatives were prepared by combining 20 milligrams of NmB PS derivative containing non-reducing end or reducing end aldehydes or ketones with 10 milligrams of dodecylamine in 5 milliliters of water. After heating the mixture to about 50 degrees C. for 30 minutes with stirring, 5 mg of sodium cyanoborohydride was added. The mixture was stirred at ambient temperature for 24 hours then dialyzed in water for 3 to 5 days to remove excess dodecylamine.

The reactivity of the dodecylamine derivatives with SEAM mAbs was determined by direct binding ELISA in which the antigen (i.e. the dodecylamine PS derivative) was absorbed to the surface of a microtiter plate by incubating a solution of the antigen in PBS buffer in the well of a microtiter plate overnight at 4 degrees C. The plates were washed with PBS buffer (5×) and blocked with PBS buffer containing 1% (weight/weight) of bovine serum albumin (Sigma; blocking buffer) for 1 hour at ambient temperature. The antibodies were diluted in blocking buffer and added to the plate (100 microliters per well). After incubating the plate for 4 hours at ambient temperature, the plates were washed with PBS buffer (5×) and rabbit anti-mouse-alkaline phosphatase conjugate antibody (Zymed) diluted in blocking buffer was added. After incubating an additional hour, the plates were washed (5×) with PBS buffer and the bound antibody was detected by adding p-nitrophenyl phosphate substrate in 50 mM sodium carbonate buffer, pH 9, containing 1 mM $MgCl_2$. The absorbance at 405 nm after 30 minutes incubation at ambient temperature was measured using a BioRad Model 550 microtiter plate reader. The results of binding experiments are shown in FIG. 34.

PS derivatives conjugated to a carrier protein were prepared by combining 5 milligrams of bovine serum albumin (BSA, Pierce Chemical Co.) tetanus toxoid with 10 mg of PS derivative or PS derivative containing terminal end aldehyde groups or N-Acryl, BrAc, or ClAc groups in PBS buffer. 5 milligrams of sodium cyanoborohydride (PS containing aldehydes) or nothing (N-Acryl, -BrAc, -ClAc) was added and the mixture was stirred in the dark for 5 days at ambient temperature. The solution was dialyzed (10-14 kDa cutoff membrane) in PBS buffer. The reactivity of the PS derivative-BSA conjugates with mAbs was determined by direct binding ELISA as described in the previous paragraph. The results of binding experiments are shown in FIG. 35.

The concentration of sialic acid and de-N-acetyl sialic acid in NmB PS derivative stock solutions was determined by the Svennerholm resorcinol reaction (Svennerholm, L. (1957) Biochim. Biophys. Acta 24:604) modified as follows. Resorcinol working reagent was prepared by combining 9.75 milliliters of water, 0.25 milliliters of 0.1 M $CuSO_4 \cdot 5H_2O$, 10 milliliters of 20 milligram per milliliter solution of resorcinol in water, and 80 milliliters of concentrated HCl. The resorcinol working reagent (300 microliters) was combined with the sialic acid or de-N-acetyl sialic acid sample solution (up to 50 micrograms of sialic acid) or standard stock solution in water (300 microliters) in a polypropylene deep well (2 milliliter) microliter plate. The plate was sealed with a plate cover and heated in a boiling water bath for 30 minutes. After cooling to ambient temperature, isoamyl alcohol (600 microliters) was added and mixed using a pipette. The phases were allowed to separate and the upper isoamyl alcohol layer was removed to a clean microliter plate. 250 microliters of the isoamyl alcohol extract and the lower aqueous solution were transferred separately to a polystyrene microliter plate and the absorbance at 495 nm and 580 nm was measured.

The amount of N-acetyl sialic acid was determined by from the absorbance of the isoamyl alcohol fraction at 580 nm and the amount of de-N-acetyl sialic acid was determined from the absorbance of the aqueous fraction at 495 nm in comparison to a standard curve for each. The amount of de-N-acetyl sialic acid was corrected for the amount of de-N-acetylation that occurs during the acid hydrolysis step of the assay by measuring the amount of de-N-acetylation that occurs in the sialic acid standard.

Reverse-Phase HPLC purification of NmB PS derivatives containing long Chain alkyl groups. NmB PS derivatives containing long chain (i.e. ≧C8) alkyl groups (e.g. dodecylamine derivatives) were separated by reverse-phase HPLC using a Poros R1/H column and BioCAD Perfusion Chromatography Workstation. Derivatives were eluted with a gradient from 0% to 80% acetonitrile in 20 mM ammonium acetate buffer, pH 6.5 over 30 minutes at a flow rate of 5 milliliters per minute. Fractions (1 milliliter each) were collected.

Fractions containing derivatives that were reactive with mAbs (for example SEAM 3, SEAM 12 Granoff et al. 1998, supra) were determined by adding 100 microliters of each fraction to a well of a 96 well microtiter plate (Immulon II, Dynatech) and incubating the plate at 4 degrees C. overnight. The plates were washed with PBS buffer (5×) and blocked with PBS buffer containing 1% (weight/weight) of bovine serum albumin (Sigma; blocking buffer) for 1 hour at ambient temperature. The antibodies were diluted in blocking buffer and added to the plate (100 microliters per well). After incubating the plate for 4 hours at ambient temperature, the plates were washed with PBS buffer (5×) and rabbit anti-mouse-alkaline phosphatase conjugate antibody (Zymed) diluted in blocking buffer was added. After incubating an additional hour, the plates were washed (5×) with PBS buffer and the bound antibody was detected by adding p-nitrophenyl phosphate substrate in 50 mM sodium carbonate buffer, pH 9, containing 1 mM $MgCl_2$. The absorbance at 405 nm after 30 minutes incubation at ambient temperature was measured using a BioRad Model 550 microtiter plate reader.

Figure 16:
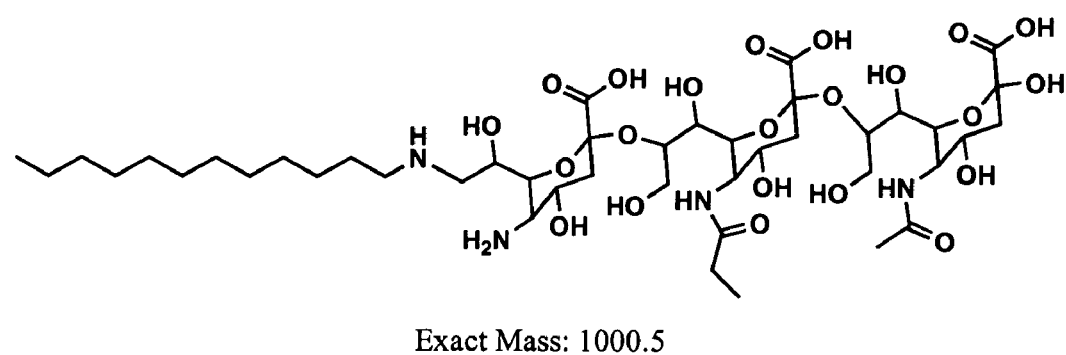
FIGS. 16-18 provide structures of dodecylamine NmB PS derivatives prepared and identified in EXAMPLE 1.
Figure 17:
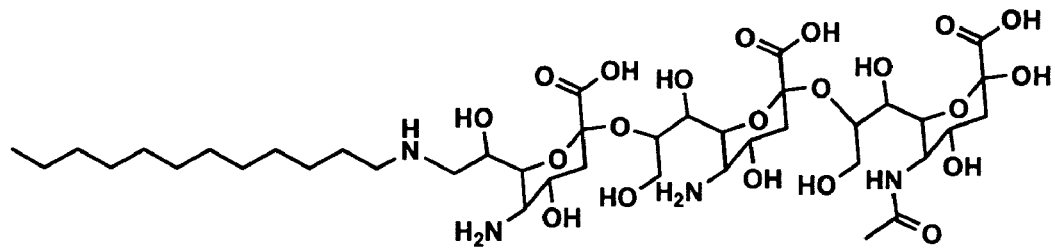
Figure 18:
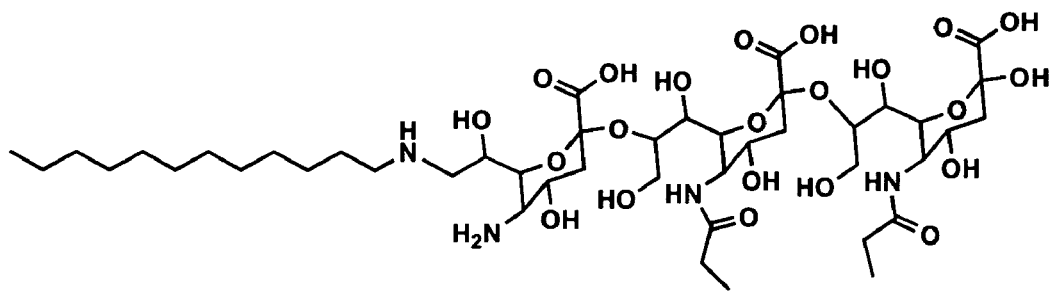
Figure 19:
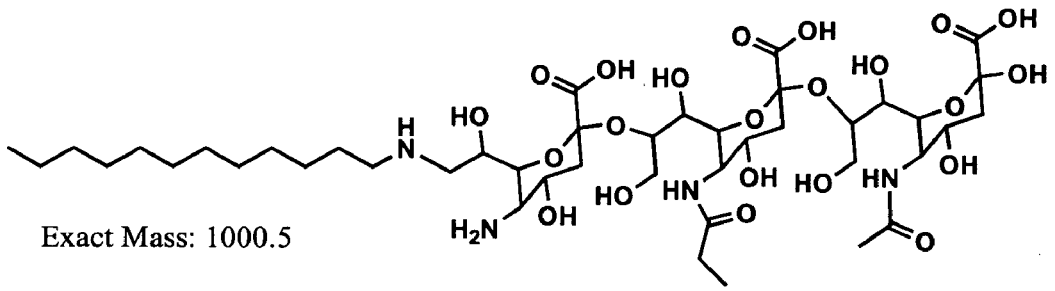
FIGS. 19-33 provide structures of exemplary acyl amine de-N-acetylated PS derivatives of the invention.
Figure 20:
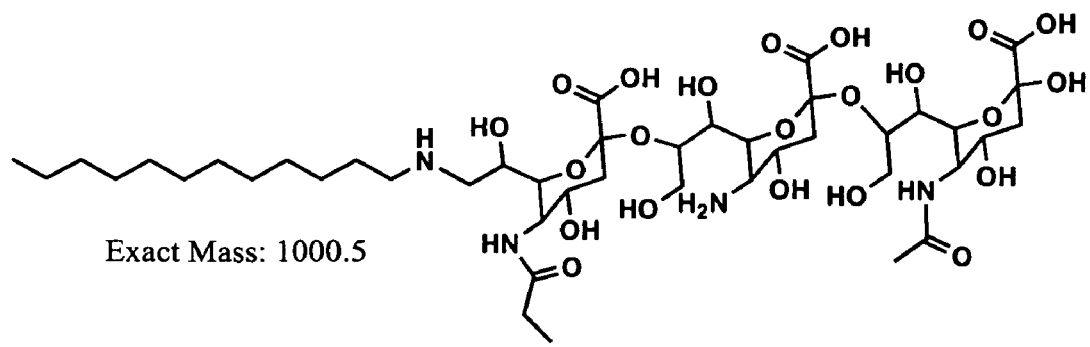
Figure 21:
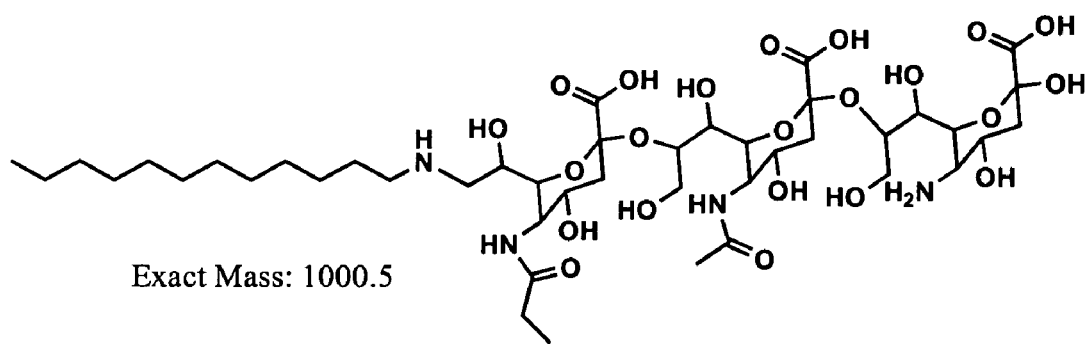
Figure 22:
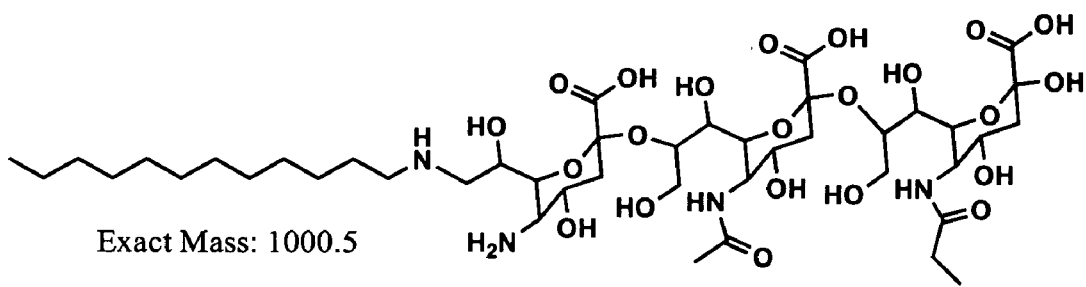
Figure 23:
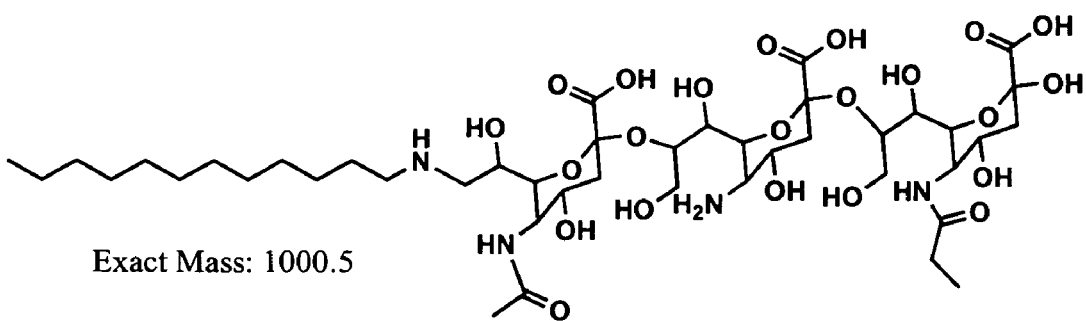
Figure 24:
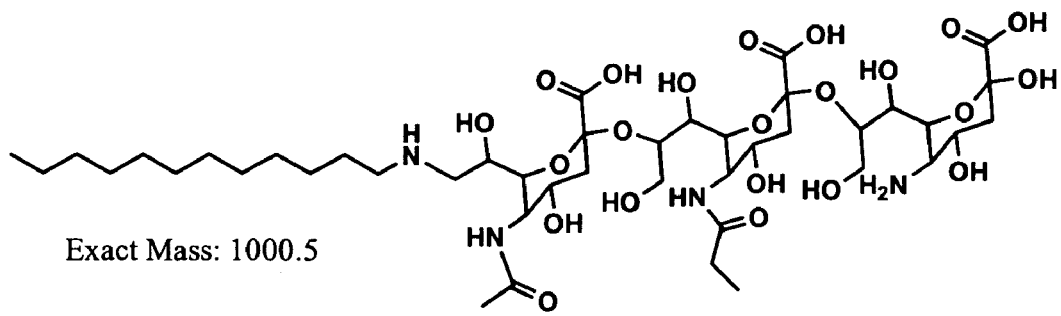
Figure 25:
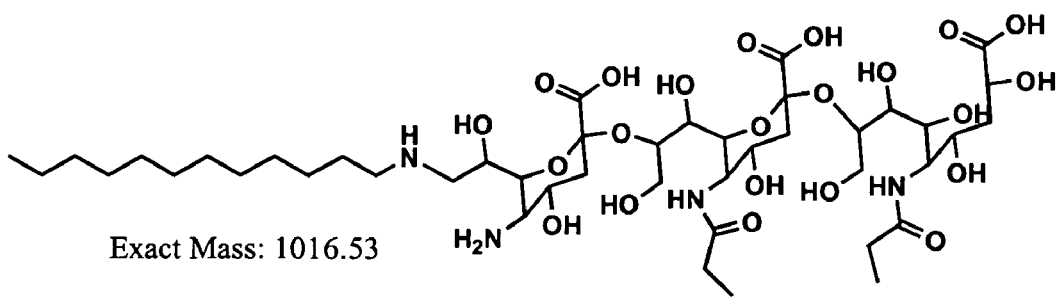
Figure 26:
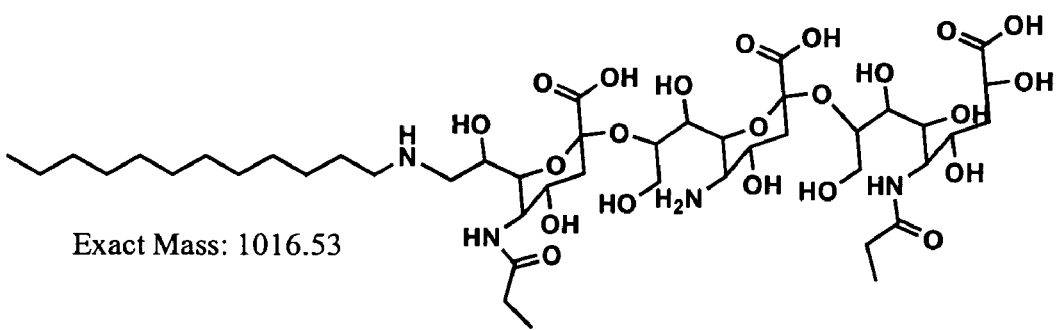
Figure 27:
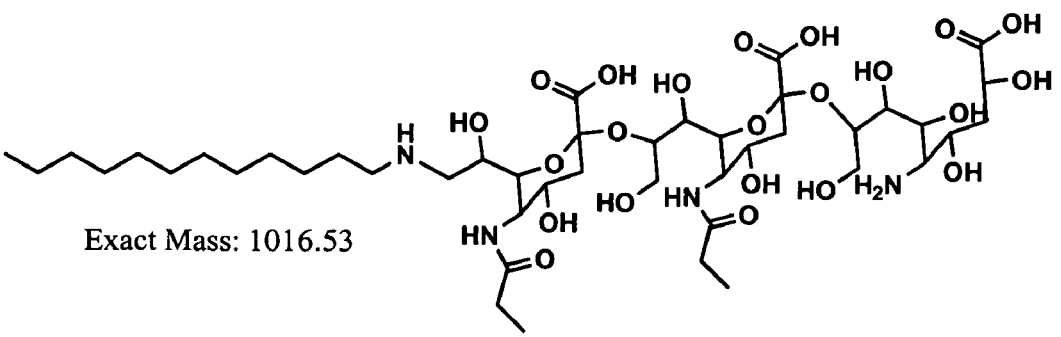
Figure 28:
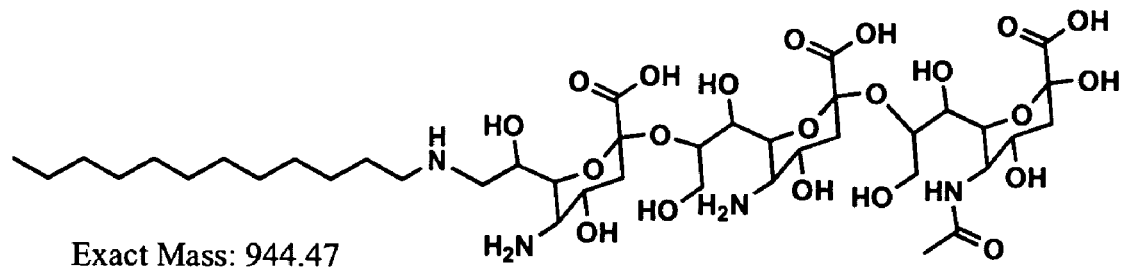
Figure 29:
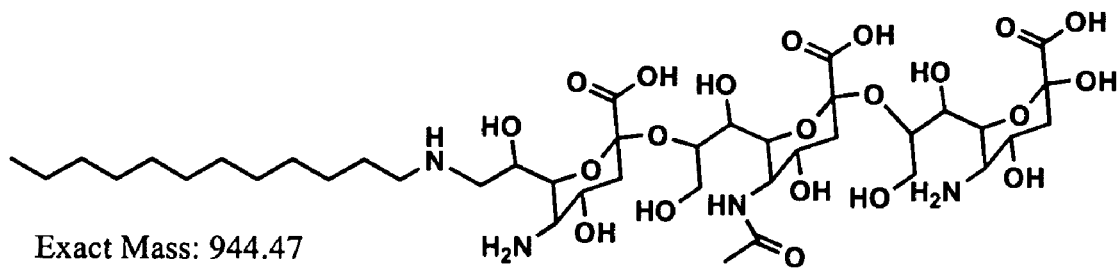
Figure 30:
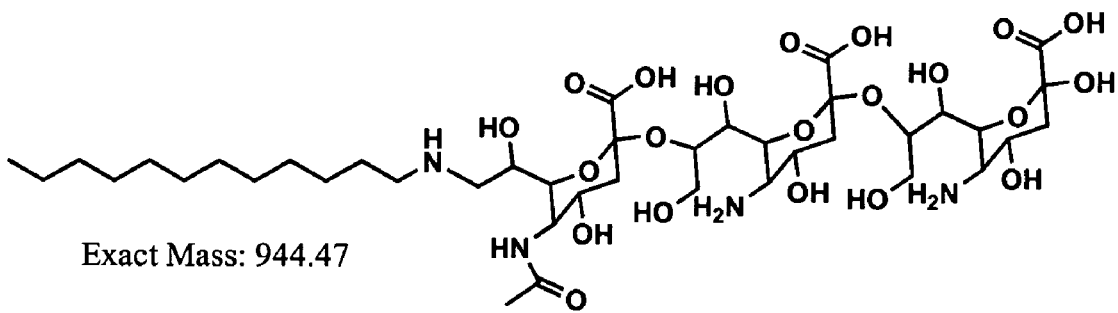
Figure 31:
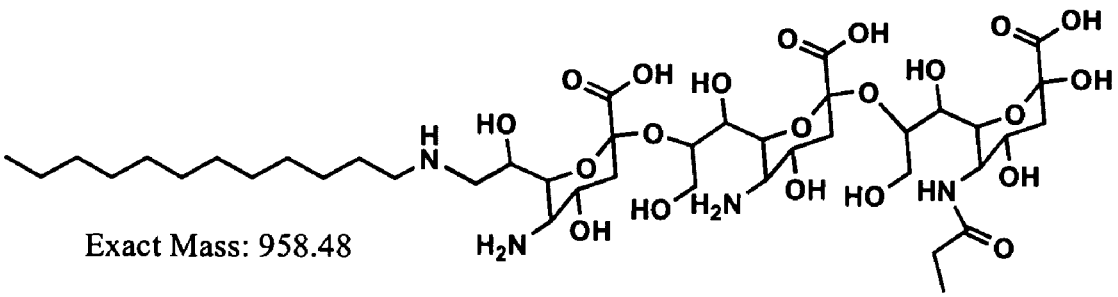
Figure 32:
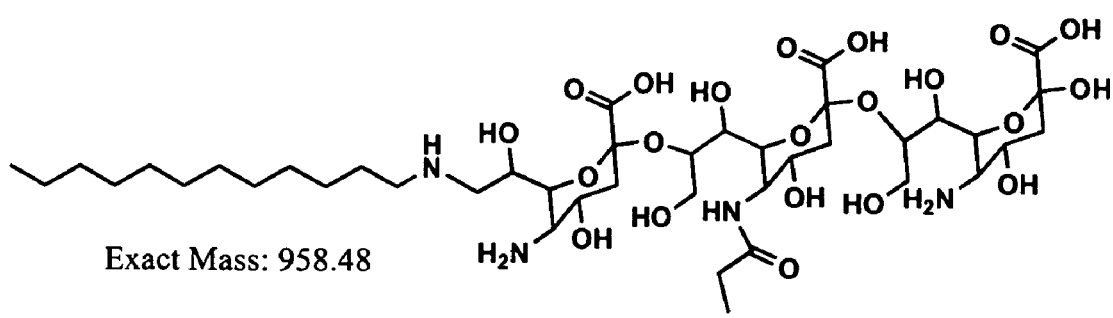
Figure 33:
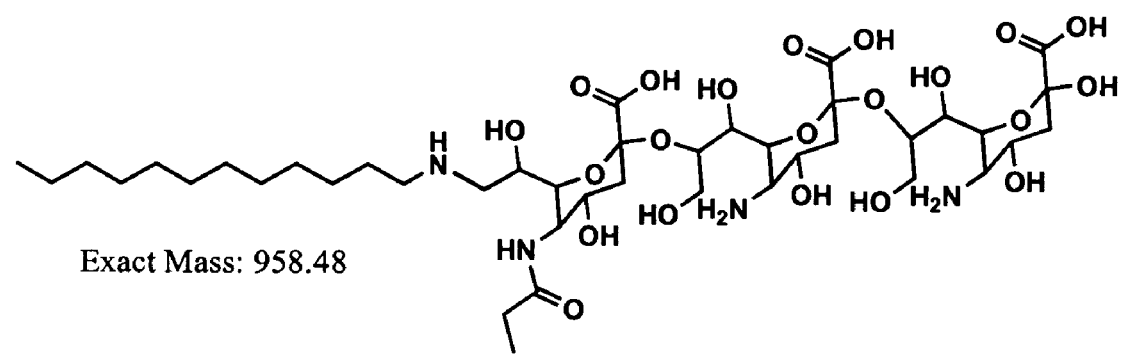
Figure 36:
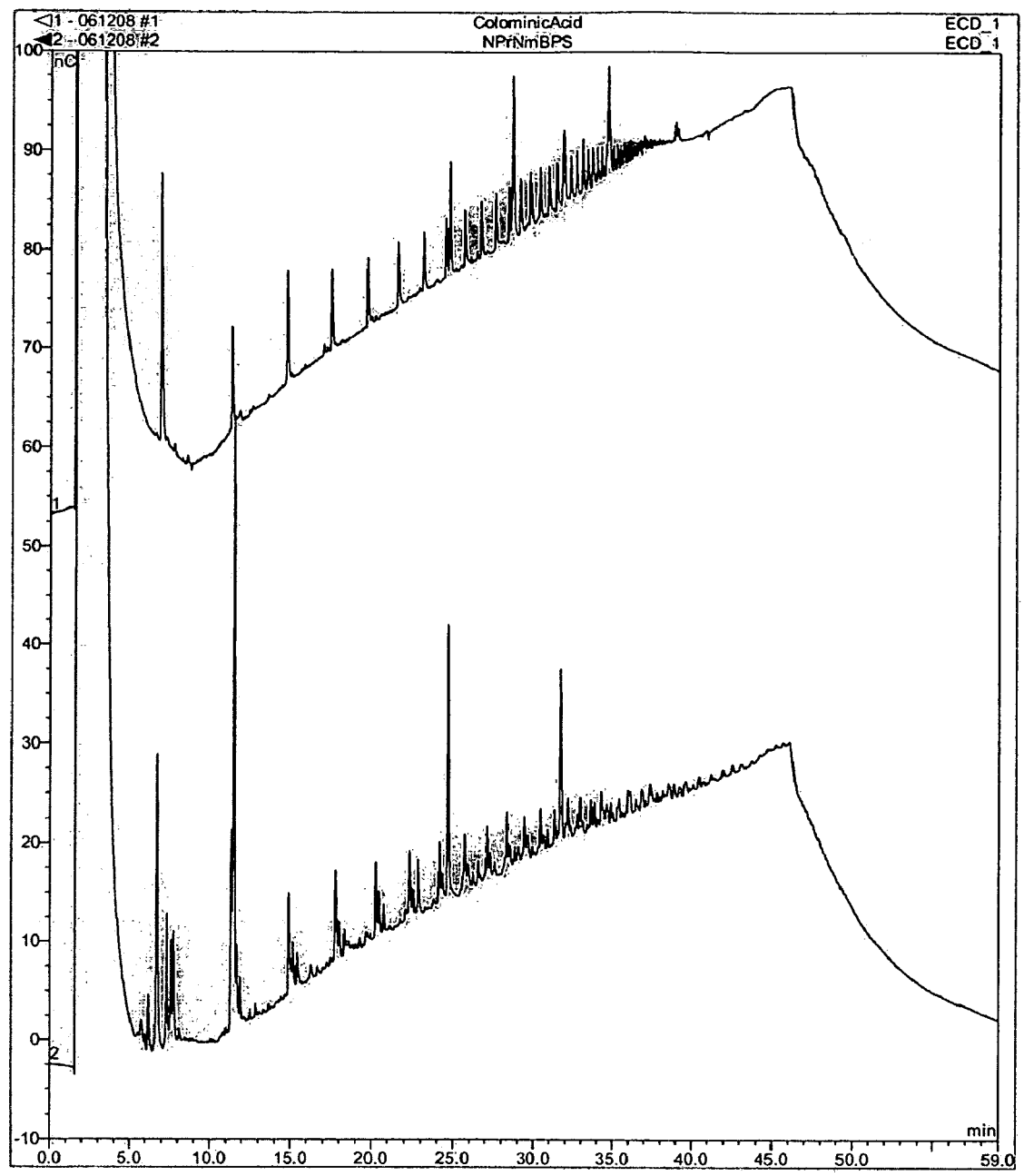
FIG. 36 is a chromatogram from high performance anion exchange chromatography of colominic acid (i.e. poly alpha (2→8) N-acetyl neuraminic acid prepared from *E. coli* K1) (curve number 1) and N-Pr NmB PS that had been exhaustively treated with sialidase A

MALDI-TOF mass spectroscopy of non-reducing end dodecylamine derivatives of NmB PS. The solvent in fractions obtained from reverse-phase HPLC were evaporated using a SpinVac (ThermoSavant). The residue was dissolved in acetonitrile/water (1:1). A matrix of trihydroxyacetophenone (THAP) at a concentration of 3 milligrams per milliliter in acetonitrile/water was spotted onto the target (0.5 microliter per spot). After drying the matrix spots under vacuum, the sample was spotted on top of the matrix spot (0.5 microliters). MALDI-TOF (Autoflex, Bruker Daltonics) was performed in the both positive and negative linear modes (30 shots $N_2$ laser, 50% laser power) and in reflector positive and negative modes (30 shots $N_2$ laser, 50% laser power). The mass spectra were calibrated using external peptide (Bruker Daltonics) and sialic acid (EY Laboratories) standards. The error of the observed masses were estimated to be ≦0.1%. FIGS. 16-18 show structures identified by MALDI-TOF from a preparation of NmB PS that were reactive with protective, non-autoreactive anti-NmB capsular mAb SEAM 3 and purified by reverse-phase HPLC as described above. The derivatives contain a mixture of de-N-acetyl, N-acetyl, and N-propionyl residues with at least one de-N-acetyl residue.

Example 2

Determination of the Structure of NmB PS Derivatives Recognized by SEAM 3 by MALDI-TOF Mass Spectroscopy SEAM 3 was linked to magnetic beads as follows. Magna-Bind™ goat anti-mouse IgG beads (200 µl; Pierce) were combined with 5 µg of SEAM 3 in PBS buffer. The mixture was incubated at ambient temperature on a rotating wheel for 1 hr. The beads were washed 3 times with wash buffer. The bound antibody was cross-linked to the beads by adding $BS^3$™ (Pierce) to a concentration of 2 mM in PBS buffer and mixed by vortexing for 30 min at ambient temperature. Unreacted $BS^3$™ was degraded by adding Tris to 0.1 M, pH 8.0 for 10 min. The beads were washed 3 times with PBS buffer. N—Pr NmB PS (240 micrograms) prepared in Example 1 was added to the washed beads in PBS buffer. After incubating the mixture on a rotating wheel for 1 h at ambient temperature, the unbound material was removed and the beads washed 2 times with wash buffer and once with PBS buffer then resuspended in 200 µl of PBS buffer. Neuraminidase (0.00175 U, EC3.2.1.18; Sigma) was added to each tube and the mixture incubated overnight at 37 degrees C. on a rotating wheel. The bound PS is heterogeneous with respect to Dp, therefore, the bead-antibody-PS complex was treated with neuraminidase, which sequentially removes residues from the non-reducing end of the polymer, to reduce the size of the polymer to the length that can be protected from further digestion by the antibody. After the neuraminidase treatment, the beads were washed 3 times with 50 mM ammonium carbonate buffer, pH 8.5 and the bound PS was finally eluted with 0.1 M triethylamine in water.

For analysis by matrix assisted laser desorption ionization time of flight (MALDI-TOF) mass spectroscopy, the solution of eluted PS and triethylamine/water was removed by evaporation in a Spin-Vac (Savant). Dried sample was resuspended in 4 µl of 50% (vol/vol) acetonitrile/water. The matrix, a saturated solution of 2',4',6'-trihydroxyacetophenone (THAP, Fluka Chemical) in 50% acetonitrile/water (0.5 µl), was spotted on a stainless steel target plate. PS sample (2 times, 0.5 µl) was spotted on top of the dried THAP spot. The samples were analyzed using a Bruker Autoflex MALDI-TOF mass spectrometer operating in the negative ion reflector mode.

Figure 4:
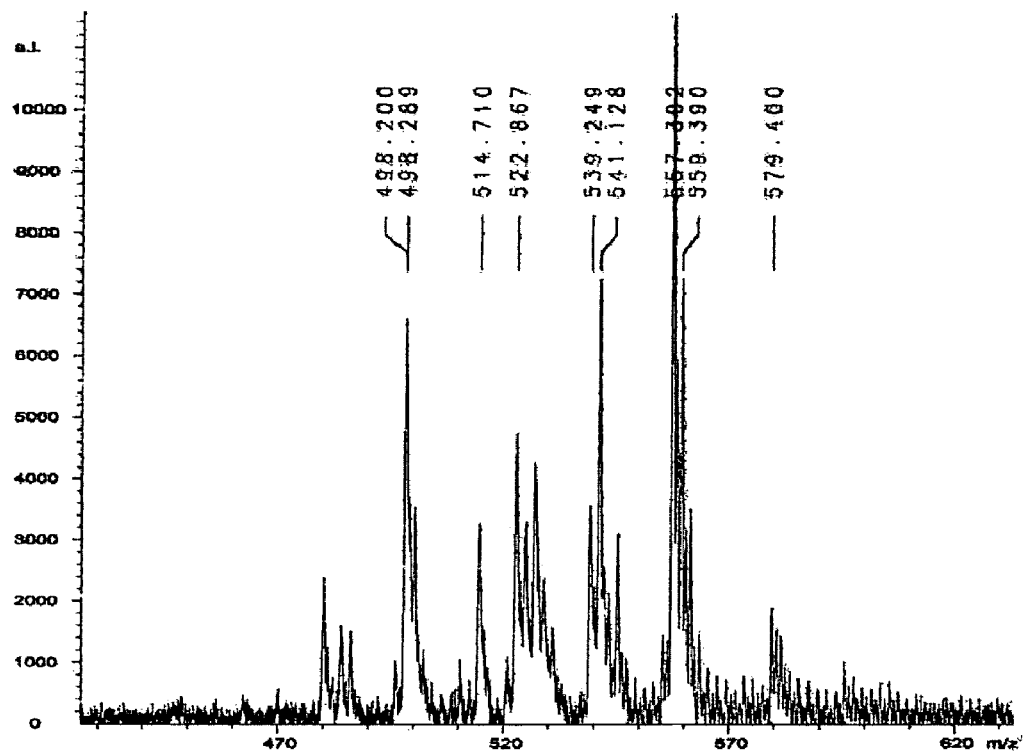
FIG. 4 shows the mass spectrum of PS derivatives selected and protected from neuraminidase cleavage by SEAM 3.
Figure 14:
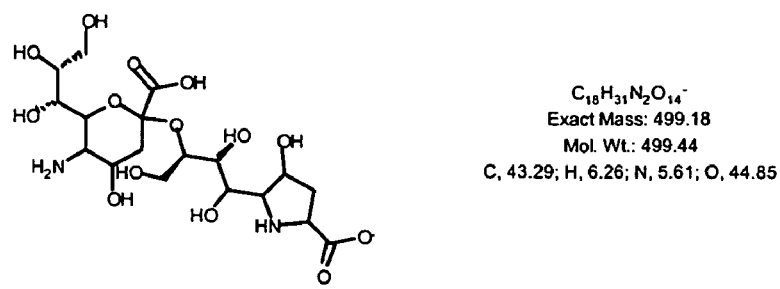
Figure 15:
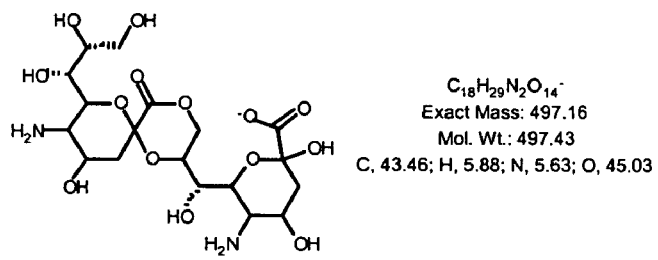

FIG. 4 shows a representative mass spectrum of PS derivatives bound by SEAM 3 after neuraminidase treatment. FIG. 5 shows the observed masses for each sample and the theoretical masses of corresponding ions that are consistent with the observed masses. The structures of PS derivatives are shown in FIGS. 6 to 15. All of the masses correspond to a disaccharide containing one or more residues in which the N-acetyl group on the C-5 amino group has been removed.

Example 3

Analysis of deNAs SA Epitope-Containing N—Pr NmB PS Derivatives that Bind to SEAM 3 by Sialidase a Digestion and High Performance Anion Exchange Chromatography with Pulsed Ampermetric Detection (HPAC-PAD)

The exo sialidase from *Arthrobacter ureafaciens* (SIALIDASE A™, Prozyme, Hayward, Calif.) cannot degrade polysialic acids (N—Ac or N—Pr derivatives) that terminate on the non-reducing end with a de-N—Ac sialic acid residue. Therefore, exhaustive digestion of a preparation of NmB PS or N—Pr NmB PS that contains de-N-acetyl residues randomly located throughout the polymer with sialidase A will result in conversion of the polysialic acid to 5-N-acyl neuraminic acid except when the sialidase encounters a de-N-acetyl residue. At that point, no further degradation of the polymer will occur. Also, the sialic acid molecules that are not degraded have a de-N-acetyl sialic acid residue at the non-reducing end. To confirm the results presented in Example 2 that SEAM 3 binds to a mixture of de-N-acetyl and N-acyl residues, preparations of colominic acid (EY Laboratories) and N—Pr NmB PS (10 mg each) were suspended in 50 mM NaOAc buffer, pH 6.5. SIALIDASE A™ (0.1 U, Prozyme) was added and the solutions were incubated at 37° C. for 3 days.

The fraction of N—Ac NmB oligosaccharide (OS) and polysaccharide (PS) and N—Pr NmB OS and PS remaining after sialidase treatment and the degree of polymerization were quantified by HPAC-PAD. The sample was injected into a Dionex (Sunnyvale, Calif.) liquid chromatograph fitted with a GP40 Gradient Pump, PA200 column equilibrated with 0.1 M NaOH (93%) and 0.1 M NaOH containing 1M NaOAc (7%) and an ED40 Electrochemical Detector. Saccharides were eluted with a linear gradient beginning from the initial conditions to 100% 0.1 M NaOH/1M NaOAc. Saccharides eluting from the column were detected by pulsed ampermetric detection using the ED40 Electrochemical Detector.

The resulting chromatogram showed that from about 81% to 88% of both PSs had been degraded to N—Ac or N—Pr neuraminic acid, respectively, with the remaining about 12-19% composed mainly of oligosaccharide having a Dp of from about 2 to about 18 (FIG. 36) and very small amounts of higher molecular weight polymers. The HPAC-PAD analysis shows that both colominic acid and N—Pr NmB PS preparations contain de-N-acetyl residues even though the colominic acid preparation had not be subjected to de-N-acetylation/reacylation procedures.

The ability of colominic acid and N—Pr NmB PS to inhibit binding of SEAM 3 to in an ELISA was compared to sialidase A-treated colominic acid and N—Pr NmB PS prepared as described above. The wells of microtiter plates (Immulon 2; Dynatech Laboratories, Inc.) were coated with N—Pr NmB PS-dodecylamine (prepared as described in Example 1) in phosphate buffered saline (PBS; pH 7.4). The plates were incubated overnight at 4° C. After washing three times with PBS, the wells were filled with 200 µl of blocking buffer (PBS containing 1% bovine serum albumin [BSA, Sigma] and 0.1% sodium azide; [pH 7.4]) and then incubated for 30-60 min at room temperature to block nonspecific binding sites. The plates were washed three times with PBS buffer. Inhibitors were serially diluted in blocking buffer on the plate in total final volume of 50 µl SEAM 3 diluted in blocking buffer to a concentration that produced an OD405 nm of 0.5 when developed with substrate was added to the wells in a volume of 50 µl. The plates were covered and incubated overnight at 4° C. On the following day the wells were washed four times with PBS buffer and were incubated for 2 h at ambient temperature with 100 µl/well of alkaline phosphatase-conjugated anti-mouse polyclonal antibody (IgA+IgG+IgM; Zymed) diluted 1:3000 in blocking buffer. The plates were then washed with PBS buffer, and 100 µl of freshly prepared substrate (p-Nitrophenyl phosphate; Sigma) diluted to 1 mg/ml in substrate buffer in 50 mM sodium carbonate buffer, pH 9, containing 1 mM $MgCl_2$. The absorbance at 405 nm after 30 minutes incubation at ambient temperature was measured using a BioRad Model 550 microtiter plate reader. The relative activity of each sample was compared by determining the dilution required to decrease the absorbance at 405 nm by 50% of the absorbance observed in wells containing SEAM 3 but no inhibitor.

When measured by inhibition ELISA, the colominic acid preparation had approximately 200-fold less activity for binding to SEAM 3 than N—Pr NmB PS. However, there was no significant difference in the activity of the exosialidase-treated colominic acid or N—Pr NmB PS compared to the untreated preparations even though more than 80% of the PS had been converted to monomeric N-acyl neuraminic acid as determined by HPAC-PAD. The results clearly shows that the epitope recognized by SEAM 3 is composed of a mixture of de-N-acetyl and N-acyl residues but not NmB PS derivatives that do not contain de-N-acetyl residues. Since the Dp characterized by HPAC-PAD varies between 2 and about 27, the de-N-acetyl residues can occur internally within the polymer or at the non-reducing end.

The amount of antigen recognized by SEAM 3 in preparations of colominic acid or N—Pr NmB PS is not affected by exhaustive digestion with exosialidase while non-reactive molecules in the preparations that do not contain de-N-acetyl residues are degraded. Therefore, exhaustive exosialidase treatment of provides a means to greatly enrich colominic acid and N—Pr NmB PS preparations for molecules that bind to the mAb.

Example 4

Preparation of Vaccine Containing PS Derivatives Enriched with Respect to deNAc SA Antigens The following provides an example of a method for producing a deNAc SA antigen-containing vaccine from PS using both the sialidase-based enrichment method and generation of a conjugate by reaction with and linkage through an acryl- or haloacetyl- group.

De-N-acetylation. Colominic acid (100 mg, EY Laboratories) and 10 mg of sodium borohydride (Sigma-Aldrich) are dissolved in 10 ml of 2M NaOH, placed in a sealed glass hydrolysis tube (Pierce) and heated to 90° C. for 2 h. The solution is allowed to cool to ambient temperature and glacial acetic acid is added to lower the pH of the solution to approximately 7. The solution is dialyzed (1 kDa cutoff) in 2×4 L of water and lyophilized.

Re-N-acylation. The de-N-acetylated NmB PS is resuspended in 5 ml of water and the pH adjusted to 8-9 with 2M NaOH. Acyl anhydride (e.g. acetic anhydride or propionic anhydride) is added in 5 portions of 0.1 ml over a period of several hours with stirring. The pH is monitored with a pH meter and is adjusted to 8-9 with 2M NaOH as needed. The solution is dialyzed in water as before and lyophilized. The re-acylated NmB PS typically contains 10%-30% de-N-acetyl sialic acid as determined by resorcinol assay (vide supra). The product is enriched with respect to antigens that are reactive with SEAM3 by treatment with SIALIDASE A™ (Prozyme).

Sialidase treatment. The lyophilized powder is resuspended in 1 ml of 50 mM sodium acetate buffer, pH 6.5. (1U) is added add the solution is incubated at 37° C. for 3-7 days. The progress of the reaction is monitored by periodic HPAC-PAD analysis of a small portion of the reaction mixture that if first filtered through a Centricon membrane (30 kDa cutoff, Millipore) to remove the. When no further release of 5-N-acyl neuraminic acid occurs, the reaction is terminated and cyclic lactones are hydrolyzed by increasing the pH of the reaction to 12 with 2M NaOH for 1 h, neutralizing with glacial acetic acid, filtering through a 30 kDa Centricon membrane, dialyzing in water (1 kDa dialysis tubing), and lyophilizing the product.

N-acylation with acrylic acid (or haloacetic acid). The sialidase-treated partially de-N-acetylated NmB PS is resuspended in water and the pH is adjusted to 8-9 with 2M NaOH. An amount of acrylic acid (or haloacetic acid) equal to from 10% to 100% of the amount of de-N-acetyl sialic acid present in the preparation of re-N-acylated NmB PS (typically 40%-50% of the total amount of sialic acid determined by resorcinol assay) is combined with 0.9 equivalent of EDC (Pierce). A small amount of water is added as necessary to dissolve the EDC. The solution of activated acrylic acid (or activated haloacetic acid) is added to the preparation of partially re-N-acylated NmB PS with stirring and the pH is maintained to 8-9 by adding 2M NaOH as necessary. Although an amount of activated acrylic acid (or activated haloacetic acid) equal to the amount of de-N-acetyl sialic acid can be added to the reaction, some amount of de-N-acetyl sialic acid will remain since some of the activated acrylic acid will hydrolyze. After stirring for 1 h, the reaction mixture is dialyzed and lyophilized as described above. The product is stored sealed under argon in the dark at −80° C. until used for conjugation to a carrier protein.

Conjugation to a carrier protein. The carrier protein (10 mg) is dissolved in 50 mM HEPES, pH 8.0, containing 150 mM NaCl. The acyl-containing NmB PS preparation is added (20 mg) and the solution left standing at ambient temperature in the dark for 2 days. The solution is then dialyzed in PBS buffer using a dialysis membrane having a mass cutoff of 30 kDa. The dialyzed conjugate is finally sterile filtered (0.2µ) and stored at 4° C. until used. The amount of sialic acid conjugated to the protein is determined by resorcinol assay and conformation that the PS is covalently linked to the protein is determined by SDS-PAGE and Western blot detection with SEAM3.

Example 5

Biosynthetic Incorporation of N-Trichloroacetyl (or Trifluoroacetyl) Protected Sialic Acid Residues into Bacterial PS and Use of the Resulting Capsular PS to Prepare PS-Protein Conjugate Vaccines 0.5 millimole (108 milligrams) of mannosamine hydrochloride was dissolved in 10 milliliter of methanol containing 0.55 millimole of sodium methoxide and cooled to 4 degrees C. 0.6 millimole of trichloroacetic anhydride (or ethyl trifluoroacetate) was added and the mixture stirred for 2 hrs. The progress of the reaction was monitored by spotting the reaction mixture on a silica gel TLC plate, developing the plate with ethylacetate, methanol, water (5:2:1) and detecting the disappearance of mannosamine at the origin with iodine vapor or nihydrin reagent with heating. At the completion of the reaction, 1.5 milliequivalents of AG 501-8X mixed bed resin (BioRad) and 10 milliliters of water was added, the pH was adjusted to 7 by adding NaOH or HCl as needed and the mixture gently shaking for 1 hour. The solvent mixture and beads were separated and the solvent was removed by lyophilization. Further purification of the product, if necessary, was performed by silica gel chromatography using the same solvent system described for TLC. Solvent from the combined fractions containing the desired material was removed by evaporation. Finally, the dried product was resuspended in water and lyophilized.

The trihaloacetylated mannosamine was incorporated into NmB PS by inoculating colonies of NmB strain M7 grown overnight at 37 degrees C. in 5% carbon dioxide on a freshly streaked chocolate agar plate to an OD620 nm of 0.1 in Muller-Hinton broth supplemented with 5 millimolar N-acyl mannosamine For example, N-acetyl, -trichloroacetyl, -trifluoroacetyl mannosamine. Stain M7 contains a transposon the interrupts the gene encoding N-acetyl-D-glucosamine-6-phosphate 2 epimerase (Swartley et al. 1994, J. Bact. 176: 1530; Swartley et al. 1996, J. Bact. 178:4052). As a result, the bacteria cannot synthesize capsule PS unless the growth media was supplemented with N-acetyl mannosamine. Therefore, the N-acyl content of the capsule PS synthesized in this system can be determined by the N-acyl or mixture of N-acyl mannosamine provided in the growth media. The bacteria were grown at 37 degrees C. to an OD620 nm of overnight).

Mutants of *E. coli* K1 can also be used in this production method in lieu of an NmB strain. Suitable *E. coli* K1 mutants that are deficient in capsular PS can be generated by, for example, knocking out expression of a functional neuC gene product. Since, neuC encodes an N-acetyl-D-glucosamine-6-phosphate 2 epimerase , *E. coli* strains deficient in this gene can not synthesize capsular PS, and thus are suitable for use in this method of PS derivative production.

The production of capsule PS containing the trihalo acetyl groups was demonstrated by fluorescence microscopy using the mAb SEAM 12 (Granoff et al. (1998) J Immunol 160, 5028-36) to detect the presence of capsule PS on the M7 producing strain. The results are shown in FIG. 37. Binding of SEAM 12 to M7 supplemented with N-acetyl mannosamine is shown in FIG. 37 (panel A) where binding is indicated by the presence of red fluorescence (shaded gray in the figure) of the detecting, rhodamine-labeled secondary antibody (Zymed). There is no binding of SEAM 12 to M7 without N-acyl mannosamine or with N-trichloroacetyl mannosamine supplement (FIG. 37, panels B and C). SEAM 12 does not bind to the capsule PS containing the trichloroacetyl groups because the large size of the trichloromethyl group disrupts binding. However, SEAM 12 does bind to the capsule PS containing N-trifluoroacetyl groups (FIG. 37, panel D, shaded gray in the figure) since the trifluoromethyl group is nearly the same size as the methyl group of the N-acetyl derivative.

The polysaccharide was purified from the growth media as described by Guo and Jennings (Guo, Z. and Jennings, H. in 2001. In Meningococcal Vaccines: Methods and Protocols. A. J. Pollard, and C. J. M. Maiden, eds. Humana Press Inc., Totowa, N.J., p. 41). The purified polysaccharide was oxidized, conjugated to carrier proteins or fatty amines by reductive amination as described above, and the trihaloacetyl groups were removed by reduction with sodium borohydride. The final product was purified by size exclusion chromatography as described above, dialyzed in PBS, and lyophilized.

Example 6

Biosynthetic Incorporation of N-Trichloroacetyl (or Trifluoroacetyl) Protected Sialic Acid Residued into Gangliosides and Use of the Resulting Gangliosides to Prepare Protein Conjugate Vaccines and Outermembrane Vessicle Vaccines 1 g of mannosamine hydrochloride (4.5 mmol) was dissolved in 50 ml of methanol containing an equivalent of sodium methoxide and cooled to 4° C. 5.1 millimole of trichloroacetic chloride (or ethyl trifluoroacetate) was added and the mixture stirred for 2 hrs. Additional sodium methoxide was added as needed to maintain the pH at ~8. The progress of the reaction was monitored by spotting the reaction mixture on a silica gel TLC plate, developing the plate with ethylacetate, methanol, water (5:2:1) and detecting the disappearance of mannosamine at the origin with iodine vapor. At the completion of the reaction, the solvent was removed by evaporation. After triturating the remaining solid with 5 ml of methanol, the N-trihaloacetyl derivative was crystallized from methanol/chloroform.

SK-Mel-28 cells were grown on square 245 mm×245 mm bioassay dish (Corning) until near confluent. Growth medium (RPMI supplemented with 5 mM glutamine, 1 mM sodium pyruvate, 0.1 mM non-essential amino acids, 10% fetal bovine serum, and antibiotics) was replaced with growth medium containing trichloroacetyl mannosamine (5 mM) for 24 hours, after which cells were washed three times with PBS and lysed by hypotonic shock in distilled water (lhour at 4° C.). This was followed by 3 cycles of freeze/thawing using ethanol on dry ice/37° C. water bath. The crude membrane fraction was pelleted by centrifugation at 4500 g for 20 minutes at 4° C. The pellet was lyophilized and the lipids extracted by stepwise washing with methanol/chloroform (1:2, 1:1, 2:1 by volume) for 30 minutes (Geilen et al 1992, Arch. Biochem. Biophys. 296, 108-114). The organic phase was dried under a steady stream of oxygen-free nitrogen gas and resuspended in 200 µl of chloroform/methanol/0.02% $CaCl_2$ (50:40:10).

De-N-acyl GM3 and GD3 (Calbiochem) were prepared by suspending 1 mg of ganglioside in 2 ml of 2.5 M tetrabutylammonium hydroxide and 3 ml of butanol then heating the mixture to >100 degrees C. for 4 hours. After cooling the mixture to ambient temperature, the pH was adjusted to about 7 by adding 2 M HCl and the butanol removed by evaporation under a stream of $N_2$. The remaining aqueous layer was dialyzed (1K cut-off dialysis tubing) against PBS buffer and used without further modification as an antigen for ELISA.

Lipids in the extract and in chemically de-N-acylated GD3 were analyzed by separation on high performance thin, layer chromatography (HPTLC) and Western blot. Samples of the ganglioside extract, the ganglioside extract that had been treated with sodium borohydride (1 mg/100 µl at ambient temperature for 2 h) to remove the trichloroacetyl protecting group, and chemically de-N-acylated GD3 were spotted onto an aluminum-backed silica gel 60 HPTLC plate (Merck) and the plate developed in chloroform/methanol/0.02% $CaCl_2$ (50:40:10). Plates used for Western blot were dried and dipped in a solution of 0.4% polyisobutylmethacrylate in hexame/chloroform (21:8) for 1 min. The plates were blocked with 1% bovine serum albumin (BSA) in PBS buffer containing 0.1% sodium azide. MAbs (5 µg/ml) in the same blocking buffer were incubated with the plates at 4° C. overnight. The plates were washed 3 times in PBS buffer then incubated with goat anti-mouse Ig-HRP conjugate (Zymed) in PBS containing 1% BSA. After washing the plates 3 times with PBS, substrate (HRP Chemiluminescence Reagent Plus from Perkin-Elmer) was added to develop the plates. The luminescent image was captured on film.

Figure 38:
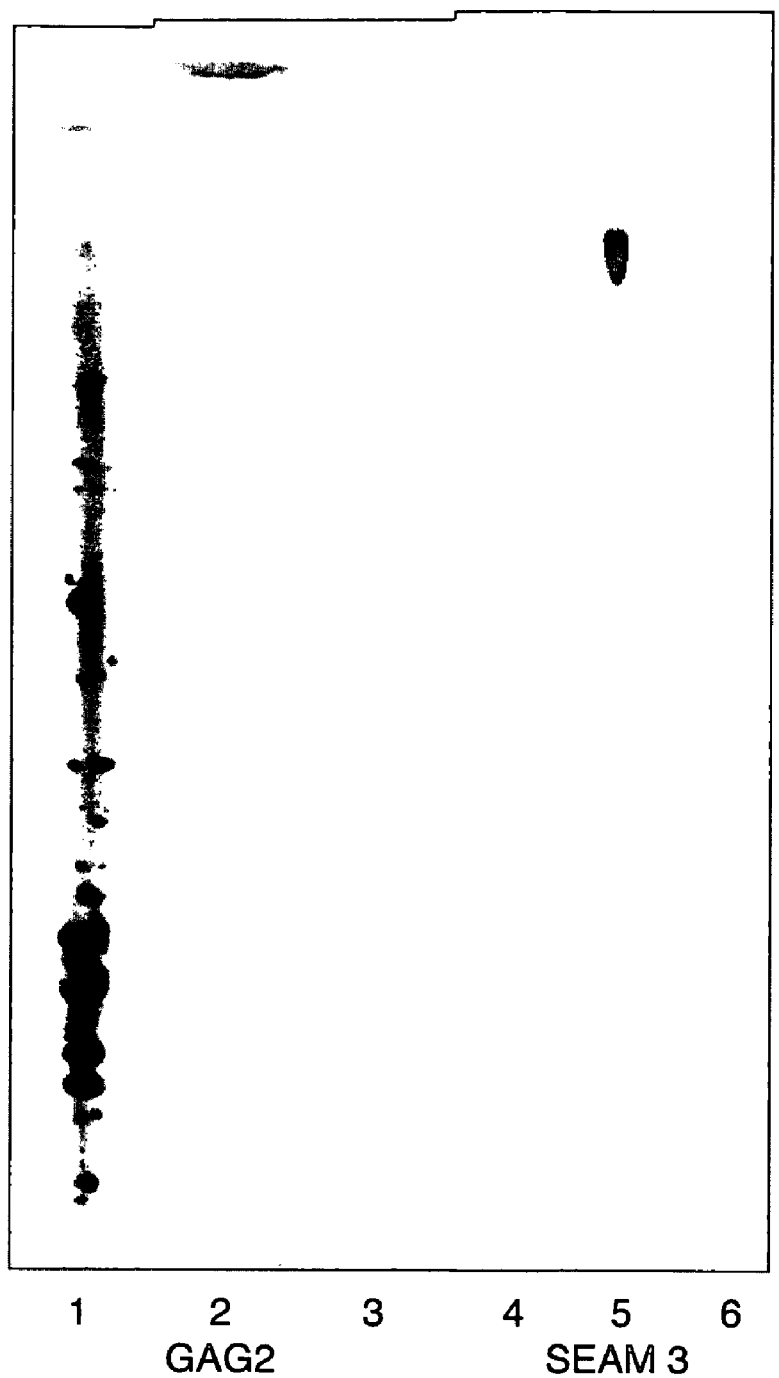
FIG. 38 is a photograph showing the reactivity of an anti-de-N-acyl GD3 mAb, GAG2, and SEAM 3 with de-N-acetyl sialic acid gangliosides prepared chemically or biosynthetically. The ganglioside derivatives were separated by high performance thin layer chromatograpy and detected by Western blot with either GAG2 (Lanes 1-3) or SEAM 3 (Lanes 4-6).

Western blot to evaluate the reactivity of an anti-de-N-acyl GD3 mAb with de-N-acetyl sialic acid gangliosides prepared chemically or biosynthetically was performed with either GAG2 (Lanes 1-3, FIG. 38) or SEAM 3 (Lanes 4-6, FIG. 38). GAG2 is a murine monoclonal antibody (IgM) prepared to de-N-acyl GD3 by immunizing mice with *N. meningitidis* outer membrane vesicles (strain H44/76 in which the siaD gene has been inactivated) containing de-N-acyl GD3 (EXAMPLE 9). The vesicles were prepared as described below. GAG2 binds to de-N-acyl GD3 but not to re-N-acetylated GD3. Lanes 1 and 3 are gangliosides obtained from treatment of GD3 with tetrabutyl ammonium hydroxide (i.e. chemical de-N-acylation). Lanes 2, 3, 5 and 6 are gangliosides extracted from SK-MEL-28 cells grown in media supplemented with N-trichloroacetyl mannosamine (i.e. biosynthetic N-protected sialic acid containing gangliosides). The lipid extract in lanes 2 and 5 was treated with $NaBH_4$ to remove the trichloroacetyl protecting group to produce the de-N-acetyl sialic acid gangliosides. Lanes 3 and 6 contain the same lipid extract that has not been treated with $NaBH_4$. SEAM 3 does not react with any of the de-N-acyl gangliosides produced by alkali treatment. GAG2 reacts with a de-N-acetyl sialic acid ganglioside produced biosynthetically that moves with the solvent front (lane 2) while SEAM 3 reacts with a different slower moving de-N-acetyl ganglioside derivative (lane 5). The lack of reactivity with both mAbs with lipid extract run in lanes 3 and 6 shows that the N-trichloroacetyl protecting group remains intact during the isolation procedure and that de-N-acetyl sialic acid ganglioside derivatives are produced after removal of the protecting group with $NaBH_4$.

The results in FIG. 38 demonstrate that SEAM 3 binds to de-N-acetyl sialic acid gangliosides prepared by biosynthesis of N-trichloroacetyl-protected gangliosides in SK-MEL-28 cells followed by removal of the protecting group with $NaBH_4$ (lane 5) but not to the protected derivative (lane 6) or to chemically de-N-acylated GD3 (lane 6). In addition, a mAb that is specific for de-N-acylated GD3 prepared by alkali treatment (GAG2) reacts with a different, faster moving derivative in the $NaBH_4$-treated SK-MEL-28 lipid extract. Thus, the methods described here can be used to selectively prepare ganglioside derivatives for use as vaccine and diagnostic antigens that are reactive with mAbs, such as SEAM 3, that recognize de-N-acetyl sialic acid residues and have cytotoxic functional activity against cancer cells that express de-N-acetyl sialic acid antigens.

Example 7

Preparation of deNAc SA Antigens—Ganglioside Derivatives Having a Mixture of N-Acetyl and de-N-Acetyl Sialic Acid Residues N-trichloroacetyl/N-acetyl sialic acid ganglioside derivatives obtained by biosynthesis in SK-MEL-28 cells were solubilized in chloroform/methanol/0.02% $CaCl_2$. The N-trichloroacetyl amine protecting group was removed by reduction with sodium borohydride (1 mg $NaBH_4$/10 mg of crude lipid extract). Calcium borate that precipitated from the reaction was removed by centrifugation. The lipid derivatives were separated by HPTLC. The band containing material reactive with SEAM 3 was scraped from the plate and extracted with chloroform/methanol (1:1). After removing the silica gel by centrifugation, the solvent from the extracted band was dried under $N_2$.

Outer membrane vesicles were prepared from *Neisseria meningitidis* group B strain H44/76 in which the sialyl transferase gene siaD has been inactivated: Cells from 1 liter of H44/76 grown in Muller-Hinton broth to an A620 nm of 0.6 were pelleted by centrifugation at 10,000×g for 30 min. The cell pellet was resuspended in 0.1M Tris-HCl, pH8.6, containing 10 mM EDTA and 0.5% DOC with the ratio of buffer to biomass of 5:1 (v/w). The supernatant was collected after centrifugation (20,000×g; 30 minutes; 4° C.) and the extraction was repeated with buffer volume reduced to one third. The combined supernatants were ultracentrifuged (125,000× g; 2 hrs; 4° C.), and the OMV pellet resuspended in 50 mM Tris-HCl buffer, pH 8.6, containing 2 mM EDTA, 1.2% DOC and 20% sucrose. The protein concentration was determined using a standard protein assay (BCA, BioRad). The vesicle preparation and Empigen (1% w/v; Calbiochem) was added to the lipid film and sonicated with a bath sonicator (Branson) for 30 min then left to stir overnight at 4° C. The mixture was then dialyzed exhaustively in PBS buffer for 5 days. The resulting OMV/ganglioside complexes were sterile filtered and frozen until used for vaccination.

Example 8

Preparation of N-Trihaloacetyl/N-Acetyl Sialic Acid Ganglioside-Protien Conjugate Vaccine The crude lipid fraction from the biosynthesis of N-trihaloacetyl/N-acetyl sialic acid gangliosides in SK-MEL-28 cells was purified by HPTLC, and the N-trihaloacetyl/N-acetyl sialic acid ganglioside derivatives were extracted from the plate as described in Example 7. After removing the silica gel by centrifugation, an aldehyde group was generated in the ganglioside by ozonolysis of the sphingosine double bond. The aldehyde was purified by reverse phase HPLC (Waters'Bondpak C18 microbore) and coupled to tetanus toxoid by reductive amination with sodium cyanoborhydride. An excess of sodium borohydride was added to the same reaction mixture to remove the N-trihaloacetyl protecting group. The reaction mixture was dialyzed in PBS buffer, sterile filtered, and frozen until used for immunization.

Example 9

Purification of SEAM 3 mAb

Solid sodium sulfate (Sigma-Aldrich Chemical Co., Saint Louis, Mo.) was added to a solution of SEAM 3 in PBS buffer (concentration of antibody approximately 30 micrograms/ml as determined by antibody capture assay (SouthemBiotech, Birmingham, Ala.)) to a final concentration of 0.5 M. After completely dissolving the solid sodium sulfate, the solution was incubated approximately 18 hrs at 4° C. The solution was centrifuged (10,000×g) to remove precipitates and filtered (0.2µ). The antibody was then purified by size exclusion chromatography on a Toyopearl HW55F column (Supelco, Bellefonte, Pa.; 1.5 mm×25 mm) equilibrated with PBS buffer containing 0.5 M sodium sulfate. Fractions containing active antibody were determined by ELISA using N-propionyl NmB PS-dodecylamine (vide supra) as a solid phase antigen and detection using alkaline phosphate conjugated to rabbit anti-mouse IgA,G,M (H and L) (Zymed, South San Francisco, Calif.) and developed 4-nitrophenyl phosphate substrate (Sigma-Aldrich). Fractions containing active antibody were combined and dialyzed against PBS, sterile filtered (0.2µ) and stored at 4° C. Antibody concentrations of purified antibodies were determined by antibody capture assay (Southern Biotech).

Purified SEAM 3 was used in the Examples below.

Example 10

Presence of SEAM 3 Reactive Antigen in Cancer Cells and Absence in Normal Cells To determine whether there is a difference in expression of SEAM 3-reactive antigen between normal melanocytes and melanoma tumor cells, immuno-staining of thin sections of each type of tissue were performed. In addition to SEAM 3, controls included the secondary antibody alone and R24, which binds to the ganglioside GD3 that is expressed in normal melanocytes and is overexpressed in some melanomas (Dippold et al. Proc Natl Acad Sci USA, 1980. 77(10): 6114-8.; Graus, et al., Brain Res, 1984. 324(1): 190-4; Houghton et al. Proc Natl Acad Sci USA, 1985. 82(4):1242-6; Panneerselvam et al. J Immunol, 1986. 136(7): 2534-41; Real et al. Cancer Res, 1985. 45(9): 4401-11; Vadhan-Raj et al. J Clin Oncol, 1988. 6(10): 1636-48; Welt t al. Clin Immunol Immunopathol, 1987. 45(2): 214-29).

The tissue sections were made from frozen samples of normal skin (HuSkinTb111 in FIG. 39) and two human melanomas (HuMel1151 and HuMel4034). To prevent the possibility of blocking de-N-acetyl antigen or extracting a lipid containing the antigen, the sections were prepared from frozen tissue and were dried onto the slides but not fixed with aldehydes or organic solvents (Chammas et al: Cancer Res, 1999. 59(6): 1337-46). Endogenous peroxidases were removed by incubation in 0.03% peroxide for 30 min., followed by buffer washes and then endogenous biotin was blocked using the Avidin/Biotin blocking kit from Vector Labs (Burlingame, Calif.). Non-specific binding to collagen was blocked with 1% BSA/PBS. BSA, or the mAbs R24 or SEAM 3 were then incubated in a humid chamber. Unbound antibody was removed by buffer rinses. Bound antibody was then detected using the DAKO LSAB kit following the manufacturer's directions (Thermo Fisher Scientific, Waltham, Mass.). After additional washes, nuclei were counterstained using Mayer's hematoxylin (Vector Labs).

Figure 39:
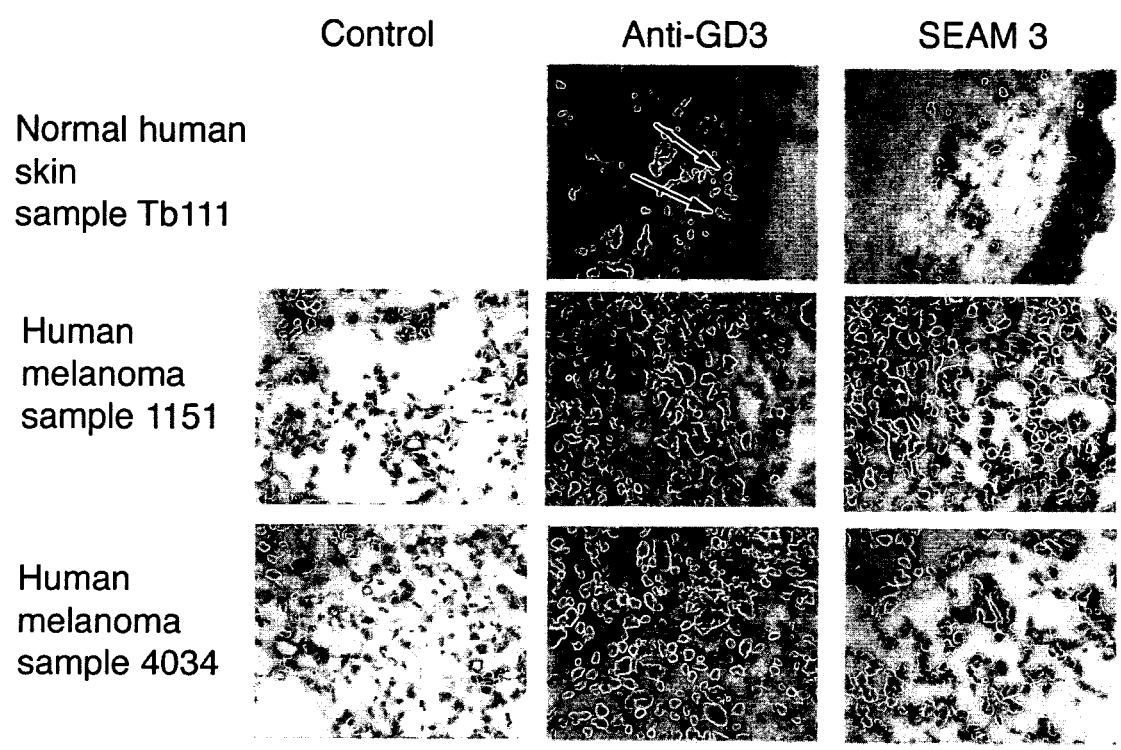
FIG. 39 is a series of photographs of human normal and melanoma cancer tissues depicting the immunohistochemical analysis of SEAM 3 and anti-GD3 mAb, R24 binding.

The results at 400× magnification are shown in FIG. 39. Immunostaining of normal human skin shows that anti-GD3 mAb R24 identifies melanocytes (arrows) as well as some neural twigs in the dermis of the skin. SEAM 3 binds to an antigen in neural like structures of the dermis but is not present in melanocytes. Staining of the two melanomas shows that R24 reacts strongly with some but not all cells. In contrast, SEAM 3 staining is weaker but nearly all of the melanoma cells are stained, as indicated by darkly shaded areas. The SEAM 3 staining appears to be granular and intracellular in the melanomas cells. Thus, the antigen recognized by SEAM 3 is not detectably present in normal melanocytes but is present in human melanoma tumors. Based on fluorescence microscopy and cytotoxicity against SK-MEL-28 melanoma, CHP-134 neuroblastoma, and Jurkat cells (acute lymphoblastic T-cell leukemia) described below (vide infra), the antigen is present on the cell surface during some stage of growth (data not shown). The cytotoxic effect of SEAM 3 was observed on each cell type (SK-MEL-28 melanoma, CHP-134 neuroblastoma, and Jurkat cells) and was approximately proportional to the level of antigen present on the cell surface.

Example 11

SEAM 3 Binding to Formalin-Fixed Paraffin Embedded Tissues Sections from Human Tumors Initial immunohistochemical analysis of antigens recognized by SEAM 3 was performed on unfixed tissues out of concern that the de-N-acetyl amino groups could be blocked by reaction with formaldehyde (vide supra). Subsequently, it was determined that the amino group in de-N-acetyl sialic acid is relatively unreactive as a result of its close proximity to the C1 carboxyl group. Therefore, large scale screening of human tumors for the presence of SEAM 3-reactive antigens was performed using formalin-fixed paraffin embedded tissue sections since processing the samples by this method considerably improves the preservation of cell structural features.

Human tissue microarrays were obtained from US BioMax (Rockville, Md.). The tissue microarrays were deparaffinized in xylene (2 changes, 10 minutes each) then rehydrated by sequential 5 minute washes in 100% ethanol, 95% ethanol, 70% ethanol, 50% ethanol, and PBS buffer. Endogenous peroxidase was blocked by incubation with Peroxidazed 1 solution (Biocare, Concord, Calif.) for 5 minutes at ambient temperature. The sections were blocked with Terminator (Biocare) containing streptavidin then rinsed with PBS buffer. The primary antibody (purified SEAM 3 (vide infra), irrelevant IgG2b control, etc. at concentrations of 1 to 5 µg/ml)) was diluted in Da Vinci Green dilution buffer (Biocare) and incubated either overnight at 4 degrees C. or for 1 hour at ambient temperature. The slides were washed 3 times for 10 minutes each with PBS buffer then incubated with biotin conjugated rabbit anti-mouse IgG secondary antibody (5 µg/ml, Vector Labs, Burlingame, Calif.) for 30 minutes at ambient temperature. After washing 3 times for 10 minutes each with PBS buffer, horse radish peroxidase-streptavidin conjugate (Vector Labs) was added and incubated at ambient temperature for 30 minutes. The slides were washed 3 times for 10 minutes each with PBS buffer and incubated with AEC substrate (Vector Labs) containing hydrogen peroxide for color development. Color development was allowed to proceed for 30 seconds to 30 minutes depending on the sample and was then stopped by washing with water, counter stained with Hematoxylin QS (Vector Labs), rinsed with water and finally mounted in VectraMount AQ aqueous mounting medium (Vector Labs) and viewed/photographed under a microscope (Zeiss Axioplan).

The results for 47 human tumors are summarized in FIG. 40. All tumors and normal tissues tested were negative for binding with the irrelevant isotype-matched control mAb (murine IgG2b, Southern Biotech). The intensity of staining and the number of cells stained was variable in the tumor samples ranging form no staining to (indicated by "−") to dark staining of all cells (indicated by "+++") with variations between the extremes. Most of the tumor samples tested were positive for SEAM 3 binding (38 of 47) and represent a broad range of tumor types. Typically, the staining resulting from SEAM 3 binding observed in the tumor tissues has a "granular" appearance and is coincident with cell structures. A micro array of normal tissues was also tested. Generally, the "normal" tissue samples were obtained from the same subjects as the tumors but were obtained from regions outside the margins of the primary tumors. All of the normal tissues (17 samples) were negative for binding with the control mAb. SEAM 3 was positive for binding to 15 of 17 samples ranging from + to ++. However, unlike the staining observed in tumor tissues, staining resulting from SEAM 3 binding in the normal tissues is not granular but is instead homogenous, is not coincident with cell structures except for a few cells, and is continuous with stromal tissues. At the present time the differences in the appearance of staining is not understood.

Example 12

SEAM 3 Binding to HUman Melanoma SK-Mel-28, and Neuroblastoma CHP-134 Cell Lines by Fluorescence Microscopy and Flow Cytometry SK-MEL-28 cells (Carey et al. Proc Natl Acad Sci USA, 1976. 73(9): 3278-82) cells were purchased from the American Type Culture Collection (ATCC). Cells were grown routinely in RPMI 1640 medium containing 0.1 mM non-essential amino acids, 1.0 mM sodium pyruvate, 0.1 mM glutamate, penicillin/streptomycin and 10% fetal bovine serum at 37° C. in 95% air:5% $CO_2$. Confluent cells were sub-cultured (1:3 to 1:8) by treating with 0.25% (w/v) Trypsin/0.53 mM EDTA solution, washed and triturated before re-seeded into new growth medium. SK-Mel 28 cells were only used up to passage 10 from the ATCC stock cells. These cells express the ganglioside GD3.

The human T cell leukemia cell line Jurkat (Schneider et al. Int J Cancer, 1977. 19(5):; Schneider et al. Haematol Blood Transfus, 1977. 20:) were grown in RPMI 1640 containing 10% FBS, 2 mM L-glutamine in 5% CO2 at 37° C. and subcultured every 3 days with a split ratio of about 1:5. Cells were collected by centrifugation (500 g) and resuspended in fresh medium before subculture. The cells are positive for expression of the following CD antigens: CD2, CD3, CD4, CD5, CD6, CD7, CD34, and are negative for expression of CD8, CD13, CD19, TCRalpha/beta, TCRgamma/delta.

CHP-134 neuroblastoma cells (Livingston et al. J Biol Chem, 1988. 263(19): 9443-8) were routinely grown in RPMI 1640 medium containing 0.1 mM non-essential amino acids, 1.0 mM sodium pyruvate, 0.1 mM glutamate, penicillin/streptomycin and 10% fetal bovine serum at 37° C. in 95% air:5% $CO_2$. Confluent cells were sub-cultured (1:3 to 1:5) by treating with Cell Dispersal Reagent (CDR, Guava Technologies, Haywood, Calif.), washed and triturated before re-seeded into new growth medium. These cells express the neural cell adhesion molecule (NCAM) which is modified with long chain polysialic acid (i.e. poly alpha 2-8N-acetyl neuraminic acid).

To observe binding of SEAM 3 to the surface of cells, adherent CHP-134 or SK-Mel-28 cells (approximately $10^5$ cells) were cultured on multi-well microscope slides that had been treated with ploy-L-lysine (Nunc). After an overnight incubation cells were gently washed with PBS buffer and fixed with ice-cold 1% (v/v) formaldehyde. After 20 minutes cells were washed with PBS before blocking non-specific binding with a solution of 3% goat serum for 1 hour. To observe the presence of SEAM 3-reactive antigen that is present inside the cells, the cells were treated Triton X-100 0.5% w/v in 3% goat serum for 1 hour. The primary antibodies were added and incubated for 2 hours or overnight at 4° C. Cells were gently washed by a series (at least twice) with ice-cold PBS before isotype-specific secondary antibody (produced in goat) conjugated with either Alexa Fluor 488 (immunofluorescence and confocal), Alexa Fluor 546 (confocal) Alexa Fluor 594 (immunofluorescence), Alexa Fluor 633 (confocal) was applied for at least 1 hour at 4° C. in the dark (all secondary antibodies conjugated to fluorophores were obtained from Invitrogen, Carlsbad, Calif.). After another series of gentle washes, a hardening mounting medium containing DAPI was applied.

Immunofluorescence was observed with a Zeiss Axioplan Fluorescence Microscope fitted with a digital camera. Confocal images were obtained using a Zeiss Meta510 CLSM at the Biological Imaging Facility, University of California, Berkeley, Calif. and were analyzed using ImageJ Software (NIH). Control antibodies and secondary antibodies applied alone were routinely used to assess background fluorescence. The positive control mAb that is specific for GD3, R24 was positive for binding to SK-MEL-28 melanoma cells but negative for binding to CHP-134 neuroblastoma (Livingston et al. J Biol Chem, 1988. 263(19): 9443-8) and Jurkat T-cell leukemia cells, which do not express GD3 (data not shown).

Figure 41:
FIG. 41 is a photograph showing fluorescence binding of SEAM 3 to SK-MEL 28 melanoma cells (dark shading).
Figure 42:
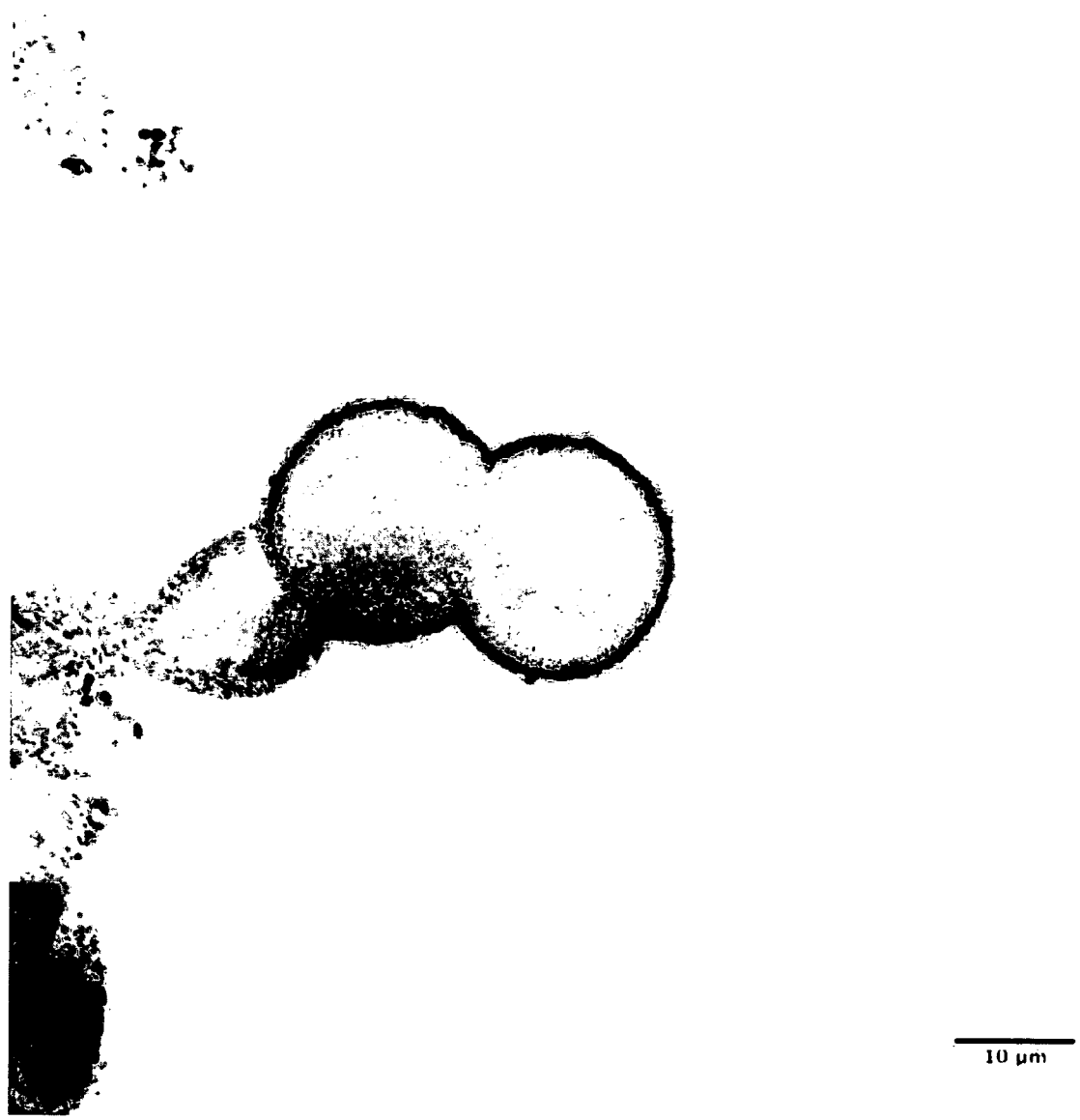
FIG. 42 is a photograph showing fluorescence binding of SEAM 3 to CHP-134 neuroblastoma cells (dark shading).
Figure 43:
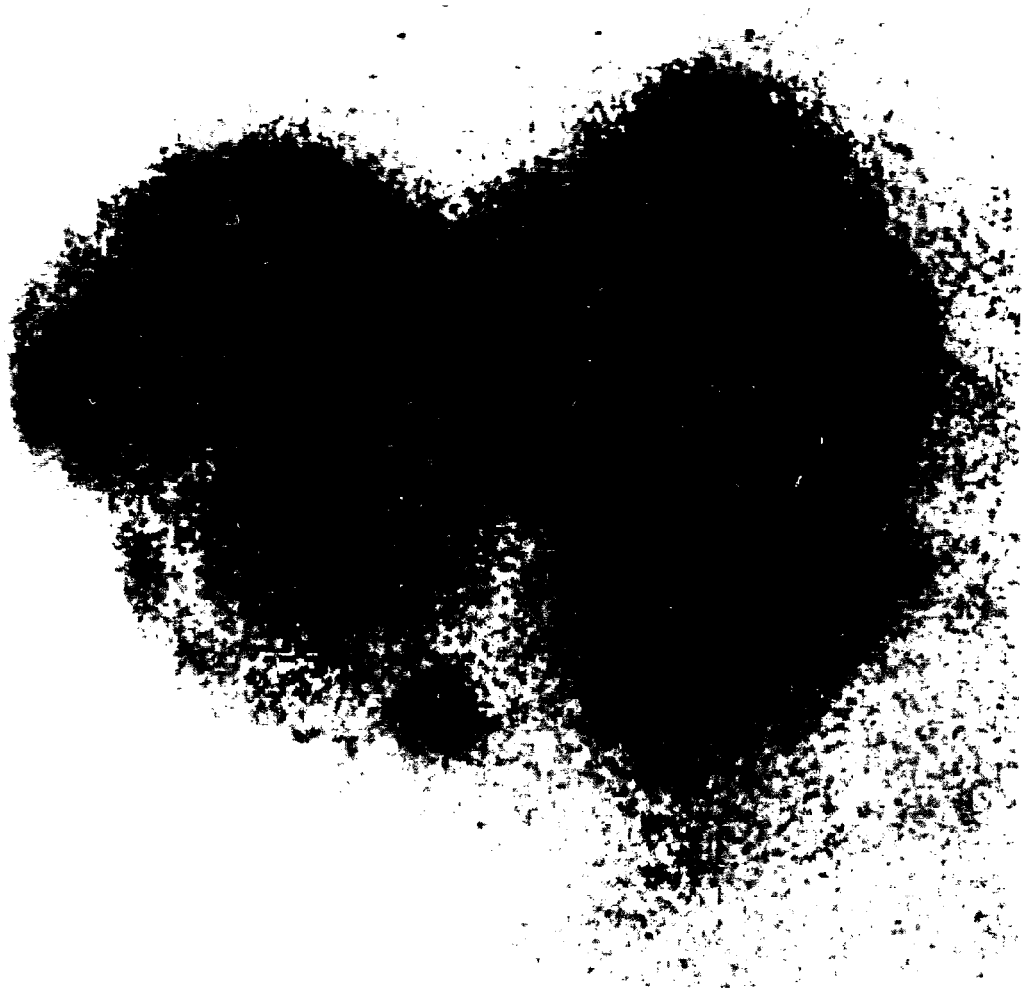
FIG. 43 is a photograph showing fluorescence binding of SEAM 3 to Jurkat T-cell leukemia cells (dark shading).

FIG. 41 and FIG. 42 show fluorescence on the cell surface (dark shading in the figure) resulting from SEAM 3 binding to SK-MEL-28 melanoma cells and CHP-134 cells as measured by confocal microscopy. FIG. 43 shows SEAM 3 binding to Jurkat cells as measured by fluorescence microscopy. In each case, the fluorescence is uniform over the cell surface. However, not all of the cells in the visual field show SEAM 3 binding. For adherent SK-MEL 28 and CHP-134 cells, cells that are positive for SEAM 3 binding differ morphologically from SEAM 3-negative cells. Positive cells are rounded up while negative cells are elongated. Using time-lapse photography of SK-MEL-28 cells in culture (at 37° C., 95%air:5% CO2), it was confirmed that the rounded up cells were not dead cells, but cells undergoing cell division. The cells remained in the spherical shape for approximately 3 hours, before they split into two daughter cells.

It should be noted that SK-Mel-28 cells overexpress GD3 ganglioside and are positive for binding by the anti-GD3 mAb R24. CHP-134 cells are GD3 negative, and are not bound by the R24 mAb. Moreover, since CHP-134 cells do not express GD3, they also do not produce any de-N-acetylated GD3 derivative. Since SEAM 3 binds to both SK-Mel-28 cells and CHIP-134 cells (and in fact exhibits greater binding to CHP-134 cells), these data indicate that SEAM 3 binds an antigen other than GD3 or GD3 derivative. In addition, SEAM 3 does not bind to an antigen derived from polysialic acid since it binds to SK-MEL-28 cells, which do not express N-CAM. Therefore, SEAM 3 binds to an antigen other than GD3 or N-CAM.

Example 13

SEAM 3 Binding to SK-MEL 28 Melanoma, Jurkat T-Cell Leukemia, and CHP-134 Neuroblastoma Cells Measured by Flow Cytometry Cells (approximately $10^5$ per well) were plated onto a flat bottom 96-well tissue culture plate (Nunc) and incubated with growth medium overnight before assay. Cells were detached from the plate by either trypsin (SK-MEL-28) or CDR (CHP-134) before being collected into a 96-round bottom plate, spun at 500 g for 5 minutes and fixed with ice-cold 1% (v/v) formaldehyde. After 20 minutes cells were pelleted by centrifugation (above) and incubated a blocking solution of 3% (v/v) goat serum with and without Triton X-100 (0.5% w/v) for 1 hour. After which the primary antibodies were added and incubated for 2 h or overnight at 4° C. The cells were washed twice by pelleting and resuspension in ice-cold PBS. Secondary antibody (Invitrogen, as described above) was incubated with the cells for at least 1 hour at 4° C. in the dark. After another series of spins and washes (3 times) binding was analyzed by a Guava EastCyte flow cytometer. Control samples were treated with an isotype matched irrelevant antibody (Southern Biotech), which were used to create baseline fluorescence, or positive control mAbs that are reactive with antigens specifically expressed by the cells (i.e. anti-GD3 for SK-MEL 28 cells and anti-NCAM in CHP-134 cells). In addition, specificity of binding was shown for the Jurkat cells by preincubating SEAM 3 with 50 µg/ml N—Pr NmB PS prior to adding the mAb to the cells.

Figure 44:
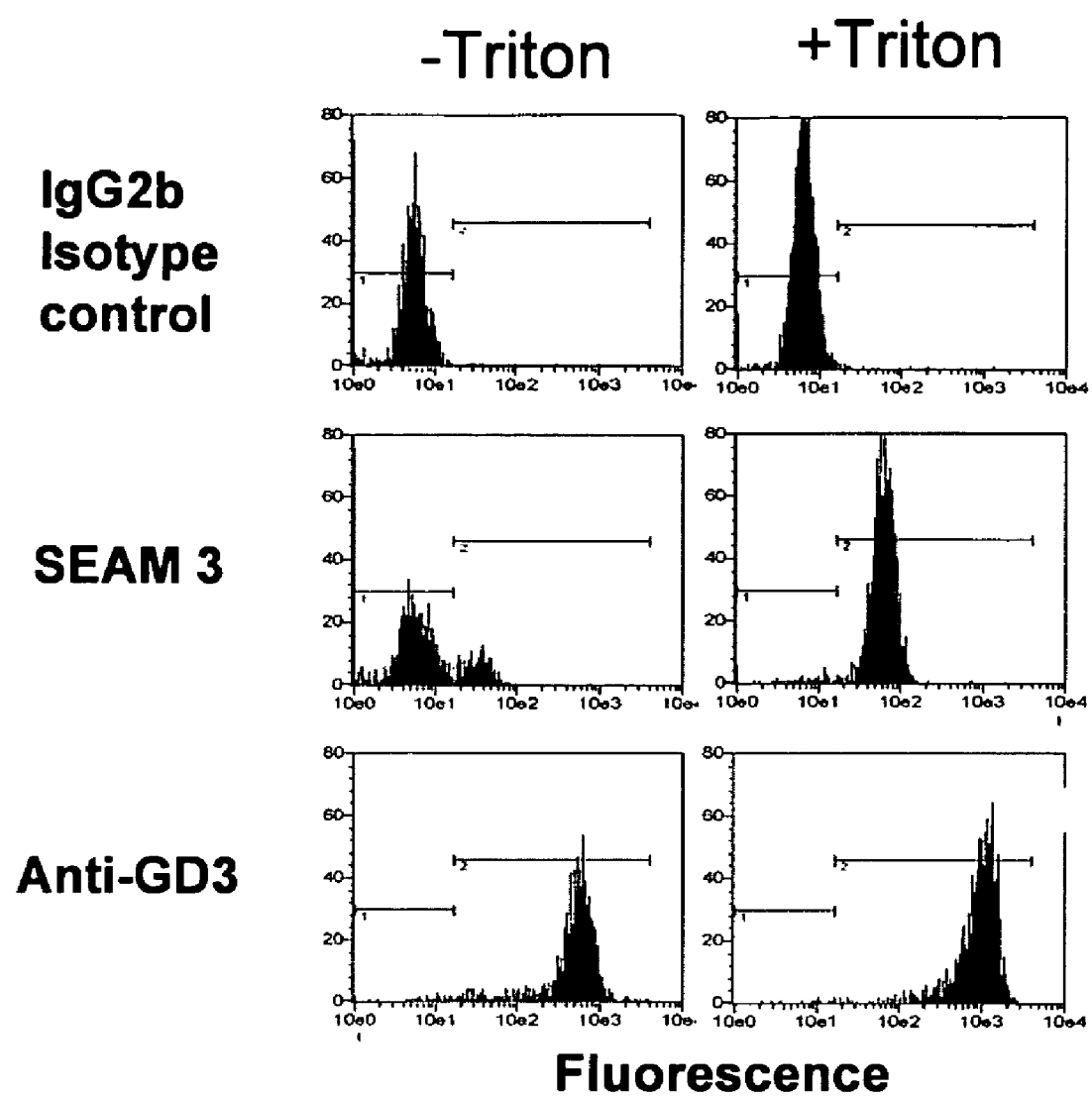
FIG. 44 is a set of graphs showing binding of SEAM 3, anti-GD3 mAb R24, and an irrelevant istotype-matched control mAb to SK-MEL 28 melanoma cells in the absence and presence of Triton X-100.
Figure 45:
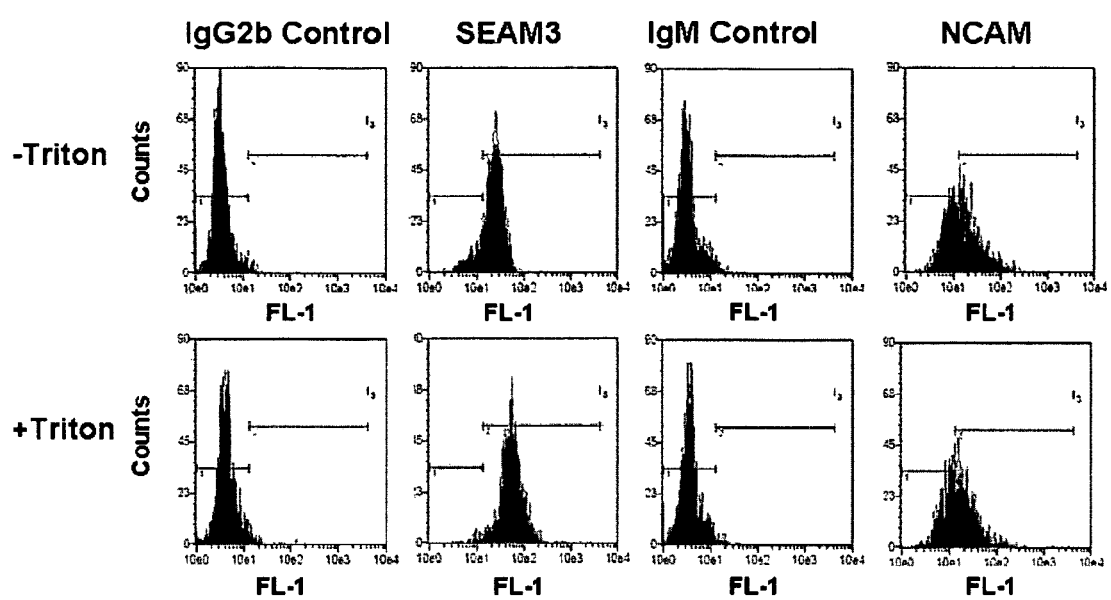
FIG. 45 is a set of graphs showing binding of SEAM 3, anti-NCAM mAb, and irrelevant istotype-matched control mAbs to CHP-134 neuroblastoma cells in the absence and presence of Triton X-100 by flow cytometry.
Figure 46:
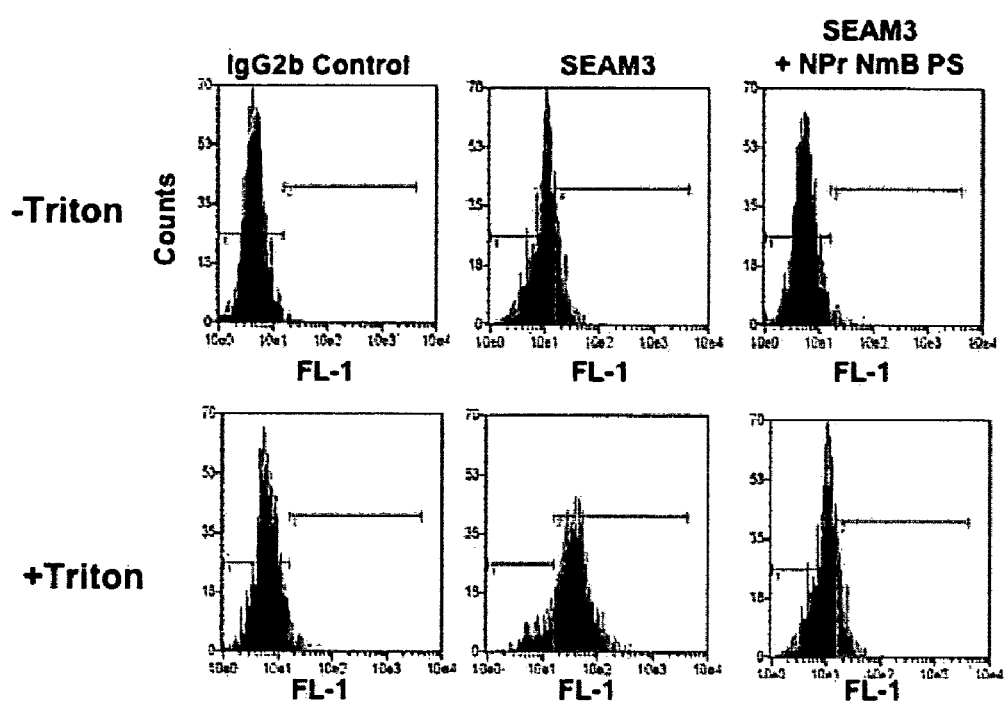
FIG. 46 is a set of graphs showing binding of SEAM 3 and an irrelevant istotype-matched control mAb to Jurkat cells in the absence and presence of Triton X-100 and the soluable polysaccharide inhibitor, N-Pr NmB PS by flow cytometry.

As shown in FIGS. 44-46, SEAM 3 binds to the surface of all three cell lines (−Triton). The greatest amount of binding was observed for the CHP-134 cells (FIG. 45) and the least in Jurkat cells (FIG. 46), although binding to Jurkat cells was still significant. All three cell lines contain larger amounts of internal SEAM 3-reactive antigen (+Triton).

Example 14

Effect of SEAM 3 Binding on the Viability of Cancer Cells

Figure 47:
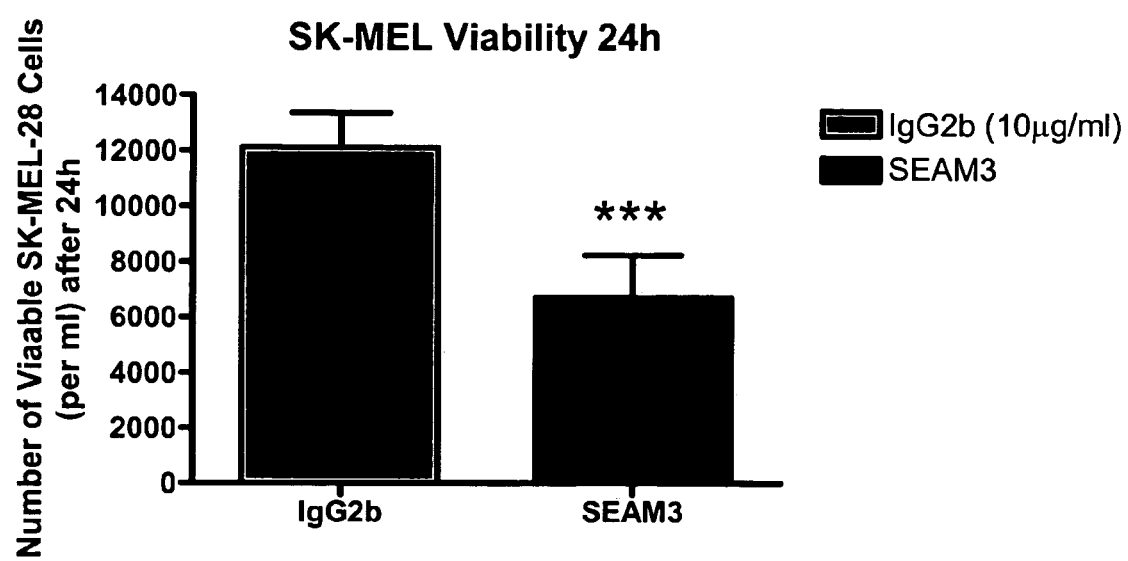
FIG. 47 is a graph showing the decrease in cell viability of SK-MEL 28 melanoma cells after incubation of cells in the presence of 5 µg/ml of SEAM 3 for 24 h.
Figure 48:
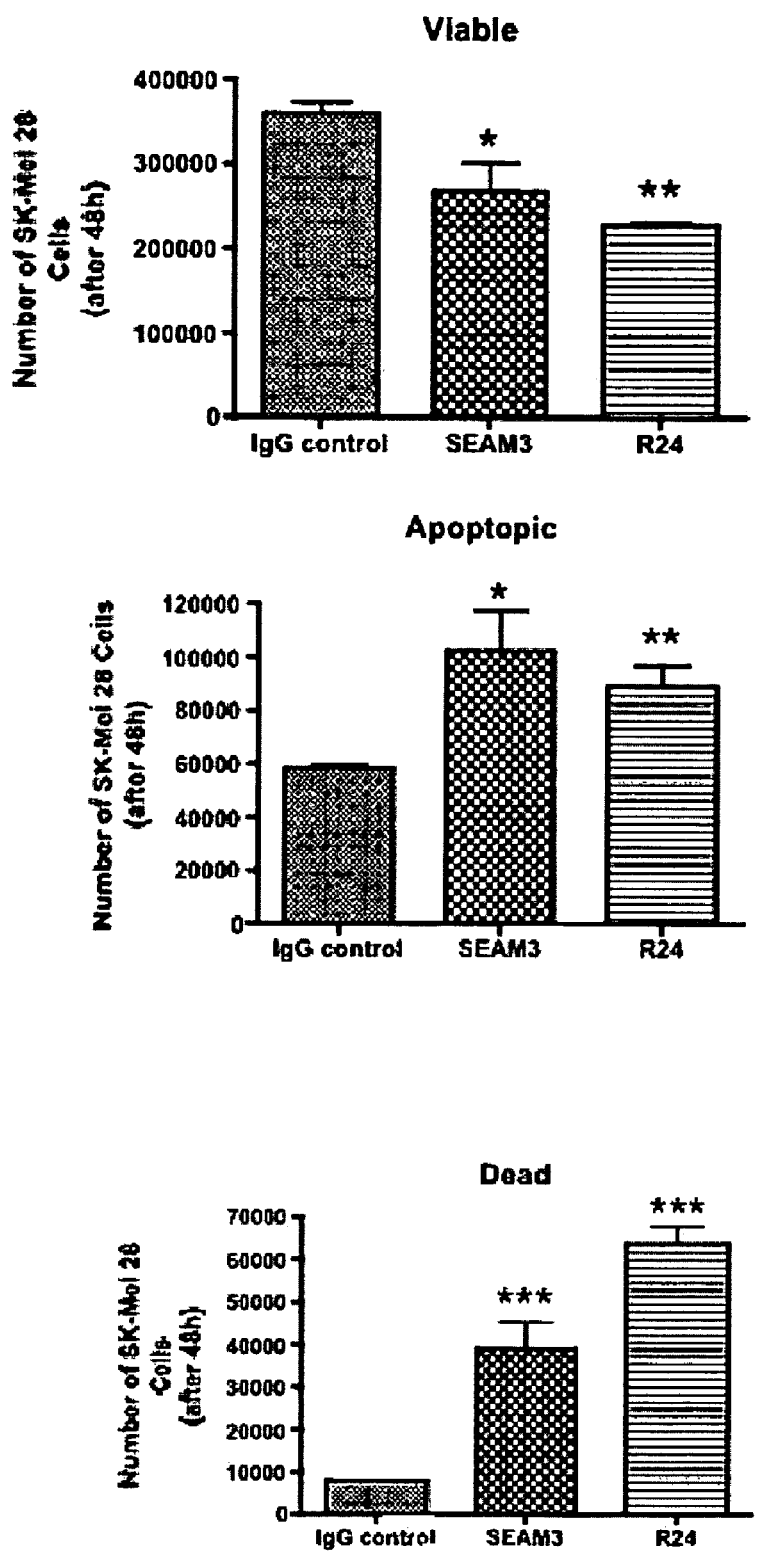
FIG. 48 are graphs comparing the decrease cell viability and increase in the number of apoptotic and dead SK-MEL 28 melanoma cells after incubation of cells in the presence of 5 µg/ml of SEAM 3, anti-GD3 mAb, R24, or an irrelevant istopye-matched control mAb for 48 h.

Cell viability of SK-MEL 28 cells incubated in the presence of SEAM 3 or control mAbs (irrelevant isotype IgG2b or anti-GD3, R24) was determined using ViaCount Reagent (Guava Technologies, Hayward, Calif.), as per manufacturers instructions. Briefly, cells that had been incubated with the mAbs for 48 h were cleaved form the tissue culture plate (as described above for the binding assays), collected by centrifugation and resuspended in ViaCount Reagent. The viability was analysed using a pre-set program on the Guava EasyCyte flowcytometer. The program has a preset gate for apoptosis and this was routinely incorporated into our studies. As shown in FIG. 47, SEAM 3 significantly decreases the number of viable cells compared to the irrelevant IgG2b control mAb (P<0.001 indicated ***) after 24 h incubation with the mAb. In a second experiment shown in FIG. 48, SEAM 3 decreases the number of viable cells compared to an IgG2b control mAb (P<0.05 indicated by *) and increases the number of apoptotic (P<0.05) and dead cells (P<0.01). Similarly, the positive control mAb, R24 decreases the number of viable cells (P<0.01 indicated **), and increases the number of apoptotic (P<0.01) and dead (P<0.001) cells compared to the negative control. The results demonstrate that SEAM 3 binding to the cell surface induces apoptosis and increases cell death.

Example 15

Correlation between SEAM 3 Binding and Cell Proliferation as Measured by th Expression of Ki-67 Antigen The data above indicated that SEAM 3 binds to the surface of cancer cells that are in some stage of cell division. To demonstrate this, SK-MEL 28 cells were analyzed for SEAM 3 binding and for the expression Ki-67 antigen, which is a marker for cell proliferation (Brown et al. Histopathology.

2002, 40:2-11). Cells were processed by the same procedures used to measure SEAM 3 binding in the absence of Triton. After unbound SEAM 3 had been washed away, cells were treated with 3% (v/v) goat serum containing 0.5% Triton to allow entry of an anti-Ki-67 antibody. After 1 h at 4° C., an anti-Ki-67 was added and incubated on-ice for 2 hours. Cells were then collected by centrifugation, washed twice with PBS, and two fluorescently labeled goat anti-mouse secondary antibodies were added, anti IgG2b-Alexa Flour 594 (Invitrogen); anti-IgM-Alexa Flour 488 (Invitrogen). After extensive washing, cells were analyzed on a Guava EasyCyte flow cytometer.

Figure 50:
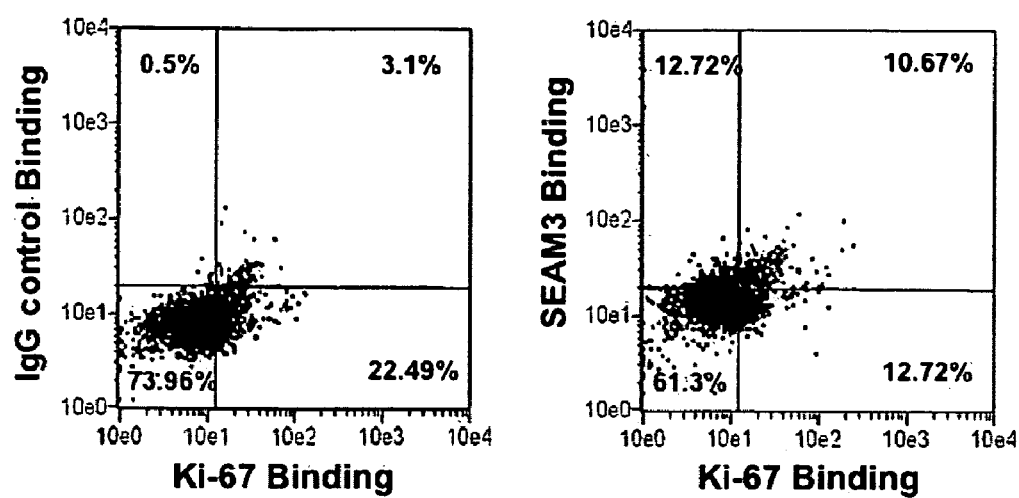
FIG. 50 is a scatter plot comparing the percentage of SK-MEL 28 cells expressing SEAM 3-reactive antigen and the cell proliferation marker Ki67.

When the cells are in exponential growth phase, approximately 20% of the cells were found to express SEAM 3-reactive antigen on their surface (by flow cytometry and fluorescence microscopy data) and 20-25% express the proliferation marker Ki-67 (by flow cytometry). As shown in FIG. 50, there is a population of cells (approximately 11%) that express both Ki-67 and SEAM 3-reactive antigen on their surface. However, there are some cells that only express Ki-67 antigen (12%) or SEAM 3-reactive antigen (13%). Detection of Ki-67 antigen maybe used to determine the percentage of tumor cells that are actively dividing in samples of cancer biopsies (Brown et al. Histopathology. 2002, 40:2-11). The number obtained through this examination is termed the "S-phase", growth, or proliferative fraction (Brown et al. Histopathology. 2002, 40:2-11). Indeed, Ki-67 is present throughout proliferation from "S-phase to at least anaphase. The flow cytometry double labeling experiment (FIG. 50) shows that the expression of Ki-67 and SEAM 3-reactive antigen on the surface of cells overlap and confirm that at least in some part, SEAM 3-reative antigen expression on the surface maybe involved in some late stage of cell division.

To further assess the affect of SEAM 3 mAb on cell growth, the stage of the cell cycle after treatment with SEAM 3 was determined. In this experiment, the cells were stained with the fluorescent DNA binding dye propidium iodide to characterize cell populations in various stages of the cell cycle and the effects of adding control antibodies, nocodazole (a drug that arrest the cells in mitosis) and SEAM 3.

Approximately $10^5$ SK-MEL 28 cells were plated on a 96-well tissue culture plate and allowed to adhere. After 24 h the medium was replaced with one that had either antibody or drug and incubated for a further 48 h. Cells were spun (to collect any cells that may have detached), and fixed in 70% ice-cold methanol (added drop wise) for at least 30 minutes at 4° C. The cells were washed twice with PBS, and to ensure that only DNA was stained, the fixed cells were treated with ribonuclease I (100 µg/ml, source) for 30 minutes at 37° C. Propidium iodide (50 µg/ml) was added and samples were analyzed using a Guava EasyCyte flow cytometer.

Figure 49:
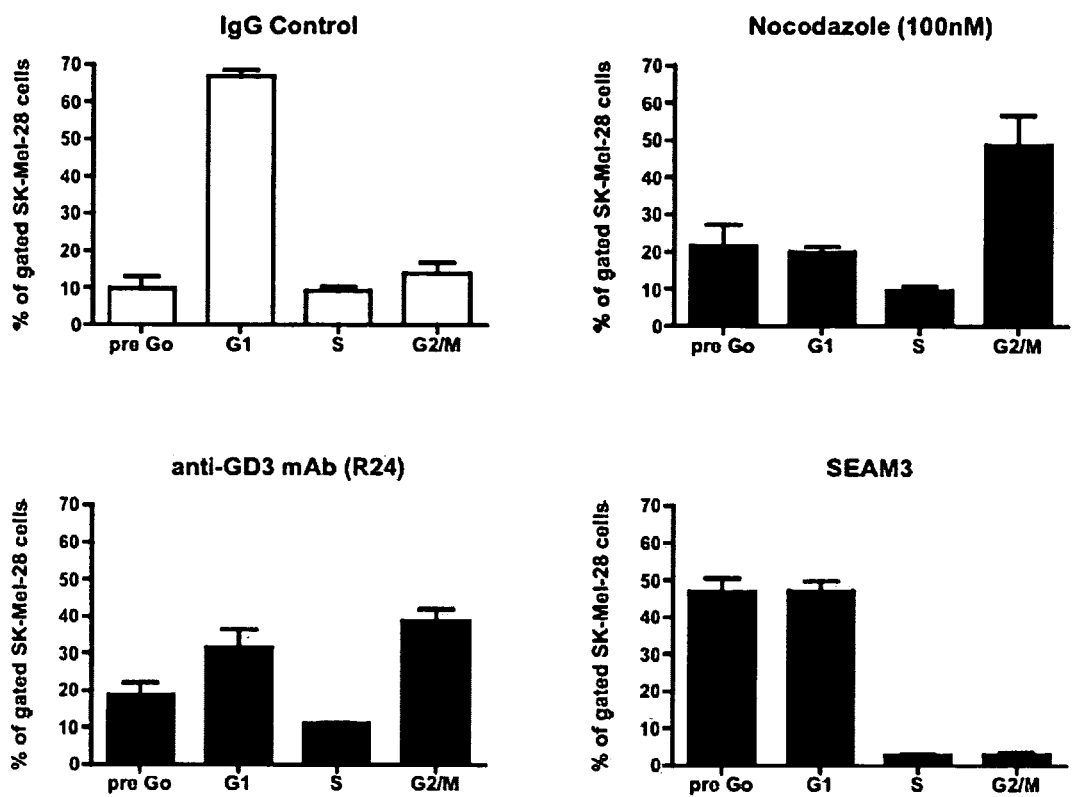
FIG. 49 are graphs showing the shift of SK-MEL 28 melanoma cells to pre Go in the presence of SEAM 3 compared to the effects of the drug nocodozole and the anti-GD3 mAb R24.

As shown in FIG. 49, the cells incubated for 48 h with an isotype-matched control antibody exhibited a profile where the majority of the cells (68%) were in Go, or at rest (non-proliferating), while 10% were in "S-phase" and a further 15% in G2/M phase. A further population (approximately 10%) of cells were in a pre-Go phase. This pre-Go phase may be indicative of apoptosis. SK-MEL-28 cells could be arrested in G2/M phase (mitosis) by treatment with nocodazole (100 nM) for 48 h (FIG. 49). In this case, approximately 50% of the cells were arrested in G2/M phase. In contrast, incubation of the cells with SEAM 3 reduced the proportion of cells in Go, S-phase and G2/M Phase, while increasing the number in pre-Go (FIG. 49).

This data provides further evidence that SEAM 3 decreases the viability of SK-MEL 28 cells and suggests that the effect of the antibody is to promote entry of the cells into the pre-Go phase. Interestingly, the cells that had been treated with the anti-ganglioside GD3 antibody (R24), which has previously been shown to kill melanoma cells, increased the number of cells in mitosis. Thus, the mechanism(s) of action of SEAM 3 on interrupting cell cycle/apoptotic mechanisms may be different from those exhibited by R24. In addition, this difference in the effect on cell cycle is further evidence that SEAM 3 and R24 bind different epitopes on cancerous cells.

Example 16

Cloning and Sequencing of Nucleic Acid Encoding the SEAM 3 mAb

To investigate the molecular basis for antigen recognition, the variable region (V) genes of five anti-N—Pr NmB PS murine mAbs that are bactericidal for *N. meningitidis* Group B bacteria were cloned and sequenced. The following materials and methods were used in this example.

Methods and Materials mAbs The anti-N—Pr NmB PS murine mAbs SEAM 2 (IgG3), SEAM 3 (IgG2b), SEAM 12 (IgG2a), SEAM 18 (IgG2a) are representative of each of the four fine antigenic specificity groups described previously (Granoff et al. (1998) J Immunol 160, 5028-36). SEAM 35 (IgG2a) also was included because it exhibits greater cross-reactivity with polysialic acid antigens expressed by the human neuronal cell line CHP-134 than that of the other four SEAM mAbs. The mAbs are bactericidal in the presence of complement and confer passive protection against meningococcal bacteremia in an infant rat model. SEAM 2 and SEAM 3 have no detectable autoreactive activity with host polysialic acid while SEAM 12 and SEAM 18 show minimal cross-reactivity.

dsDNA ELISA. mAb binding to dsDNA was measured using methods described by Gilkeson et al. (1993) J Immunol 151, 1353-64. The positive control anti-DNA mAb was obtained from QED Biosciences (San Diego, Calif.) and isotype-matched irrelevant mAbs were obtained from Southern Biotech Inc. (Birmingham, Ala.).

V gene sequencing. Variable region genes of immunoglobulin heavy and light chains from mouse hybridoma cell lines were amplified by PCR using degenerate primers and cloned into the vector pGEM3zf (Promega, Madison, Wis.) as described by Wang et al. (2000) J Immunol Methods 233, 167-77 using *E. coli* strain XL-2 Blue as a host. Plasmid DNA from individual transformants selected on LB-ampicillin plates was isolated using the Qiagen Mini Prep Kit (Qiagen) according to the manufacturers instructions. The cloned V genes were sequenced by BioNexus (Oakland, Calif.).

V gene sequence analysis. The mAb nucleotide sequences were analyzed using IGMT/V-QUEST and the mouse immunoglobulin nucleotide sequence data-base through the online web facilities of the international ImMunoGeneTics® information system (IMGT, on the internet at imgt.cines.fr) that was initiated and coordinated by Marie-Paule Lefranc (Université Montpellier II, CNRS, LIGM, IGH, IFR3, Montpellier, France). Putative germline genes were selected based on the closest match between germline sequence in the database and cloned V gene sequence. Both amino acid and gene sequences were compared to respective sequences in the GenBank non-redundant sequence databases using BLAST (Altschul et al. (1997) Nucleic Acids Res 25, 3389-402). In addition, putative germline genes used by a hybridoma clone expressing the anti-NmB PS murine mAb, 735 (IgG2a) were identified from the literature. Since only the amino acid sequence of this mAb was available (Klebert et al. 1993 Biol Chem Hoppe Seyler 374, 993-1000; Vaesen et al. (1991) Biol Chem Hoppe Seyler 372, 451-3), the predicted germline gene for this mAb is based on the closest amino acid sequence match in the IGMT/V-QUEST and GenBank/EMBL databases (Chenna et al. (2003) Nucleic Acids Res 31, 3497-500). We also included in our comparative analysis the gene sequences and germline gene assignments for the anti-NmB PS mAb 2-2-B (IgM, Mandrell et al. (1982) J Immunol 129, 2172-8) reported by Berry et al. ((2005) Mol Immunol 42, 335-44).

Results

Figure 56:
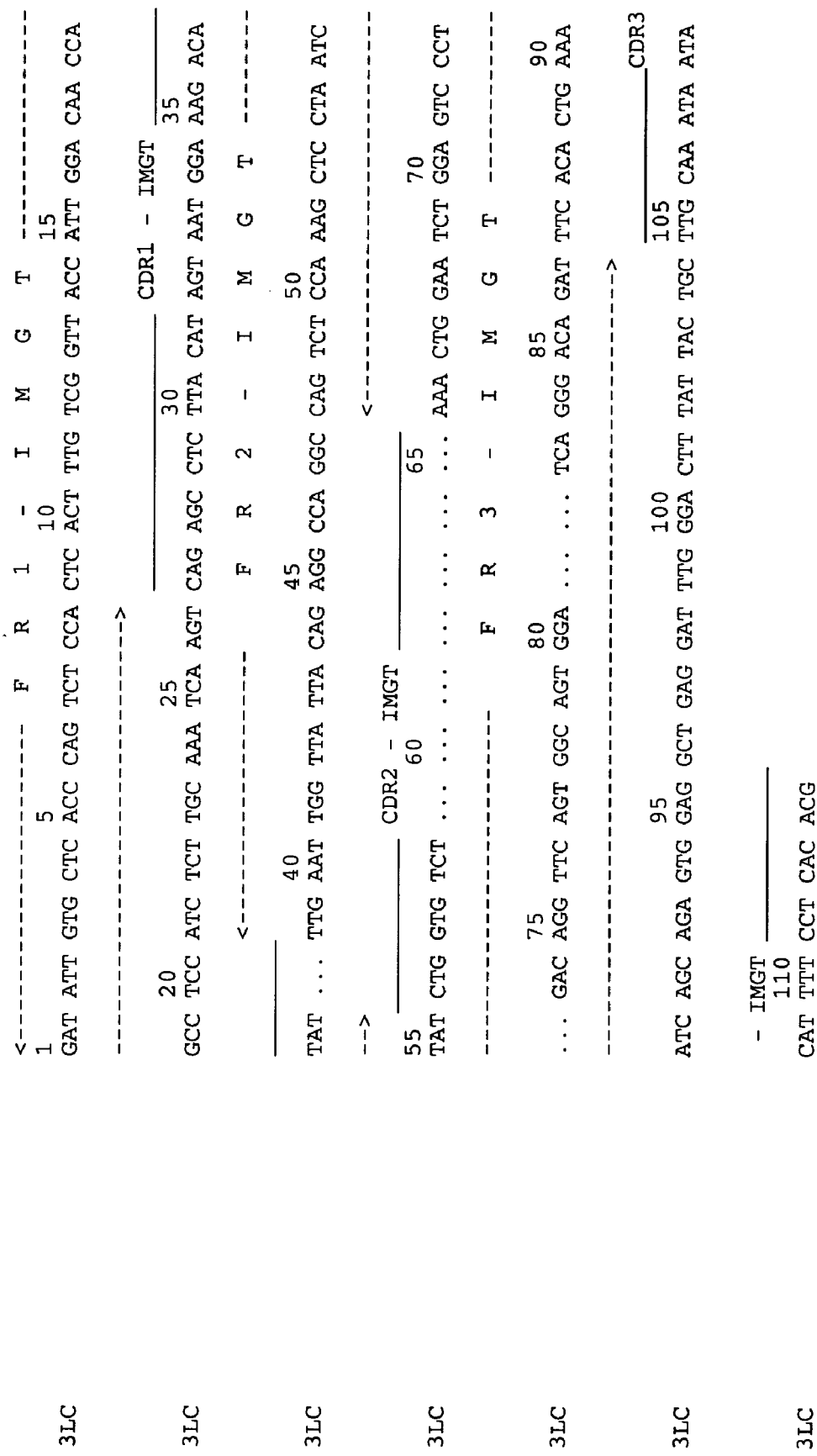
FIG. 56 is a schematic showing the relationship of the DNA sequences of the SEAM3 light chain (SEQ ID NO:18) to variable region framework and CDRs as defined by International Immunogenetics Information System (IMGT) definitions (Lefranc et al. IMGT, the international ImMunoGeneTics information system®. Nucl. Acids Res., 2005, 33, D593-D597).
Figure 57:
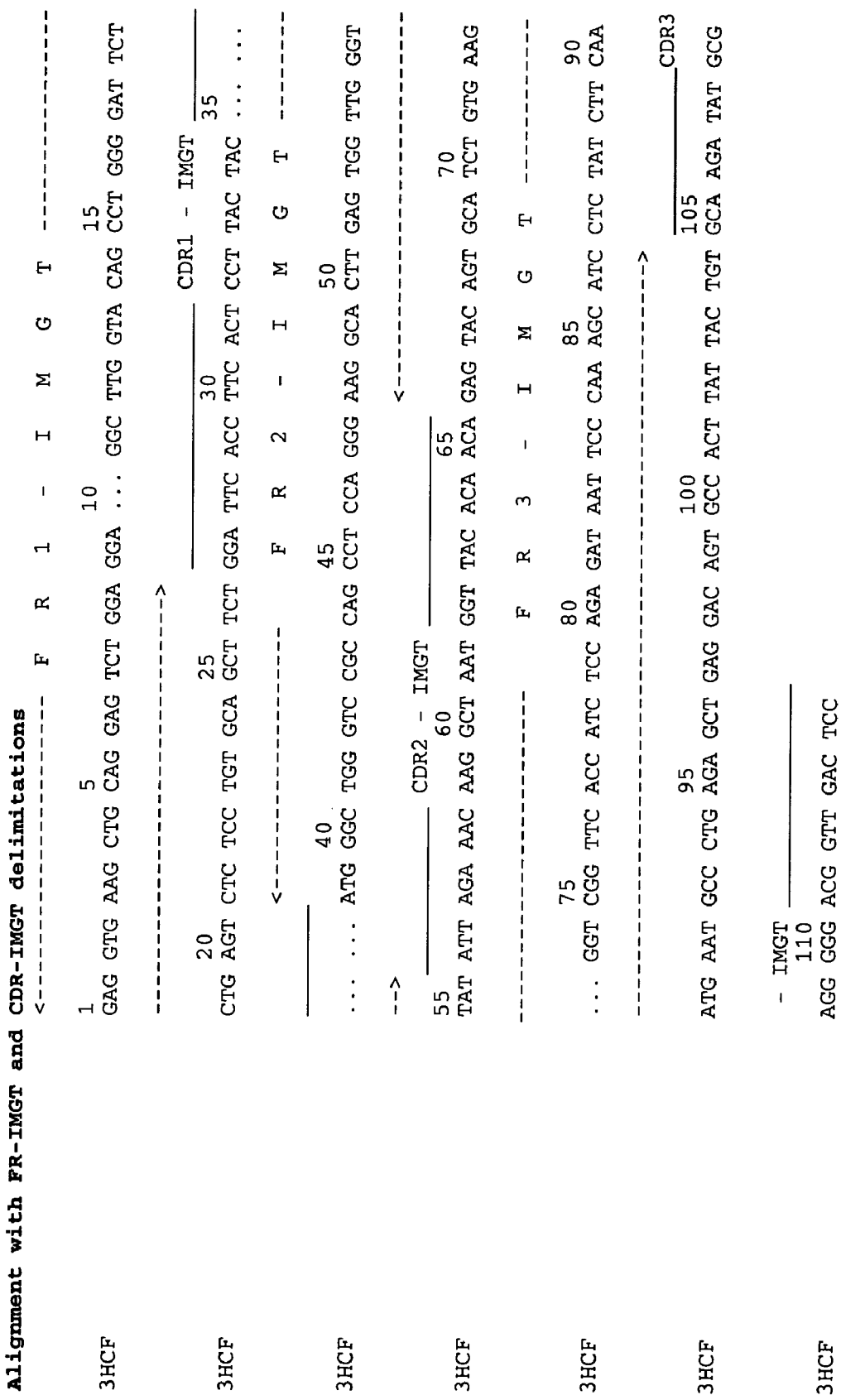
FIG. 57 is a schematic showing the relationship of the DNA sequences of the SEAM3 heavy chain (SEQ ID NO:19) to variable region framework and CDRs as defined by International Immunogenetics Information System (IMGT) definitions (Lefranc et al. IMGT, the international ImMunoGeneTics information system®. Nucl. Acids Res., 2005, 33, D593-D597).

Analysis of nucleic acid and amino acid sequences of variable regions of SEAM 3 heavy chain and light chain polypeptides. The nucleic acid and amino acid sequences of the variable regions of the SEAM 3 heavy chain polypeptide and light chain polypeptide are provided in FIG. 51. FIGS. 52 and 53 show the SEAM 3 light chain and heavy chain variable region DNA sequences, respectively, with the framework (denoted by, e.g., FR1-IMTG; FIGS. 56-58) and CDR regions indicated as defined by the International Immunogenetics Information System (IMGT) definitions (Lefranc et al. IMGT, the international ImMunoGeneTics information system®. Nucl. Acids Res., 2005, 33, D593-D597).

Variable region gene usage of murine anti-N—Pr NmB PS mAbs The germline gene usage for the anti-N—Pr NmB PS and anti-NmB PS mAbs are compared in the table provided in FIG. 55. The respective amino acid sequences are shown in FIGS. 50 and 51. The V region repertoire is restricted to a relatively few highly related VL or VH gene families. For example, SEAM 2 and SEAM 3, which have different fine antigenic specificities, have identical VL amino acid sequences (FIG. 52), and the VL gene is from the same family gene family (IgGKV1) as that encoding the autoreactive anti-NmB PS mAbs, 2-2-B and 735 (FIG. 55). Similarly, the VL genes used by SEAM 12 and SEAM 18, which have different fine antigenic specificities, are from the same family (IgGKV4). The respective VH sequences of SEAM 3 and SEAM 18 are nearly identical to each other (96% identity), and are from the same germline gene family (IgGHV7S3) used for SEAM 35 VH (FIG. 55). The germline VH genes for SEAM 2 and SEAM 12 are different from each other and from the other three anti-N—Pr NmB PS mAbs but the germline VH gene used for SEAM 2 is related to those used by the two autoreactive anti-NmB PS mAbs, 2-2-B and 735 (both 72% identical).

Anti-NmB PS mAbs, 2-2-B and 735 are reactive with NmB PS while anti-N Pr NmB PS SEAM 2 is not. The close homology of both the respective heavy and light chain V amino acid sequences between SEAM 2 and the autoreactive mAbs 2-2-B and 735 (VH 70%, VL 75%), is therefore of particular interest. The most striking difference between the two sequences is in the heavy chain (H—CDR3) where SEAM 2 consists of the minimal 4 amino acids, two of which are glycine, compared with a length of 8 amino acids in mAb 735.

The VL and VH genes of anti-NmB PS mAb 2-2-B are unmutated (100% identical) as compared with their putative germline genes (FIG. 55). Similarly, the amino acid sequence of the expressed VL of anti-NmB PS mAb 735 is >99% identical to that of the assigned germline gene. In contrast, the anti-N—Pr NmB PS mAbs have a greater percentage of mutations as compared with the respective germline sequences (the expressed genes are 89% to 95% identical to germline sequences, FIG. 55). Also, all five anti-N—Pr NmB PS mAbs contain one or more arginine residues in H—CD3, which are encoded by editing at the D-J junction. Neither of the two anti-NmB PS mAbs contain arginine in H—CDR3.

What is claimed is:

1. A method of inhibiting growth of a cancerous cell in a subject, the method comprising:
    administering to a subject a pharmaceutically acceptable formulation comprising an isolated antibody that specifically binds a de-N-acetylated sialic acid (deNAc SA) epitope on an extracellularly accessible surface of a cancerous cell present in the subject, said deNAc SA epitope minimally defined by a dimer containing at least one de-N-acetylated sialic acid residue having a free amine adjacent an N-acylated sialic acid residue or a sialic acid derivative residue, said isolated antibody separated from cationic or other charged contaminants;
    wherein said administering facilitates reduction in viability of cancerous cells bound by the antibody.

2. The method of claim 1, wherein the deNAc SA epitope is presented on a surface of the cancerous cell during cell division.

3. The method of claim 1, wherein the cancer is a melanoma or a leukemia.

4. The method of claim 1, wherein the cancer is a neuroblastoma.

5. The method of claim 1, wherein the antibody is administered by infusion or by local injection.

6. The method of claim 1, wherein said administering is prior to surgical intervention to remove cancerous cells.

7. The method of claim 1, wherein said administering is at the time of or after surgical intervention to remove cancerous cells.

8. The method of claim 1 further comprising:
    administering at least one of a cancer chemotherapy or a radiation therapy to the subject.

9. A method of inhibiting growth of a cancerous cell in a subject, the method comprising:
    administering to a subject a pharmaceutically acceptable formulation comprising an isolated antibody that specifically binds a SEAM-3 reactive antigen on an extracellularly accessible surface of a cancerous cell present in the subject, said isolated antibody separated from cationic or other charged contaminants;

wherein said administering facilitates reduction in viability of cancerous cells bound by the antibody.

10. The method of claim 9, wherein the SEAM 3 reactive antigen is presented on a surface of the cancerous cell during cell division.

11. The method of claim 9, wherein the cancer is a melanoma or a leukemia.

12. The method of claim 9, wherein the cancer is a neuroblastoma.

13. The method of claim 9, wherein the antibody is administered by infusion or by local injection.

14. The method of claim 9, wherein said administering is prior to, at the time of, or after surgical intervention to remove cancerous cells.

15. The method of claim 9 further comprising administering at least one of a cancer chemotherapy or radiation therapy to the subject.

16. The method of claim 9, wherein the isolated antibody is a SEAM 3 monoclonal antibody (ATCC Deposit No. HB-12170).

17. The method of claim 16, wherein the SEAM 3 monoclonal antibody is isolated by the method of:

incubating a composition comprising a SEAM 3 monoclonal antibody (mAb) in a high salt concentration solution, said incubating being under conditions suitable to facilitate separation of charged molecules from the SEAM 3 mAb in the solution; and isolating the SEAM 3 mAb from the solution.

18. A method of eliciting antibodies to a cancerous cell in a subject, the method comprising:

administering to a subject an immunogenic composition comprising a de-N-acetylated sialic acid (deNAc SA) antigen and an adjuvant, wherein the subject has or is suspected of having a cancer characterized by a de-N-acetylated sialic acid (deNAc SA) antigen, the deNAc SA antigen of said composition comprising less than 60% by weight N-acylated polysialic acid and an epitope minimally defined by a dimer containing at least one de-N-acetylated sialic acid residue having a free amine adjacent an N-acylated sialic acid residue or a sialic acid derivative residue, wherein said administering is effective to elicit production of an antibody that specifically binds a deNAc SA epitope on an extracellularly accessible surface of a cancerous cell.

19. The method of claim 18, wherein the cancer is a melanoma or a lymphoma.

20. The method of claim 18, wherein the cancer is a neuroblastoma.

21. The method of claim 18, wherein the deNAc SA antigen of the immunogenic composition is resistant to exosialidase treatment.

22. The method of claim 18, wherein the deNAc SA antigen is a deNAc SA antigen conjugate.

23. The method of claim 22, wherein the deNAc SA antigen conjugate is a propionyl-linked or acetyl-linked deNAc SA antigen conjugate.

* * * * *

UNITED STATES PATENT AND TRADEMARK OFFICE
CERTIFICATE OF CORRECTION

| | |
|---|---|
| PATENT NO. | : 8,148,335 B2 |
| APPLICATION NO. | : 11/645255 |
| DATED | : April 3, 2012 |
| INVENTOR(S) | : Gregory R. Moe |

It is certified that error appears in the above-identified patent and that said Letters Patent is hereby corrected as shown below:

In the Specification

In column 1, lines 19-23, please replace "This invention was made with government support under grants no. AI46464 and AI45642 awarded by the National Institute of Allergy and Infectious Diseases, and the National Institute of Health. The government has certain rights in this invention" with --This invention was made with government support under grant no. AI46464 awarded by the National Institute of Allergy and Infectious Diseases; and with government support under grant no. AI45642 awarded by the National Institute of Health. The government has certain rights in the invention--.

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 114
<212> TYPE: PRT
<213> ORGANISM: mouse

<400> SEQUENCE: 1

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Pro Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Gly Gly Thr Arg Leu Glu Ile Lys
            100                 105                 110

Arg Ala

<210> SEQ ID NO 2
<211> LENGTH: 114
```

```
<212> TYPE: PRT
<213> ORGANISM: mouse

<400> SEQUENCE: 2

Glu Leu Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala

<210> SEQ ID NO 3
<211> LENGTH: 114
<212> TYPE: PRT
<213> ORGANISM: mouse

<400> SEQUENCE: 3

Asp Ile Val Met Thr Gln Ser Pro Leu Thr Leu Ser Val Thr Ile Gly
 1               5                  10                  15

Gln Pro Ala Ser Ile Ser Cys Lys Ser Ser Gln Ser Leu Leu His Ser
            20                  25                  30

Asn Gly Lys Thr Tyr Leu Asn Trp Leu Leu Gln Arg Pro Gly Gln Ser
        35                  40                  45

Pro Lys Leu Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Leu Gln Ile
                85                  90                  95

Ile His Phe Pro His Thr Phe Gly Ala Gly Thr Lys Leu Glu Leu Lys
            100                 105                 110

Arg Ala

<210> SEQ ID NO 4
<211> LENGTH: 109
<212> TYPE: PRT
<213> ORGANISM: mouse

<400> SEQUENCE: 4

Asp Ile Val Met Thr Gln Ser Pro Ile Ser Met Ser Met Ser Leu Gly
 1               5                  10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Ser Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
```

```
                65                  70                  75                  80
Glu Asp Leu Ala Asp Tyr His Cys Gly Gln Ser Tyr Asn Tyr Pro Tyr
                    85                  90                  95

Thr Phe Gly Gly Gly Thr Lys Leu Glu Ile Lys Arg Ala
                100                 105

<210> SEQ ID NO 5
<211> LENGTH: 108
<212> TYPE: PRT
<213> ORGANISM: mouse

<400> SEQUENCE: 5

Asp Ile Val Met Thr Gln Thr Thr Val Ile Met Ser Ala Ser Pro Gly
1               5                   10                  15

Glu Lys Val Thr Met Thr Cys Ser Ala Ser Ser Ser Val Thr Tyr Met
                20                  25                  30

His Trp Tyr Gln Gln Lys Ser Arg Thr Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ala Leu Thr Ile Ser Ser Met Glu Pro Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Gly Leu Lys Arg Ala
                100                 105

<210> SEQ ID NO 6
<211> LENGTH: 111
<212> TYPE: PRT
<213> ORGANISM: mouse

<400> SEQUENCE: 6

Asp Ile Val Met Thr Gln Thr Pro Thr Ile Met Ser Ala Ser Leu Gly
1               5                   10                  15

Glu Arg Val Thr Met Thr Cys Thr Ala Ser Ser Ser Val Ala Ser Ser
                20                  25                  30

Gly Tyr Leu His Trp Tyr Gln Gln Lys Pro Gly Ser Ser Pro Lys Leu
            35                  40                  45

Trp Ile Tyr Gly Thr Ser Asn Leu Ala Ser Gly Val Pro Ala Arg Phe
        50                  55                  60

Ser Gly Ser Gly Ser Gly Thr Ser Tyr Ser Leu Thr Leu Ser Ser Val
65                  70                  75                  80

Glu Ala Glu Asp Ala Ala Thr Tyr Tyr Cys His Gln Tyr His Arg Ser
                85                  90                  95

His Tyr Thr Phe Gly Gly Gly Thr Lys Leu Glu Ile Lys Arg Ala
                100                 105                 110

<210> SEQ ID NO 7
<211> LENGTH: 118
<212> TYPE: PRT
<213> ORGANISM: mouse

<400> SEQUENCE: 7

Glu Val Lys Leu Gln Glu Ser Gly Gly Gly Leu Val Gln Pro Gly Asp
1               5                   10                  15

Ser Leu Ser Leu Ser Cys Ala Ala Ser Gly Phe Thr Phe Thr Pro Tyr
                20                  25                  30
```

```
Tyr Met Gly Trp Val Arg Gln Pro Pro Gly Lys Ala Leu Glu Trp Leu
         35                  40                  45

Gly Tyr Ile Arg Asn Lys Ala Asn Gly Tyr Thr Thr Glu Tyr Ser Ala
         50                  55                  60

Ser Val Lys Gly Arg Phe Thr Ile Ser Arg Asp Asn Ser Gln Ser Ile
 65                  70                  75                  80

Leu Tyr Leu Gln Met Asn Ala Leu Arg Ala Glu Asp Ser Ala Thr Tyr
                 85                  90                  95

Tyr Cys Ala Arg Tyr Ala Arg Gly Thr Val Asp Ser Trp Gly Gln Gly
                100                 105                 110

Thr Thr Leu Thr Val Ser
        115
```

<210> SEQ ID NO 8
<211> LENGTH: 118
<212> TYPE: PRT
<213> ORGANISM: mouse

<400> SEQUENCE: 8

```
Glu Val Gln Leu Glu Glu Ser Gly Gly Gly Leu Val Gln Pro Gly Asp
 1               5                  10                  15

Ser Leu Ser Leu Ser Cys Ala Ala Ser Gly Phe Thr Phe Thr Pro Tyr
                 20                  25                  30

Tyr Met Gly Trp Val Arg Gln Pro Pro Gly Lys Ala Leu Glu Trp Leu
         35                  40                  45

Gly Tyr Ile Arg Asn Lys Ala Asn Gly Tyr Thr Thr Glu Tyr Ser Ala
         50                  55                  60

Ser Val Lys Gly Arg Phe Thr Ile Ser Arg Asp Asn Ser Gln Ser Ile
 65                  70                  75                  80

Leu Tyr Leu Gln Met Asn Ala Leu Arg Ala Glu Asp Ser Ala Thr Tyr
                 85                  90                  95

Tyr Cys Ala Arg Tyr Ala Arg Gly Thr Val Asp Ser Trp Gly Gln Gly
                100                 105                 110

Thr Thr Leu Thr Val Ser
        115
```

<210> SEQ ID NO 9
<211> LENGTH: 118
<212> TYPE: PRT
<213> ORGANISM: mouse

<400> SEQUENCE: 9

```
Glu Val Lys Leu Glu Glu Ser Gly Gly Gly Leu Val Gln Pro Gly Gly
 1               5                  10                  15

Ser Leu Ser Leu Ser Cys Ala Ala Ser Gly Phe Thr Phe Thr Asp Tyr
                 20                  25                  30

Tyr Leu Ser Trp Val Arg Gln Pro Pro Gly Lys Ala Leu Glu Trp Leu
         35                  40                  45

Gly Phe Ile Arg Asn Thr Ala Asn Gly Tyr Thr Thr Glu Tyr Ser Ala
         50                  55                  60

Ser Val Lys Gly Arg Phe Thr Ile Ala Arg Asp Asn Ser Gln Ser Ile
 65                  70                  75                  80

Leu Thr Leu Gln Met Asn Ala Leu Arg Ala Glu Asp Ser Ala Thr Tyr
                 85                  90                  95

Tyr Cys Ala Arg Trp Ser Arg Arg Ala Met Asp Tyr Trp Gly Gln Gly
                100                 105                 110

Thr Ser Val Thr Val Ser
```

115

<210> SEQ ID NO 10
<211> LENGTH: 118
<212> TYPE: PRT
<213> ORGANISM: mouse

<400> SEQUENCE: 10

Gln Val Lys Leu Glu Gln Ser Gly Gly Leu Val Arg Pro Gly Asn
1               5                   10                  15

Ser Leu Lys Leu Ser Cys Val Thr Ser Gly Phe Thr Phe Ile Asn Tyr
                20                  25                  30

Arg Met His Trp Leu Arg Gln Pro Pro Gly Lys Arg Leu Glu Trp Ile
            35                  40                  45

Ala Val Ile Thr Asp Asn Ser Asp Asn Tyr Val Asn Tyr Ala Glu
        50                  55                  60

Ser Val Lys Gly Arg Phe Ala Ile Ser Arg Asp Asp Ser Lys Ser Ser
65                  70                  75                  80

Val Tyr Leu Glu Met Asn Arg Leu Arg Glu Glu Asp Thr Ala Thr Tyr
                85                  90                  95

Phe Cys Ser Arg Ser Arg Arg Ser Phe Phe Asp Tyr Trp Gly Gln Gly
            100                 105                 110

Thr Thr Leu Thr Val Ser
            115

<210> SEQ ID NO 11
<211> LENGTH: 116
<212> TYPE: PRT
<213> ORGANISM: mouse

<400> SEQUENCE: 11

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
                20                  25                  30

Tyr Ile His Trp Val Lys Gln Arg Pro Gly Glu Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Lys Phe Ala Met Asp Tyr Trp Gly Gln Gly Thr Ser
            100                 105                 110

Val Thr Val Ser
        115

<210> SEQ ID NO 12
<211> LENGTH: 118
<212> TYPE: PRT
<213> ORGANISM: mouse

<400> SEQUENCE: 12

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Val Lys Ser Leu Glu Trp Ile
            35                  40                  45

Gly Arg Ile Asn Pro Tyr Asn Gly Ala Thr Ser Tyr Asn Gln Asn Phe
 50                  55                  60

Lys Asp Lys Ala Ser Leu Thr Val Asp Lys Ser Ser Thr Ala Tyr
 65                  70                  75                  80

Met Glu Leu His Ser Leu Thr Ser Glu Asp Ser Ala Val Tyr Tyr Cys
                85                  90                  95

Ala Arg Gly Asp Tyr Gly Asn Ser Leu Phe Asp Tyr Trp Gly Gln Gly
                100                 105                 110

Thr Thr Leu Thr Val Ser
            115

<210> SEQ ID NO 13
<211> LENGTH: 112
<212> TYPE: PRT
<213> ORGANISM: mouse

<400> SEQUENCE: 13

Glu Val Gln Leu Glu Glu Ser Gly Thr Glu Leu Val Lys Pro Gly Ala
 1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Thr Asn Gly Gly Ile His Phe Asn Glu Lys Phe
 50                  55                  60

Arg Thr Lys Ala Ala Leu Thr Val Asp Lys Ser Ser Ser Thr Ala Phe
 65                  70                  75                  80

Leu His Leu Ser Ser Leu Thr Ser Glu Asp Ser Ala Val Tyr Tyr Cys
                85                  90                  95

Ala Arg Arg Gly Gly Tyr Trp Gly His Gly Thr Thr Leu Thr Val Ser
                100                 105                 110

<210> SEQ ID NO 14
<211> LENGTH: 110
<212> TYPE: PRT
<213> ORGANISM: mouse

<400> SEQUENCE: 14

Glu Val Lys Leu Gln Glu Ser Gly Gly Gly Leu Val Gln Pro Gly Asp
 1               5                   10                  15

Ser Leu Ser Leu Ser Cys Ala Ala Ser Gly Phe Thr Phe Thr Pro Tyr
                20                  25                  30

Tyr Met Gly Trp Val Arg Gln Pro Pro Gly Lys Ala Leu Glu Trp Leu
            35                  40                  45

Gly Tyr Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Ala Leu Arg Ala Glu Asp Ser Ala Thr Tyr
                85                  90                  95

Tyr Cys Ala Arg Tyr Ala Arg Gly Thr Val Asp Ser Trp Gly
                100                 105                 110

<210> SEQ ID NO 15
<211> LENGTH: 330
<212> TYPE: DNA

<213> ORGANISM: mouse

<400> SEQUENCE: 15

| | | |
|---|---|---|
| gaggtgaagc tgcaggagtc tggaggaggc ttggtacagc ctggggattc tctgagtctc | 60 |
| tcctgtgcag cttctggatt caccttcact ccttactaca tgggctgggt ccgccagcct | 120 |
| ccagggaagg cacttgagtg gttgggttat attagaaaca aggctaatgg ttacacaaca | 180 |
| gagtacagtg catctgtgaa gggtcggttc accatctcca gagataattc ccaaagcatc | 240 |
| ctctatcttc aaatgaatgc cctgagagct gaggacagtg ccacttatta ctgtgcaaga | 300 |
| tatgcgaggg ggacggttga ctcctggggc | 330 |

<210> SEQ ID NO 16
<211> LENGTH: 104
<212> TYPE: PRT
<213> ORGANISM: mouse

<400> SEQUENCE: 16

Asp Ile Val Leu Thr Gln Ser Pro Leu Thr Leu Ser Val Thr Ile Gly
1               5                   10                  15
Gln Pro Ala Ser Ile Ser Cys Lys Ser Ser Gln Ser Leu Leu His Ser
            20                  25                  30
Asn Gly Lys Thr Tyr Leu Asn Trp Leu Leu Gln Arg Pro Gly Gln Ser
        35                  40                  45
Pro Lys Leu Leu Ile Tyr Leu Val Ser Lys Leu Glu Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Leu Tyr Tyr Cys Leu Gln Ile
                85                  90                  95
Ile His Phe Pro His Thr Phe Gly
            100

<210> SEQ ID NO 17
<211> LENGTH: 312
<212> TYPE: DNA
<213> ORGANISM: mouse

<400> SEQUENCE: 17

| | | |
|---|---|---|
| gatattgtgc tcacccagtc tccactcact ttgtcggtta ccattggaca accagcctcc | 60 |
| atctcttgca aatcaagtca gagcctctta catagtaatg gaaagacata tttgaattgg | 120 |
| ttattacaga ggccaggcca gtctccaaag ctcctaatct atctggtgtc taaactggaa | 180 |
| tctggagtcc ctgacaggtt cagtggcagt ggatcaggga cagatttcac actgaaaatc | 240 |
| agcagagtgg aggctgagga tttgggactt tattactgct tgcaaataat acattttcct | 300 |
| cacacgttcg gt | 312 |

<210> SEQ ID NO 18
<211> LENGTH: 306
<212> TYPE: DNA
<213> ORGANISM: mouse

<400> SEQUENCE: 18

| | | |
|---|---|---|
| gatattgtgc tcacccagtc tccactcact ttgtcggtta ccattggaca accagcctcc | 60 |
| atctcttgca aatcaagtca gagcctctta catagtaatg gaaagacata tttgaattgg | 120 |
| ttattacaga ggccaggcca gtctccaaag ctcctaatct atctggtgtc taaactggaa | 180 |
| tctggagtcc ctgacaggtt cagtggcagt ggatcaggga cagatttcac actgaaaatc | 240 |

```
agcagagtgg aggctgagga tttgggactt tattactgct tgcaaataat acattttcct    300
cacacg                                                               306

<210> SEQ ID NO 19
<211> LENGTH: 324
<212> TYPE: DNA
<213> ORGANISM: mouse

<400> SEQUENCE: 19
gaggtgaagc tgcaggagtc tggaggaggc ttggtacagc ctggggattc tctgagtctc     60
tcctgtgcag cttctggatt caccttcact ccttactaca tgggctgggt ccgccagcct    120
ccagggaagg cacttgagtg gttgggttat attagaaaca aggctaatgg ttacacaaca    180
gagtacagtg catctgtgaa gggtcggttc accatctcca gagataattc ccaaagcatc    240
ctctatcttc aaatgaatgc cctgagagct gaggacagtg ccacttatta ctgtgcaaga    300
tatgcgaggg ggacggttga ctcc                                           324

<210> SEQ ID NO 20
<211> LENGTH: 65
<212> TYPE: DNA
<213> ORGANISM: mouse

<400> SEQUENCE: 20 cgaggggggac ggttgactcc tggggccaag gcaccactct cacagtctcc tcagccaaaa    60
caaca                                                                65

<210> SEQ ID NO 21
<211> LENGTH: 15
<212> TYPE: PRT
<213> ORGANISM: mouse

<400> SEQUENCE: 21

Cys Ala Arg Tyr Ala Arg Gly Thr Val Asp Ser Trp Gly Gln Gly
 1               5                  10                  15

<210> SEQ ID NO 22
<211> LENGTH: 45
<212> TYPE: DNA
<213> ORGANISM: mouse

<400> SEQUENCE: 22
tgtgcaagat atgcgagggg gacggttgac tcctggggcc aaggc                     45
```